United States Patent
Chang et al.

(10) Patent No.: US 11,801,138 B2
(45) Date of Patent: Oct. 31, 2023

(54) SUTURE DEPLOYMENT OF PROSTHETIC HEART VALVE

(71) Applicant: Edwards Lifesciences Corporation, Irvine, CA (US)

(72) Inventors: Arvin T. Chang, Yorba Linda, CA (US); Yair A. Neumann, Moshav Sede Varburg (IL); Gil Senesh, Irvine, CA (US); Hernan Altman, Kiryat Tivon (IL); Scott Louis Pool, Laguna Hills, CA (US); Hannah Gibson, Costa Mesa, CA (US); Amanda Kristine Anderson White, Menlo Park, CA (US); Peter Phong Tran, Irvine, CA (US); Ly Th Phan, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 912 days.

(21) Appl. No.: 16/808,145

(22) Filed: Mar. 3, 2020

(65) Prior Publication Data

US 2020/0197175 A1 Jun. 25, 2020

Related U.S. Application Data

(62) Division of application No. 15/366,959, filed on Dec. 1, 2016, now Pat. No. 10,583,007.
(Continued)

(51) Int. Cl.
*A61F 2/24* (2006.01)
(52) U.S. Cl.
CPC .......... *A61F 2/2439* (2013.01); *A61F 2/2418* (2013.01); *A61F 2/2436* (2013.01)

(58) Field of Classification Search
CPC .... A61F 2/2418; A61F 2/2436; A61F 2/2439; A61F 2/95; A61F 2002/9505; A61F 2002/9511
See application file for complete search history.

(56) References Cited

U.S. PATENT DOCUMENTS

| | | |
|---|---|---|
| 4,035,849 A | 7/1977 | Angell et al. |
| 4,592,340 A | 6/1986 | Boyles |
| (Continued) | | |

FOREIGN PATENT DOCUMENTS

| | | |
|---|---|---|
| AU | 2011253586 B2 | 4/2014 |
| DE | 19532846 A1 | 3/1997 |
| (Continued) | | |

OTHER PUBLICATIONS

Ted Feldman et al., "Prospects for Percutaneous Valve Therapies", Circulation, Journal of the American Heart Association, Dallas, TX, 2007, pp. 2866-2877.
(Continued)

*Primary Examiner* — Ashley L Fishback
(74) *Attorney, Agent, or Firm* — Edwards Lifesciences; Linda Allyson Nassif

(57) ABSTRACT

A method for delivering a prosthetic valve to a native annulus of a heart can include inserting a delivery apparatus into a patient's body, advancing the delivery apparatus to an implantation location within the native annulus, retracting a delivery sheath of the delivery apparatus relative to the prosthetic valve to expose the prosthetic valve from a distal end of the delivery sheath, and after the prosthetic valve is exposed from the delivery sheath, expanding the prosthetic valve from a radially compressed state to a radially expanded state by reducing axial tension on a first end and a second end of the prosthetic valve.

18 Claims, 33 Drawing Sheets

Related U.S. Application Data

(60) Provisional application No. 62/262,307, filed on Dec. 2, 2015.

(56) References Cited

U.S. PATENT DOCUMENTS

| | | | |
|---|---|---|---|
| 4,994,077 | A | 2/1991 | Dobben |
| 5,059,177 | A | 10/1991 | Towne et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,639,274 | A | 6/1997 | Fischell et al. |
| 5,683,451 | A | 11/1997 | Lenker et al. |
| 5,728,068 | A | 3/1998 | Leone et al. |
| 5,749,921 | A | 5/1998 | Lenker et al. |
| 5,840,081 | A | 11/1998 | Andersen et al. |
| 5,968,068 | A | 10/1999 | Dehdashtian et al. |
| 6,168,614 | B1 | 1/2001 | Andersen et al. |
| 6,187,016 | B1 | 2/2001 | Hedges et al. |
| 6,217,585 | B1 | 4/2001 | Houser et al. |
| 6,379,372 | B1 | 4/2002 | Dehdashtian et al. |
| 6,454,799 | B1 | 9/2002 | Schreck |
| 6,458,153 | B1 | 10/2002 | Bailey et al. |
| 6,461,382 | B1 | 10/2002 | Cao |
| 6,527,979 | B2 | 3/2003 | Constantz et al. |
| 6,582,462 | B1 | 6/2003 | Andersen et al. |
| 6,652,578 | B2 | 11/2003 | Bailey et al. |
| 6,676,692 | B2 | 1/2004 | Rabkin et al. |
| 6,730,118 | B2 | 5/2004 | Spenser et al. |
| 6,733,525 | B2 | 5/2004 | Yang et al. |
| 6,767,362 | B2 | 7/2004 | Schreck |
| 6,830,584 | B1 | 12/2004 | Seguin |
| 6,893,460 | B2 | 5/2005 | Spenser et al. |
| 6,908,481 | B2 | 6/2005 | Cribier |
| 6,936,058 | B2 | 8/2005 | Forde et al. |
| 7,018,406 | B2 | 3/2006 | Seguin et al. |
| 7,018,408 | B2 | 3/2006 | Bailey et al. |
| 7,276,084 | B2 | 10/2007 | Yang et al. |
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,510,575 | B2 | 3/2009 | Spenser et al. |
| 7,585,321 | B2 | 9/2009 | Cribier |
| 7,618,446 | B2 | 11/2009 | Andersen et al. |
| 7,785,366 | B2 | 8/2010 | Maurer et al. |
| 7,837,727 | B2 | 11/2010 | Goetz et al. |
| 7,959,661 | B2 | 6/2011 | Hijlkema et al. |
| 8,029,556 | B2 | 10/2011 | Rowe |
| 8,147,541 | B2 | 4/2012 | Forster et al. |
| 8,167,932 | B2 | 5/2012 | Bourang et al. |
| 8,337,541 | B2 | 12/2012 | Quadri et al. |
| 8,449,606 | B2 | 5/2013 | Eliasen et al. |
| 8,512,398 | B2 | 8/2013 | Alkhatib |
| 8,512,401 | B2 | 8/2013 | Murray, III et al. |
| 8,562,663 | B2 | 10/2013 | Mearns et al. |
| 8,562,673 | B2 | 10/2013 | Yeung et al. |
| 8,652,202 | B2 | 2/2014 | Alon et al. |
| 8,808,356 | B2 | 8/2014 | Braido et al. |
| 8,840,663 | B2 | 9/2014 | Salahieh et al. |
| 9,155,619 | B2 | 10/2015 | Liu et al. |
| 9,237,948 | B2 | 1/2016 | Colson et al. |
| 2002/0032481 | A1 | 3/2002 | Gabbay |
| 2003/0050694 | A1 | 3/2003 | Yang et al. |
| 2004/0133263 | A1 | 7/2004 | Dusbabek et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0080474 | A1 | 4/2005 | Andreas et al. |
| 2005/0096736 | A1 | 5/2005 | Osse et al. |
| 2005/0203614 | A1 | 9/2005 | Forster et al. |
| 2005/0203617 | A1 | 9/2005 | Forster et al. |
| 2006/0025857 | A1 | 2/2006 | Bergheim et al. |
| 2007/0005131 | A1 | 1/2007 | Taylor |
| 2007/0203575 | A1 | 8/2007 | Forster et al. |
| 2007/0265700 | A1 | 11/2007 | Eliasen et al. |
| 2008/0125853 | A1 | 5/2008 | Bailey et al. |
| 2008/0294230 | A1 | 11/2008 | Parker |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0319037 | A1 | 12/2009 | Rowe et al. |
| 2010/0023117 | A1 | 1/2010 | Yoganathan et al. |
| 2010/0049313 | A1 | 2/2010 | Alon et al. |
| 2010/0082089 | A1* | 4/2010 | Quadri .............. A61F 2/2418 623/1.11 |
| 2010/0191326 | A1 | 7/2010 | Alkhatib |
| 2010/0198347 | A1 | 8/2010 | Zakay et al. |
| 2010/0239142 | A1 | 9/2010 | Dannels et al. |
| 2011/0015729 | A1 | 1/2011 | Jimenez et al. |
| 2011/0264198 | A1 | 10/2011 | Murray, III et al. |
| 2011/0301702 | A1 | 12/2011 | Rust et al. |
| 2012/0123529 | A1 | 5/2012 | Levi et al. |
| 2012/0245676 | A1 | 9/2012 | Dierking et al. |
| 2013/0268064 | A1 | 10/2013 | Duffy |
| 2013/0310923 | A1 | 11/2013 | Kheradvar et al. |
| 2013/0317598 | A1 | 11/2013 | Rowe et al. |
| 2014/0067050 | A1 | 3/2014 | Costello et al. |
| 2014/0114392 | A1 | 4/2014 | McDonald et al. |
| 2014/0358224 | A1 | 12/2014 | Tegels et al. |
| 2015/0018939 | A1 | 1/2015 | Colson et al. |
| 2015/0112430 | A1 | 4/2015 | Creaven et al. |

FOREIGN PATENT DOCUMENTS

| | | |
|---|---|---|
| DE | 19907646 A1 | 8/2000 |
| EP | 0592410 B1 | 10/1995 |
| EP | 0701800 A1 | 3/1996 |
| EP | 0850607 A1 | 7/1998 |
| EP | 0990427 A2 | 4/2000 |
| EP | 1796597 A2 | 6/2007 |
| EP | 2522314 A1 | 11/2012 |
| FR | 2815844 A1 | 5/2002 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2004017868 A1 | 3/2004 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2009081396 A2 | 7/2009 |
| WO | 2010121076 A2 | 10/2010 |
| WO | 2012118508 A1 | 9/2012 |
| WO | 2013022798 A1 | 2/2013 |
| WO | 2013184945 A1 | 12/2013 |
| WO | 2014063039 A1 | 4/2014 |
| WO | 2014189977 A1 | 11/2014 |
| WO | 2015127283 A1 | 8/2015 |

OTHER PUBLICATIONS

Aamir Shah, MD, Facs, et al., "Endovascular Treatment of Aortic Dissections", Advances in Heart & Heart Surgery, Cedars-Sinai Heart Institute, Fall 2013, Los Angeles, CA, pp. 1-4.

John G. Webb et al., "Transcatheter Aortic Valve Implantation: The Evolution of Prostheses, Delivery Systems and Approaches", Archives of Cardiovascular Disease, 2012, pp. 153-159.

* cited by examiner

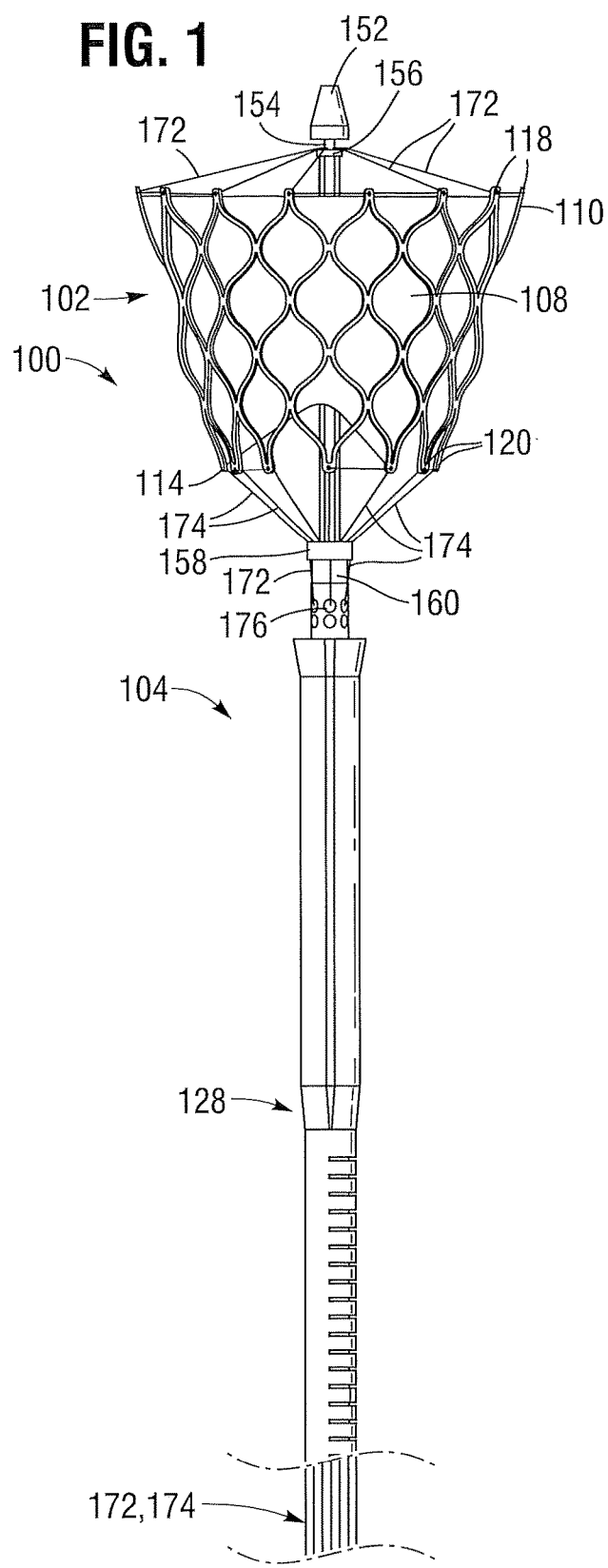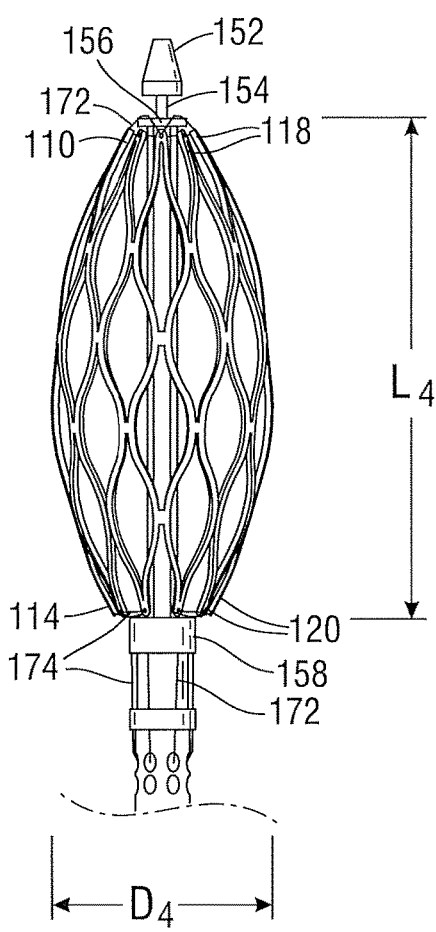
FIG. 1
FIG. 2

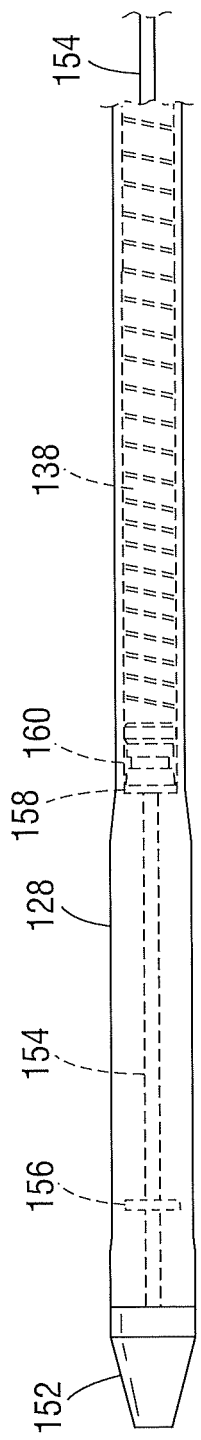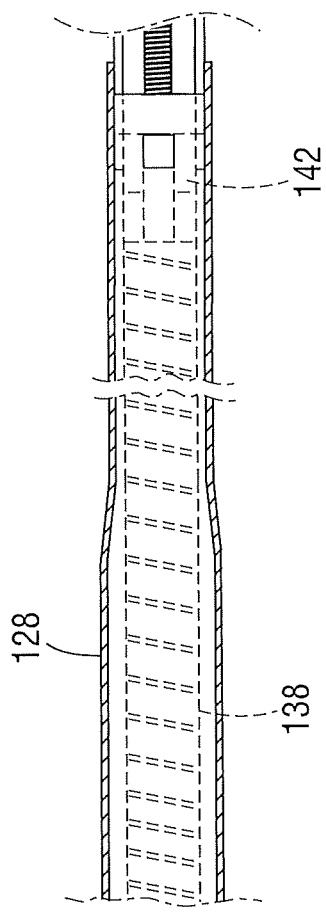
FIG. 7
FIG. 8

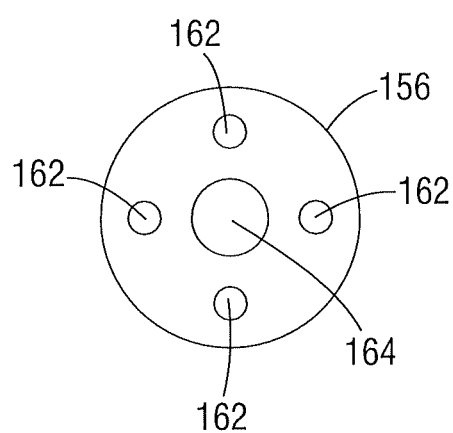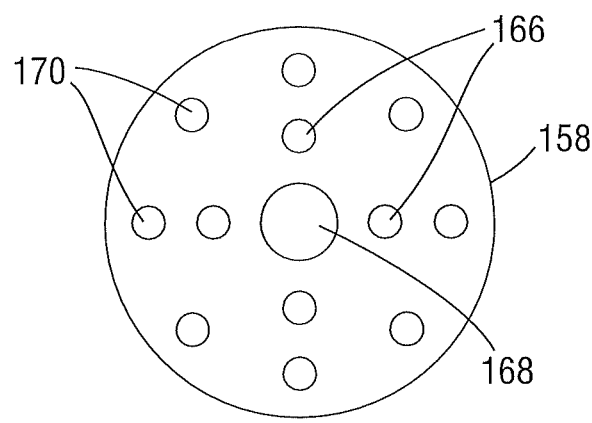

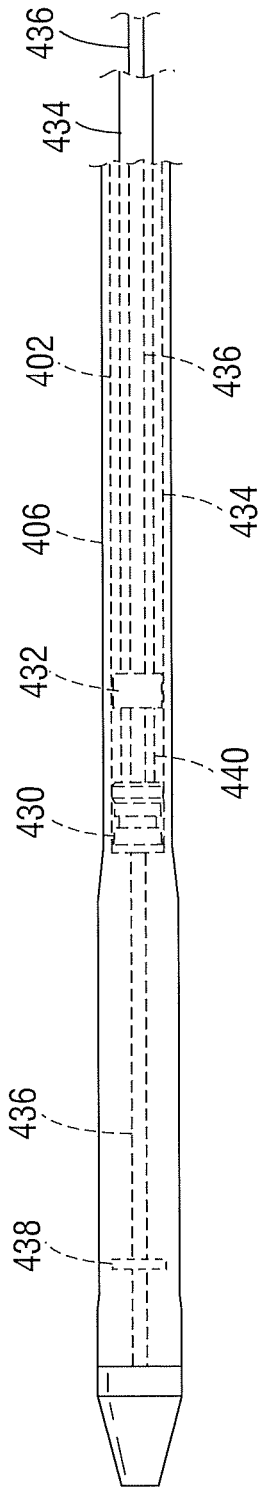
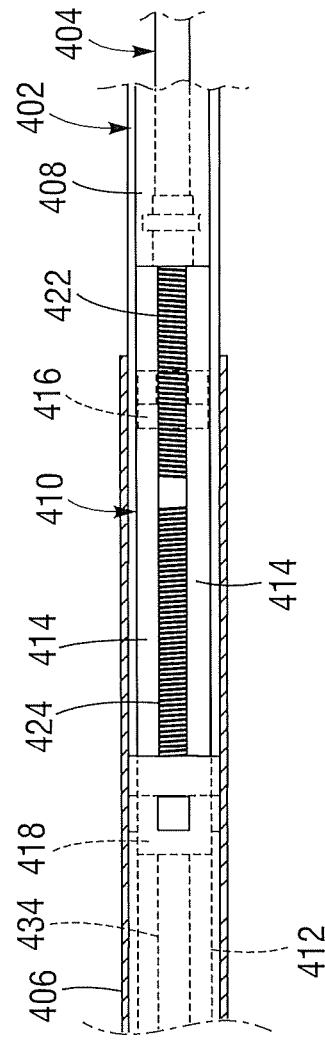
FIG. 18
FIG. 19

SUTURE DEPLOYMENT OF PROSTHETIC HEART VALVE

CROSS-REFERENCE TO RELATED APPLICATIONS

This application is a divisional of U.S. patent application Ser. No. 15/366,959, filed Dec. 1, 2016, which claims the benefit of U.S. Provisional Patent Application No. 62/262,307, filed Dec. 2, 2015, both of which are incorporated by reference herein.

FIELD

The present disclosure relates to implantable, expandable prosthetic devices and to methods and delivery assemblies for such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering intense attention. In one technique, a prosthetic device is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A challenge of implanting a self-expanding prosthetic valve via a catheterization is control of the expansion of the prosthetic valve as the prosthetic valve is deployed from a distal end of a delivery apparatus (i.e., the end of the apparatus that is advanced into a patient's heart) during the implantation procedure. Typically, a self-expanding prosthetic valve expands rapidly when it is exposed from a delivery cylinder or sheath. The rapid expansion can cause the prosthetic valve to migrate or "jump" from a desired deployment position within the patient's heart. As such, the prosthetic valve must subsequently be repositioned to the desired deployment position.

Another challenge of self-expandable prosthetic valves includes repositioning and/or retrieving the prosthetic valve once it is expanded to the functional size. Repositioning the prosthetic valve can be relatively more difficult in the expanded, functional state because the increased radial profile of the prosthetic valve can cause the prosthetic valve to engage the native anatomy (e.g., the native annulus) of the patient's heart, which can interfere or prevent the prosthetic valve from moving freely within the patient's heart. Retrieving the prosthetic valve can be relatively more difficult once the prosthetic valve is expanded because it can be difficult to exert sufficient radial force on the prosthetic valve to cause it to radially compress so that it can be retracted into a delivery cylinder.

An additional challenge is that about fifty percent of self-expanding prosthetic valves require a balloon post-dilation procedure to expand the prosthetic valve to its nominal diameter and/or to reduce paravalvular leakage. This additional procedure can add undesirable steps and thus time to an implantation procedure.

Thus, there is a continuing need for improved transcatheter prosthetic devices and delivery apparatuses for implanting such devices.

SUMMARY

Embodiments of improved prosthetic implant delivery assemblies are disclosed herein, as well as related methods, apparatuses, and devices for such assemblies. In several embodiments, the disclosed assemblies are configured for delivering replacement heart valves into a heart of a patient. The disclosed assemblies, apparatuses, and methods can, for example, improve a physician's ability to control the expansion, repositioning, and/or retrieval of a prosthetic implant during an implantation procedure.

In one representative embodiment, a delivery assembly comprises an annular stent having a first plurality of apices spaced circumferentially around a first end portion of the stent, a second plurality of apices spaced circumferentially around a second end portion of the stent, and an intermediate portion disposed between the first and the second end portions, wherein the stent is configured to radially expand and axially foreshorten from a first state to a second state and to radially compress and axially elongate from the second state to the first state, an elongate shaft disposed radially within and extending axially through the stent and having a first manifold coupled to the shaft distal to the first end of the stent, wherein the first manifold has a first plurality of openings, a second manifold located proximal to the first manifold of the shaft, wherein the second manifold has a second plurality of openings, a first plurality of sutures extending through at least some of the second openings of the second manifold, through the first openings of the first manifold, and through or around the first plurality of apices of the stent, wherein the first plurality of sutures is releasably coupled to the stent and configured such that increasing tension of the first plurality of sutures causes the first plurality of apices of the stent to radially converge, and a second plurality of sutures extending through at least some second openings of the second manifold and through or around the second plurality of apices of the stent, wherein the second plurality of sutures is releasably coupled to the stent and configured such that increasing tension of the second plurality of sutures causes the second plurality of apices of the stent to radially converge, wherein the intermediate portion of the stent can radially expand and axially foreshorten when the first and the second pluralities of apices radially converge.

In some embodiments, a sheath which can be advanced distally over the stent to retain the stent in the first state and retracted proximally relative to the stent to permit radial expansion of the stent from the first state to the second state, wherein after the entirety of the stent is deployed from the sheath, the first and the second plurality of apices of the stent can be radially converged, and the sheath can be advanced distally back over the stent to cause the stent to radially collapse to the first state as it is recaptured by the sheath.

In some embodiments, the first and the second plurality of sutures are configured to be independently movable relative to each other. In some embodiments, the second plurality of openings of the second manifold is an inner set of openings and an outer set of openings, the inner set of openings being spaced radially inward from the outer set of openings, and wherein the first plurality of sutures extend through the inner set of openings of the second manifold, and the second plurality of sutures extend through the outer set of openings of the second manifold.

In some embodiments, the shaft is a first shaft, and the delivery assembly further comprises a second shaft to which the second manifold is coupled. In some embodiments, the first shaft is a nose cone shaft which extends coaxially through the second shaft, and a nose cone is mounted on a distal end of the nose cone shaft. In some embodiments, the first manifold and the second manifold are configured to be axially movable relative to each other.

In some embodiments, the delivery assembly is configured such that increasing a spacing between the first manifold and the second manifold causes the intermediate portion of the stent to axially elongate and to radially compress. In some embodiments, the delivery assembly is configured such that decreasing the spacing between the first manifold and the second manifold causes the intermediate portion of the stent to axially foreshorten and to radially expand. In some embodiments, the stent is configured to be self-expandable from the first state to the second state. In some embodiments, the delivery assembly further comprises at least one apex guide mounted on a suture of the first plurality of sutures or the second plurality of sutures.

In another representative embodiment, a delivery apparatus for a prosthetic implant comprises an elongate first shaft, a first suture guide coupled to the first shaft, an elongate second shaft, and a second suture guide coupled to the second shaft, wherein the first shaft extends coaxially through the second shaft and the second suture guide, and the first suture guide is disposed distal to the second suture guide, and wherein the first suture guide and the second suture guide are configured to be axially movable relative to each other.

In some embodiments, the first shaft is a nose cone shaft. In some embodiments, the delivery apparatus further comprises a sheath, wherein the first and the second suture guides are disposed radially within the sheath when delivering the prosthetic implant to an implantation location, and the first and the second suture guides are exposed from the sheath when implanting the prosthetic implant at the implantation location.

In another representative embodiment, a method for delivering a prosthetic valve to a native annulus of a heart is provided. The method can comprise inserting an elongate delivery apparatus into a patient's body, advancing the delivery apparatus to an implantation location within the native annulus, retracting a delivery sheath of the delivery apparatus relative to the prosthetic valve to expose the prosthetic valve from a distal end of the delivery sheath, and after the prosthetic valve is exposed from the delivery sheath, expanding the prosthetic valve from a radially compressed state to a radially expanded state by reducing axial tension on first and second ends of the prosthetic valve.

In some embodiments, reducing axial tension on the first end of the prosthetic valve precedes reducing tension on the second end of the prosthetic valve. In some embodiments, reducing axial tension on the first end of the prosthetic valve and reducing tension on the second end of the prosthetic valve occur simultaneously.

In some embodiments, reducing axial tension on the first and second ends of the prosthetic valve comprises reducing tension on a plurality of sutures of the delivery apparatus. In some embodiments, reducing axial tension on the first and second ends of the prosthetic valve comprises moving a first manifold of the delivery apparatus axially proximally toward a second manifold of the delivery apparatus.

In some embodiments, the radially expanded state of the prosthetic valve is a first radially expanded state, and the method can further comprise expanding the prosthetic valve from the first radially expanded state to a second radially expanded state by radially converging the first and second ends of the prosthetic valve and axially compressing the first and second ends of the prosthetic valve by moving the first manifold of the delivery apparatus axially proximally toward the second manifold of the delivery apparatus, wherein the stent is radially larger in the second radially expanded state than in the first radially expanded state. In some embodiments, the method can further comprise radially compressing the prosthetic valve by moving the first manifold of the delivery apparatus axially distally away from the second manifold of the delivery apparatus.

In another representative embodiment, a delivery assembly comprises an annular frame and a delivery apparatus. The annular frame includes a first plurality of apices spaced circumferentially around a first end portion of the frame, a second plurality of apices spaced circumferentially around a second end portion of the frame, and an intermediate portion disposed between the first and the second end portions wherein the frame is configured to radially expand and axially foreshorten from a first state to a second state and to radially compress and axially elongate from the second state to the first state. The delivery apparatus includes an elongate shaft, a suture guide coupled to a distal end portion of the shaft, suture loops coupled to the suture guide, apex guides coupled to the suture loops, and a delivery cylinder that is coaxial and axially movable relative to the shaft, wherein the delivery cylinder is configured to retain the frame in the first state when the frame is disposed radially within the delivery cylinder, wherein the frame is releasably coupled to the suture guide by the suture loops which extend through respective apex guides and wrap around at least some of the first apices of the frame, wherein the apex guides are configured to prevent the first apices of the frame from snagging on a distal end of the delivery cylinder when the frame is in the second state and is being retrieved into the delivery cylinder.

The foregoing and other objects, features, and advantages of the invention will become more apparent from the following detailed description, which proceeds with reference to the accompanying figures.

BRIEF DESCRIPTION OF THE DRAWINGS

FIG. 1 is a plan view of a distal end portion of a prosthetic implant delivery assembly with a prosthetic heart valve in a radially expanded configuration, according to one embodiment.

FIG. 2 is a plan view of the distal end portion of the prosthetic implant delivery assembly with a stent of the prosthetic heart valve of in a partially radially compressed configuration.

FIG. 7 is a plan view of the distal end portion of the delivery apparatus.

FIG. 8 is a partial cross-sectional view of the delivery apparatus.

FIG. 9 is a plan view of a first manifold of the delivery apparatus.

FIG. 10 is a plan view of a second manifold of the delivery apparatus.

FIGS. 18-21C are various views another embodiment of a delivery apparatus.

DETAILED DESCRIPTION

Figure 3:
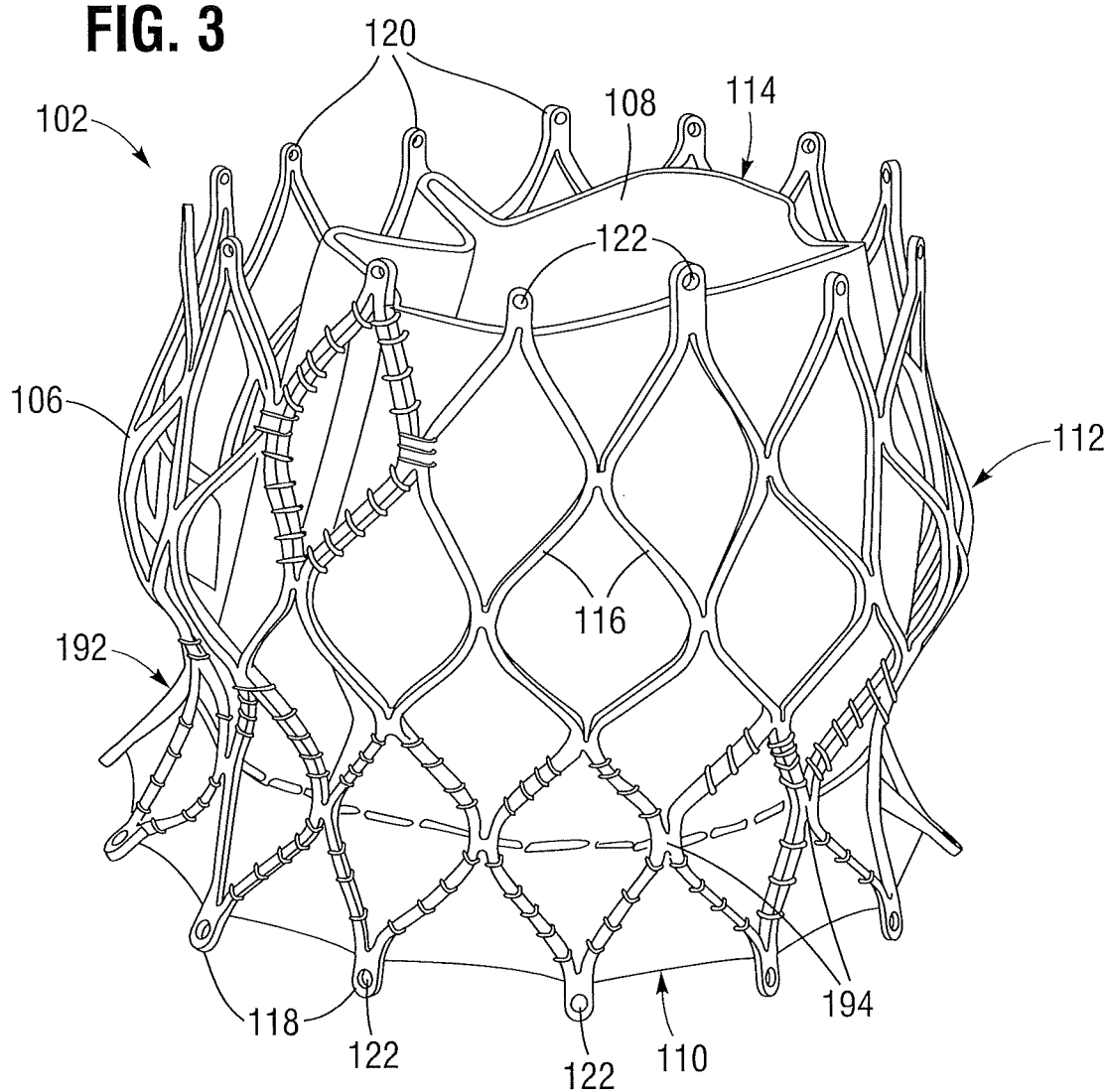
FIG. 3 is a perspective view of the prosthetic heart valve of the prosthetic implant delivery assembly of FIG. 1.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Embodiments of improved prosthetic implant delivery assemblies are disclosed herein, as well as related methods and devices for such assemblies. In several embodiments, the disclosed assemblies are configured for delivering replacement heart valves into a heart of a patient. The disclosed assemblies and methods can, for example, improve a physician's ability to control the expansion, repositioning, and/or retrieval of a prosthetic implant during an implantation procedure.

For example, in some embodiments, a delivery assembly (e.g., delivery assembly 100) can used to deliver a self-expandable prosthetic heart valve to a native annulus of a heart in a radially compressed state and can be configured such that a physician can control the expansion of the prosthetic heart valve when the prosthetic valve is deployed from within a delivery sleeve or sheath. In some embodiments, for example, a delivery assembly can be used to recapture and/or reposition a prosthetic heart valve that has been deployed with a native annulus of a heart.

In some embodiments, a delivery assembly (e.g., the delivery assembly 100) is adapted to deliver and implant a prosthetic heart valve in a native aortic annulus or valve of a heart (see, e.g., FIG. 9) using a retrograde approach, although in other embodiments it can be adapted to deliver and implant a prosthetic valve in the other native annuluses of the heart (e.g., the pulmonary, mitral, and tricuspid annuluses) and/or to be used with various other approaches (e.g., antegrade, transseptal, transventricular, transatrial, etc.).

A delivery assembly can also be adapted to deliver and implant a prosthetic valve in other tubular organs or passageways in the body. Further, in addition to prosthetic valves, a delivery assembly can be adapted to deliver and implant various other prosthetic devices such as stents and/or other prosthetic repair devices.

FIGS. 1-10 show an example of an embodiment of a delivery assembly 100. Referring first to FIG. 1, the delivery assembly 100 can comprise a prosthetic heart valve 102 which is releasably coupled to a delivery apparatus 104.

Referring now to FIG. 3, the prosthetic valve 102 can comprise an annular stent or frame 106 and a valve structure 108 which is coupled to the frame 106. The prosthetic valve 102 can have an inflow end portion 110, and intermediate portion 112, and an outflow end portion 114.

The frame 106 can comprise a plurality of interconnected struts 116 arranged in a lattice-type pattern and forming a first plurality of apices 118 and a second plurality of apices 120 at the respective inflow and outflow ends 110, 114 of the prosthetic valve 102. At least some of the apices 118, 120 can have a respective opening or aperture 122 formed therein (e.g., each apex 118, 120 has an aperture 122 in the illustrated embodiment). The apertures 122 can, for example, be used to releasably couple the prosthetic valve 102 to the delivery apparatus 104, as further explained below (see, e.g., FIG. 1).

The frame 106 can be made of any of various suitable plastically-expandable materials (e.g., stainless steel, etc.) or self-expanding materials (e.g., nickel titanium alloy ("NiTi"), such as nitinol) as known in the art. When constructed of a plastically-expandable material, the frame 106 (and thus the prosthetic valve 102) can be crimped to a radially collapsed or compressed configuration or state on a delivery catheter and then expanded inside a patient by an inflatable balloon or equivalent expansion mechanism to an expanded or functional state. When constructed of a self-expandable material, the frame 106 (and thus the prosthetic valve 102) can be crimped to a radially collapsed or compressed configuration and restrained in the collapsed configuration by insertion into a sheath or equivalent mechanism of a delivery catheter. Once inside the body, the prosthetic valve can be advanced from the delivery sheath, which allows the prosthetic valve to radially expand to its functional state (e.g., FIG. 3).

Further details regarding the collapsible transcatheter prosthetic heart valves, including the manner in which the valve structure 108 can be coupled to the frame 106 of the prosthetic valve 102 can be found, for example, in U.S. Pat. Nos. 6,730,118, 7,393,360, 7,510,575, 7,993,394, and 8,652,202, which are incorporated herein by reference in their entirety.

Figure 4:
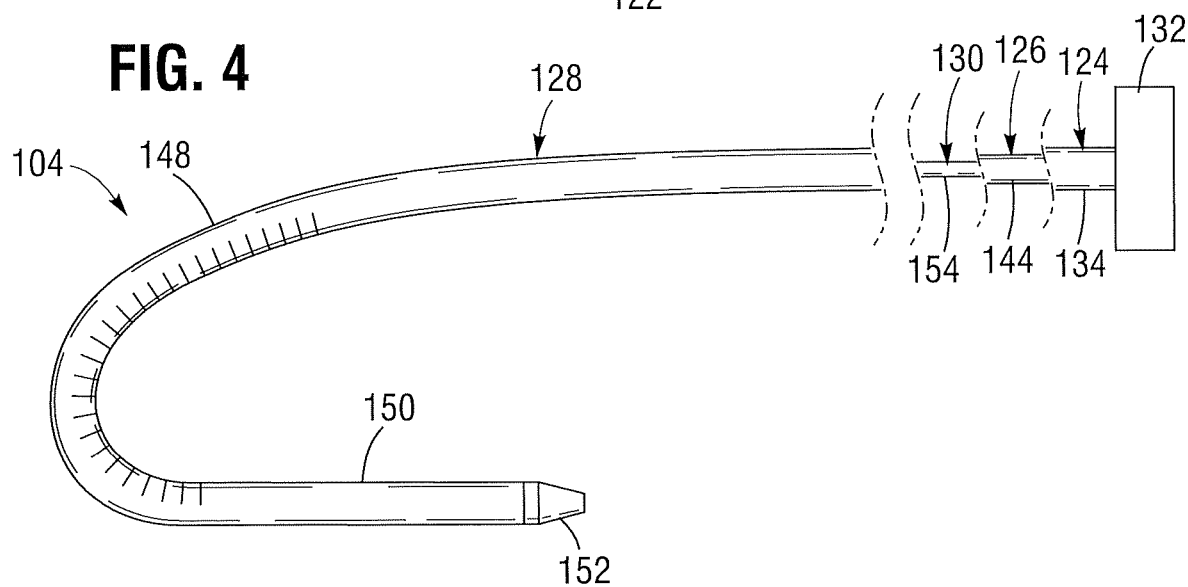
FIG. 4 is a partial plan view of a delivery apparatus of the prosthetic implant delivery assembly of FIG. 1.

Referring now to FIG. 4, the delivery apparatus 104 can generally comprise a first catheter 124, a second catheter 126 extending coaxially through the first catheter 124, a delivery cylinder 128 coupled to distal ends of the catheters 124, 126, and a guide-wire catheter 130 extending coaxially through the catheters 124, 126 and the delivery cylinder 128. The proximal ends of the catheters 124, 126, 130 can extend to and/or be coupled to a handle 132.

Figure 5:
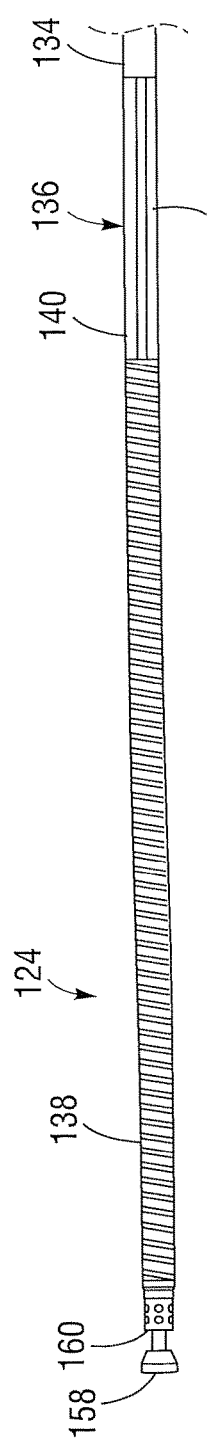
FIG. 5 is a plan view of a distal portion of a first catheter of the delivery apparatus.

As best shown in FIG. 5, the first catheter 124 can comprise an elongate shaft comprising a proximal shaft portion 134 extending distally from the handle 132, an intermediate portion 136 extending distally from the distal end of the proximal shaft 134, and a distal end portion 138 extending distally from the distal end of the intermediate portion 136. The intermediate portion 136 can comprise a plurality of a circumferentially spaced rails 140 extending axially from the proximal shaft 134 to the distal end portion 138. The rails 140 can be configured to engage a nut 142 (FIG. 6A) so as to prevent rotation of the nut 142 but allow axial movement or translation of the nut 142 upon rotation of the second catheter 126, as further described below. The distal end portion 138 can, for example, comprise a slotted tube to enhance the flexibility of the distal end portion 138 of the first catheter 124. The distal end portion 138 can, for example, be formed by laser-cutting a metal tube (e.g. a stainless steel or nitinol tube).

Figure 6A:
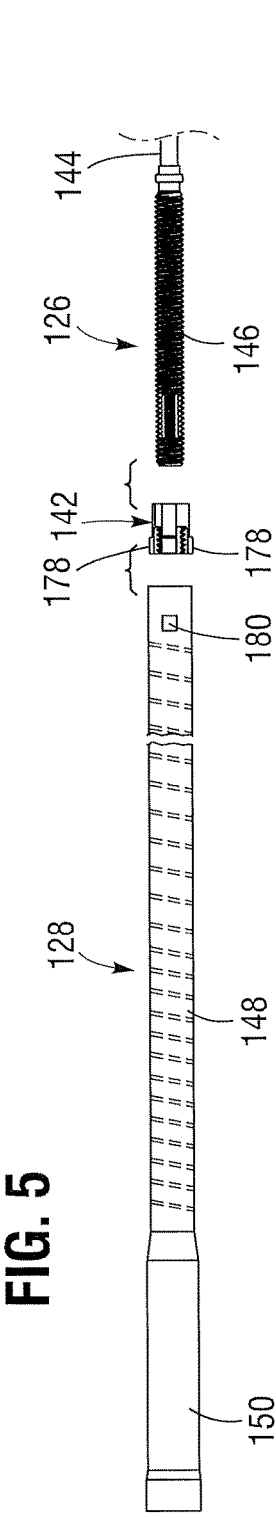
FIGS. 6A and 6B are exploded views of a second catheter and a delivery cylinder of the delivery apparatus.
Figure 6B:
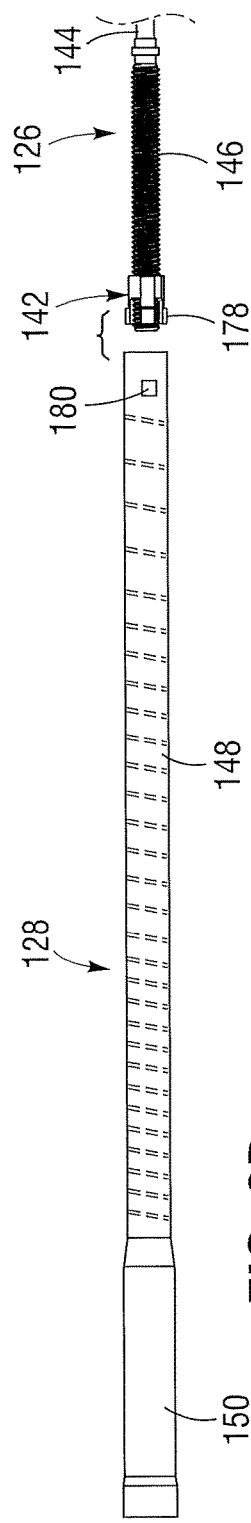
Figure 6C:
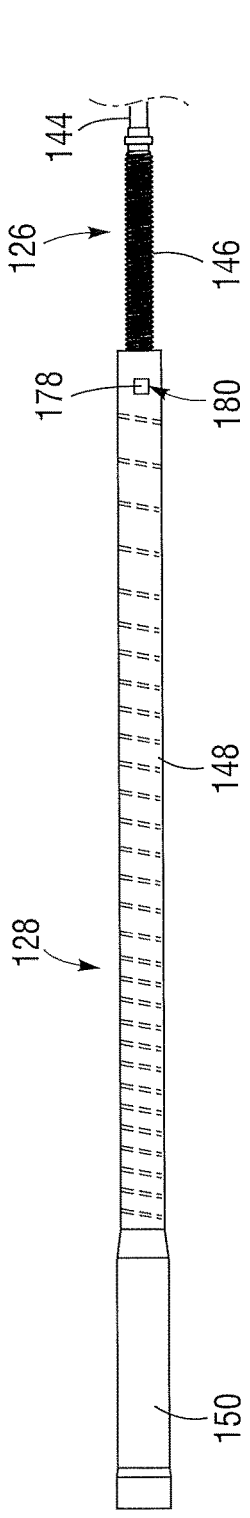
FIG. 6C is a plan view of the second catheter and the delivery cylinder of the delivery apparatus.

As best shown in FIGS. 6A-6C, the second catheter 126 can comprise an elongate shaft 144 (which can be referred to as a torque shaft) and a threaded member or screw 146 connected to the distal end of the torque shaft 144. The proximal end of the torque shaft 144 can be coupled to the handle 132, for example, by a coupling member (not shown). The threaded member can have external threads configured to engage corresponding internal threads of the nut 140. As such, the nut 142 can be mounted to the threaded member 146, as best shown in FIG. 6B.

Referring still to FIGS. 6A-6C, the delivery cylinder 128 can comprise a relatively more flexible proximal portion 148 and a relatively less flexible distal sheath portion 150 (which can be referred to as a sleeve or sheath). The proximal portion can comprise a slotted tube or cylinder (e.g., a metal tube) to enhance the flexibility of the proximal portion 148 of the delivery cylinder 128. The sheath 150 can be configured to extend over and retain a prosthetic valve in a radially compressed state during delivery of the prosthetic valve to an implantation location.

As best shown in FIGS. 1-2, the guide-wire catheter 130 can comprise a nose cone 152 connected to a distal end of a nose cone shaft 154. The nose cone shaft 154 can include a guide-wire lumen (not shown) for receiving a guide-wire (not shown) and can extend proximally to the handle 132 of the delivery apparatus 104.

Additional details regarding the regarding construction of the catheters 124, 126, 130 and delivery cylinder 128 can be found, for example, in U.S. Pat. No. 9,155,619 and U.S. Patent Application Publication No. 2014/0343670, which are incorporated herein by reference in their entirety.

The delivery apparatus 104 can further comprise a first, distal manifold or suture guide 156 and a second, proximal manifold or suture guide 158, as best shown in FIG. 1. As shown in the illustrated embodiment, the first manifold 156 can, for example, be coupled to the nose cone shaft 154 of the guide-wire catheter 130. The second manifold 158 can be coupled to the distal end of a suture retention member 160 which can be coupled to the distal end of the distal end portion 138 of the first catheter 124, as best shown in FIG. 5.

Referring now to FIGS. 9-10, the first manifold 156 can have a plurality of circumferentially spaced suture openings 162 (e.g., four in the illustrated embodiment) disposed radially outward from a centrally disposed lumen 164. The second manifold 158 can have a first, inner plurality of circumferentially spaced suture openings 166 (e.g., four in the illustrated embodiment) disposed radially outward from a centrally disposed lumen 168 and configured to radially and circumferentially align with the openings 162 of the first manifold 156. The second manifold can, optionally, have a second, outer plurality of circumferentially spaced suture openings 170 (e.g., eight in the illustrated embodiment) disposed radially outward from the inner openings 166.

Each plurality of openings 162, 166, 170 can, for example, comprise 2-20 openings. For example, in some embodiments, each plurality can comprise 4, 6, or 8 openings. In some embodiments, at least some of the pluralities of openings 162, 166, 170 can comprise the same number of openings. In other embodiments, at least some of the pluralities of openings 162, 166, 170 can comprise a different number of openings.

The first and the second manifolds 156, 158 can be used to releasably couple the prosthetic valve 102 to the delivery apparatus with sutures or wires. For example, as shown in FIG. 1, the inflow end 110 of the prosthetic valve 102 can be releasably coupled to the delivery apparatus 104 by a first plurality of suture loops 172, and the outflow end 114 of the prosthetic valve 102 can be releasably coupled to the delivery apparatus 104 by a second plurality of suture loops 174. The first and the second manifolds 156, 158 can also be used to control and/or manipulate the expansion and compression of the prosthetic valve 102 when the prosthetic valve is exposed from the delivery sheath 150, as further described below.

Each suture 172 can form a loop which extends distally from the handle 132 to the distal end of the delivery apparatus 104 and then proximally back to the handle 132. For example, each suture 172 can extend distally from the handle 132 and coaxially through the catheters 124, 126 and the suture retention member 160. Each suture 172 can exit the suture retention member through a respective radially extending port 176 (the port 176 extending radially from a lumen (not shown) of the suture retention member 160) at the proximal end of the suture retention member 160. Each suture 172 can then extend distally through a respective inner opening 166 of the second manifold 158, along the nose cone shaft 154 through the prosthetic valve 102, and through a respective opening 162 of the first manifold 156. Each suture loop 172 can then extend radially outward and circumferentially through at least one (three in the illustrated embodiment) opening 122 of an apex 118 at the inflow end 110 of the prosthetic valve 102. Each suture 172 can then extend radially inward and proximally through the respective opening 162 of the first manifold 156, along the nose cone shaft 154 through the prosthetic valve 102, through the respective inner opening 166 of the second manifold 158. Each suture 172 can then radially enter the suture retention member 160 through the respective port 176 and can extend coaxially through the suture retention member 160 and the first and the second catheters 124, 126 back to the handle 132.

Similarly, each suture 174 can form a loop which extends distally from the handle 132 to the distal end of the delivery apparatus 104 and then proximally back to the handle 132. For example, each suture 174 can extend distally from the handle and coaxially through the first and the second catheters 124, 126 and the suture retention member 160 and can radially exit the suture retention member 160 through a respective port 176. Each suture 174 can then extend distally through a respective outer opening 170 of the second manifold 158. Each suture 174 can then extend radially outward and circumferentially through at least one (two in the illustrated embodiment) opening 122 of an apex 120 at the outflow end 114 of the prosthetic valve 102. Each suture 174 can then extend radially inward and proximally through the respective outer opening 170 of the second manifold 158. Each suture 174 can then radially enter the suture retention member 160 through the respective port 176 and can extend coaxially through the suture retention member 160 and the first and the second catheters 124, 126 back to the handle 132.

Although the sutures 172, 174 are releasably coupled to the prosthetic valve 102 via the openings 122 in the apices 118, 120, it should be noted that the sutures 172, 174 can be releasably coupled to the respective inflow and outflow ends 110, 114 in various other ways. For example, the sutures 172, 174 can be releasably coupled to the prosthetic valve by wrapping the sutures 172, 174 around a respective apex 118, 120 of the prosthetic valve 102.

As best shown in FIGS. 7-8, when the delivery apparatus 104 is assembled, the torque shaft 144 of the second catheter 126 extends coaxially through the proximal shaft portion 134 of the first catheter 124, and the threaded member 146 of the second catheter 126 extends coaxially through the rails 140 of the first catheter 124. The nut 142 is mounted on the threaded member 146 and is connected to the proximal end portion of the delivery cylinder 128. The distal end portion 138 of the first catheter 124 extends coaxially through the delivery cylinder 128.

In this manner, the delivery cylinder 128 cooperates with the threaded member 146 and the nut 142 to allow for axial (i.e., proximal and/or distal) movement of the delivery cylinder 128 relative to the distal shaft portion 138 and the suture-retention member 160. Rotational motion of the threaded member 146 (initiated by the user rotating the torque shaft 144) can be converted into translational movement of the delivery cylinder 128 via the nut 142 positioned along external threads of the threaded member 146 (FIG. 6B). The nut 142 can further comprise one or more tabs 178 protruding radially outward, and the delivery cylinder 128 can comprise one or more windows or openings 180 adjacent a proximal end of the cylinder 128 for engaging the tabs 178. In particular, upper portions of the tab(s) 178 can extend through the openings(s) 180 to produce a secure fit (e.g., a snap fit) with the delivery cylinder 128.

As noted above, the first catheter 124 includes the intermediate section 136 that includes a plurality of circumferentially spaced rails 140, which cooperate with the tab(s) 178 of the nut 142. As best shown in FIG. 8, the threaded member 146 extends coaxially through the rails 140, and the nut 142 is disposed on the threaded member 146 with each tab 178 positioned in the space between two adjacent rails 140. Relative movement between the delivery cylinder 128 and the first catheter 124 occurs by rotating the torque shaft 144. Placement of the tab(s) 178 between the rails 140 prevents the nut 142 from rotating along with the threaded member 146. With rotation of the nut 142 restricted, rotation of the threaded member 146 produces translational or axial movement of the nut 142 along the threaded member 146. Axial movement of the nut 142 along the threaded member 146 (in the distal or proximal direction) causes the delivery cylinder 128 to also move axially in the same direction as the nut 142 (relative to the threaded member 146). Thus, as the nut 142 moves axially along the threaded member 146, the delivery cylinder 128 (connected to the nut 142 at the openings 180 via the tabs 178) is carried axially along-with the nut 142.

In the case of a threaded member 146 and a nut 142 with standard-type, right-handed threads, clockwise rotation of the threaded member 146 can result in proximal movement of the nut 142 along the threaded member 146. Conversely, counter-clockwise rotation of the standard threaded member 146 can result in distal movement of the nut 142. In this manner, rotation of the threaded member 146 can cause proximal or distal movement of the delivery cylinder 128 connected to the nut 142. Alternatively, the threads of the threaded member 146 can be reversed such that counter-clockwise rotation of the threaded member 146 causes proximal movement of the nut 142 and clockwise movement of the nut 142 causes distal movement of the nut 142.

FIG. 4 shows the delivery cylinder 128 advanced forward to its distal-most position for delivery. In the delivery configuration, the sheath 150 of the delivery cylinder 128 extends over the prosthetic valve (not shown), which is retained in a radially compressed state and releasably connected to the first and the second manifolds 156, 158 of the delivery apparatus 104 with the first and the second plurality of sutures 172, 174. The distal end of the sheath 150 can abut the nose cone 152 when the delivery cylinder 128 is in the delivery configuration.

FIG. 1 shows the delivery cylinder 128 retracted to a proximal position for deployment of the prosthetic valve 102. In the deployment configuration, the sheath 150 is retracted proximally past the first manifold 156, and the prosthetic valve 102, and the second manifold 158. When the frame 106 of the prosthetic valve 102 is formed from a self-expanding material, exposing the prosthetic valve 102 from within the sheath 150 of the delivery apparatus 104 allows the prosthetic valve 102 to partially radially expand, as shown in FIG. 2. In the partially radially expanded state, the apices 118, 120 at the inflow and the outflow ends 110, 114 of the prosthetic valve can remain radially compressed or converged via tension of the sutures 172, 174, but the intermediate portion 112 of the prosthetic valve 102 can radially expand. As a result, the prosthetic valve 102 comprises a generally elliptical shape in the partially expanded state.

The prosthetic valve 102 can then be fully expanded from the partially radially expanded state to the functional state by reducing tension on the sutures 172, 174, as shown in FIG. 1. The prosthetic valve 102 radially expands when exposed from within the sheath 150 and when tension is reduced on the sutures 172, 174 due to the outward biasing force of the prosthetic valve's self-expanding frame 106.

The delivery apparatus 104 can be configured such that the tension of the sutures 172, 174 can be independently adjusted or manipulated. For example, the tension on the sutures 172, 174 can be reduced slowly or gradually, which in turn causes the prosthetic valve 102 to slowly or gradually expand to it functional state. This can advantageously prevent the prosthetic valve 102 from migrating or "jumping" relative to a native annulus of a heart during expansion of the prosthetic valve during an implantation procedure.

The delivery apparatus 104 can also be configured such that the tension of the sutures 172 can be adjusted independently from the tension of the sutures 174, or vice versa. In this manner, the inflow and the outflow ends 110, 114 of the prosthetic valve can be radially expanded or compressed individually.

This can be accomplished, for example, by releasably connecting the sutures to one or more reels disposed at or adjacent to the handle 132. The reels can be configured to wind the sutures 172, 174 onto the reels, which foreshortens the sutures 172, 174, thus increasing the tension on the sutures 172, 174 and causing the inflow and outflow ends 110, 114 of the prosthetic valve to radially converge. The reels can be configured to unwind the sutures 172, 174 from the reels, which elongates the sutures 172, 174, thus reducing the tension on the sutures 172, 174 and allowing the prosthetic valve to radially expand.

When the prosthetic valve 102 is in the fully radially expanded state (e.g., FIG. 1), the prosthetic valve 102 can be repositioned and/or retrieved by increasing the tension on the first and/or the second plurality of sutures 172, 174 which causes the apices 118 and/or the apices 120 to radially converge to the partially radially expanded state (e.g., FIG. 2). In the partially radially expanded state, the prosthetic valve 102 can be repositioned relatively more easily than when the prosthetic valve 102 is in the fully radially expanded state because the prosthetic valve 102 at least partially disengages the native annulus, thereby allowing the prosthetic valve 102 to move relatively more easily within the native annulus. The prosthetic valve 102 can also be retrieved or retracted into the sheath 150 of the delivery apparatus 104 relatively more easily in the partially radially expanded state because the apices 118, 120 of the prosthetic valve 102 more easily fit within the sheath 150 when the apices 118, 120 radially converge. Thus, this state reduces the forces (e.g., axial and/or compressive) which are required to pull the prosthetic valve 102 back into sheath 150 or to push the sheath 150 back over the prosthetic valve 102.

Figure 11:
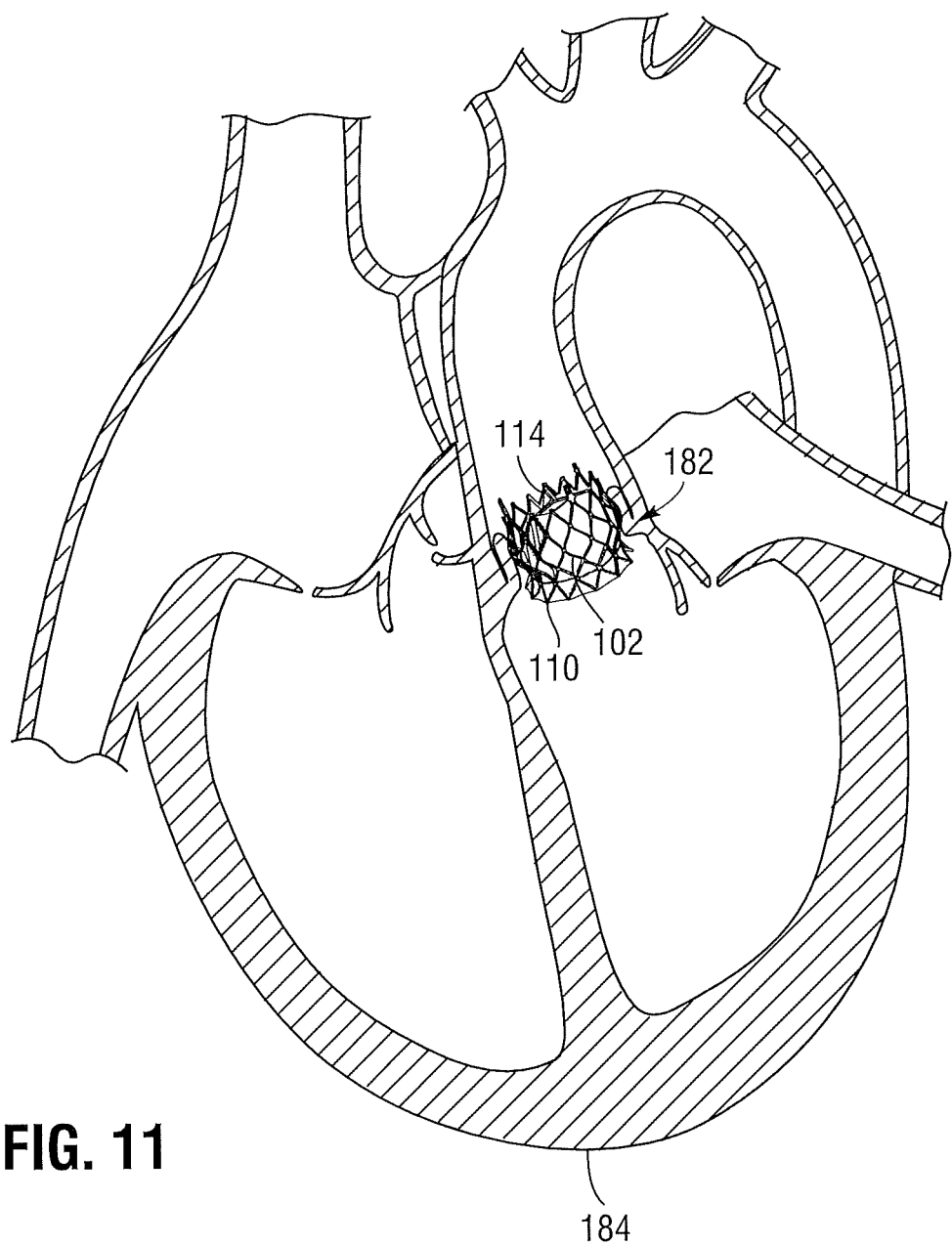
FIG. 11 is a perspective view of the prosthetic heart valve implanted in a native aortic annulus of a heart, shown in partial cross-section.

When the prosthetic valve 102 is desirably positioned with a native annulus, the prosthetic valve 102 can be fully radially expanded to its functional state, thus securing or allowing the prosthetic valve 102 to be secured within the native annulus. The prosthetic valve 102 can then be released from the delivery apparatus 104 by releasing the apices 118, 120 from the sutures. This can be accomplished by retracting the sutures 172, 174 from the openings 122 of the apices 118, 120, thereby disengaging the prosthetic valve 102 from the delivery apparatus. The delivery apparatus 104 can then be retracted proximally and removed from the patient's body, leaving the prosthetic valve 102 in the native annulus of the heart. For example, FIG. 11 shows the prosthetic valve 102 implanted within a native aortic annulus 182 a heart 184.

Figure 12:
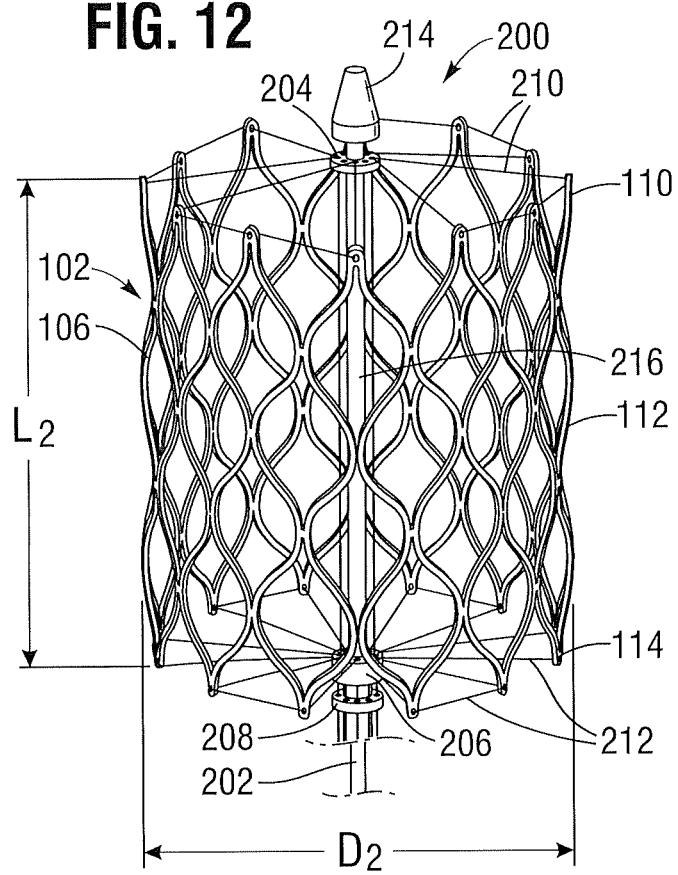
FIG. 12 is a perspective view of a distal end portion of a prosthetic implant delivery assembly with a stent in a radially expanded, functional configuration, according to another embodiment.
Figure 13:
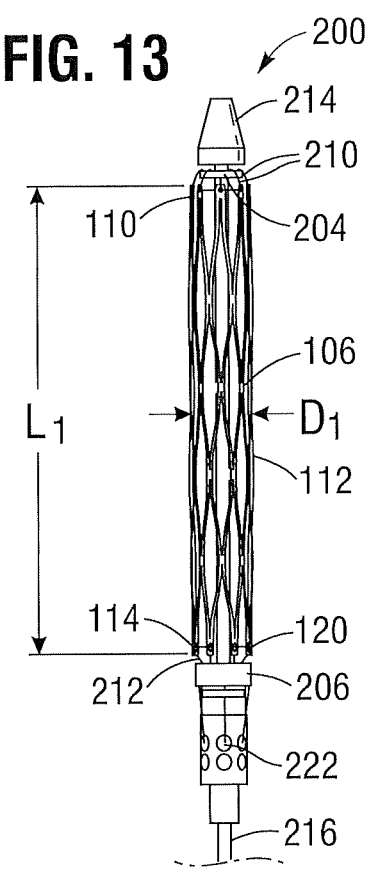
FIG. 13 is an elevation view of the distal end portion of the prosthetic implant delivery assembly with the stent in a radially compressed configuration.
Figure 14:
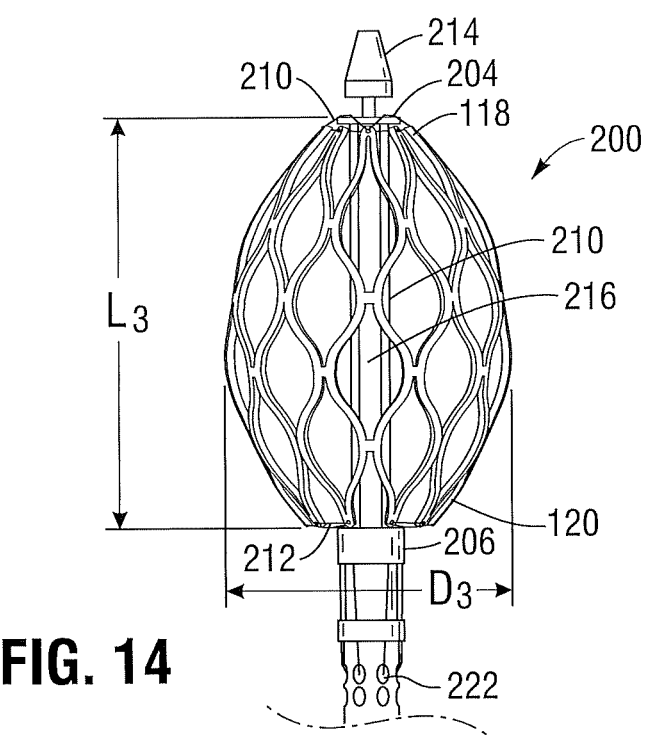
FIG. 14 is an elevation view of the distal end portion of the prosthetic implant delivery assembly with the stent in an axially compressed, radially expanded configuration.

FIGS. 12-14 show an example of another embodiment of a delivery apparatus 200, which is similar to the delivery apparatus 104. The delivery apparatus 200 can, for example, be a component of a delivery assembly comprising a prosthetic heart valve and the delivery apparatus 200. For example, FIGS. 12-14 show a delivery assembly comprising the prosthetic heart valve 102 and the delivery apparatus 200. For purposes of illustration, FIGS. 12-14 show only the frame 106 of the prosthetic valve 102 but omit other components of the prosthetic valve 102, such as the valve structure 108. The frame 106 is shown in FIG. 12 as being substantially cylindrical, however, it should be noted that the frame 106 can have a curved profile as shown in FIG. 3.

Although not shown, the delivery apparatus 200 can comprise a first catheter, a second catheter, a delivery cylinder, and a handle (e.g., similar to the first catheter 124, the second catheter 126, the delivery cylinder 128, and handle 132 of the delivery apparatus 104). The first and the second catheters and the delivery cylinder can be configured to cooperate in a manner similar to those of the delivery apparatus 104. For example, the delivery apparatus 200 can be configured such that rotating a rotatable torque shaft that extends coaxially through the first catheter causes a sheath that operatively coupled to a distal end of the torque shaft to retract or advance the sheath relative to a prosthetic valve, as described above with respect to delivery apparatus 104.

Referring to FIG. 12, the delivery apparatus 200 can further comprise a guide-wire catheter 202, a first suture manifold 204, a second suture manifold 206 connected to the distal end of a suture retention member 208, and first and second pluralities of sutures 210, 212. Each of these components, as well as their interaction together, is further described below.

The guide-wire catheter 202 can comprise a nose cone 214 connected to the distal end of a nose cone shaft 216, and an axially extending guide-wire lumen (not shown). The nose cone shaft 216 can extend distally from a handle and coaxially through the first and the second catheters, the delivery cylinder, the suture retention member 208, and the second manifold 206, and the first manifold 204. The nose cone shaft 216 can be configured to be independently axially (i.e., distally or proximally) moveable relative to the first and the second catheters, the delivery cylinder, the suture retention member 208, and the second manifold 206. This can be accomplished, for example, by forming a central lumen through the delivery apparatus 200 (or by forming a plurality of lumens which collectively form the central lumen) through which the nose cone shaft 216 axially extends.

The first suture manifold 204 can have a plurality of circumferentially spaced suture openings 218 (e.g., eight in the illustrated embodiment) disposed radially outward from a centrally disposed lumen (not shown, but see, e.g., lumen 164 (FIG. 9)). The first manifold 204 can be mounted on the distal end of the nose cone shaft 216, proximal to the nose cone 214.

The second manifold 206 can have a plurality of circumferentially spaced suture openings 220 (e.g., eight in the illustrated embodiment) disposed radially outward from a centrally disposed lumen (not shown, but see, e.g., lumen 168 (FIG. 10)) and configured to radially and circumferentially align with the openings 218 of the first manifold 204. Although not shown, the second manifold 206 can, optionally, have a second, outer plurality of circumferentially spaced suture openings (see, e.g., the openings 170 (FIG. 10)) disposed radially outward from the openings 220.

Each plurality of openings (e.g., 218, 220) can, for example, comprise 2-20 openings. For example, in some embodiments, each plurality can comprise 4, 6, or 8 openings. In some embodiments, at least some of the pluralities of openings can comprise the same number of openings. In other embodiments, at least some of the pluralities of openings can comprise a different number of openings.

As noted above, the second manifold 206 can be connected to the suture retention member 208. In some embodiments, the second manifold 206 and the suture retention member 208 can be connected by forming the second manifold 206 and the suture retention member 208 from separate pieces of material and connecting the pieces by a suitable means, such as welding, fasteners, and/or an adhesive. In other embodiments, the second manifold 206 and the suture retention member 208 can be connected by forming the second manifold 206 and the suture retention member 208 from a single, unitary piece of material.

The suture retention member 208 can mounted on the distal end of the first catheter (similar to the manner in which the suture retention member 160 is mounted on the distal end of the first catheter 124 (see, e.g., FIG. 5)). The suture retention member 208 can have a plurality of ports 222 each of which extend radially from an axially extending lumen (not show) which extends through the suture retention member 208, as best shown in FIG. 13.

Referring again to FIG. 12, the first and the second pluralities of sutures 210, 212 can be used to releasably couple the prosthetic valve 102 to the delivery apparatus 200. For example, the first plurality of sutures 210 can be used to releasably couple the inflow end 110 of the prosthetic valve 102 to the delivery apparatus 200, and the second plurality of sutures 212 can be used to releasably couple the outflow end 114 of the prosthetic valve 102 to the delivery apparatus 200.

The first and the second pluralities of sutures 210, 212 can also be used to control the expansion and/or compression of the inflow and the outflow ends 110, 114 of the prosthetic valve 102, as further described below. The first and the second pluralities of sutures 210, 212 can be configured to be independently adjustable and/or moveable relative to each other.

Each suture 210 can form a loop which extends distally from the handle to the distal end of the delivery apparatus 200 and then proximally back to the handle. For example, each suture 210 can extend distally from the handle and coaxially through the first and the second catheters and the suture retention member 208 and can radially exit the suture retention member 208 through a respective port 222. Each suture 210 can then extend distally through a respective opening 220 of the second manifold 206, along the nose cone shaft 216 through the prosthetic valve 102, and through a respective opening 218 of the first manifold 204. Each suture 210 can then extend radially outward and circumferentially through at least one (e.g., three in the illustrated embodiment) opening 122 of an apex 118 at the inflow end 110 of the prosthetic valve 102. Each suture 210 can then extend radially inward and proximally through the respective opening 218 of the first manifold 204, along the nose cone shaft 216 through the prosthetic valve 102, through the respective opening 220 of the second manifold 206. Each suture 210 can then radially enter the suture retention member 208 through the respective port 222 and can extend coaxially through the suture retention member 208 and the first and the second catheters back to the handle.

Similarly, each suture 212 can form a loop which extends distally from the handle to the distal end of the delivery apparatus 200 and then proximally back to the handle. For example, each suture 212 can extend distally from the handle and coaxially through the first and the second catheters and the suture retention member 208 and can radially exit the suture retention member 208 through a respective port 222. Each suture 212 can then extend distally through a respective opening 220 of the second manifold 206. Each suture 210 can then extend radially outward and circumferentially through at least one (two in the illustrated embodiment) opening 122 of an apex 120 at the outflow end 114 of the prosthetic valve 102. Each suture 210 can then extend radially inward and proximally through the respective opening 220 of the second manifold 206. Each suture 210 can then radially enter the suture retention member 208 through the respective port 222 and can extend coaxially through the suture retention member 208 and the first and the second catheters back to the handle.

In this manner, the sutures 210, 212 can be used to control the radial expansion or compression of the inflow and the outflow ends 110, 114 of the prosthetic valve 102. For example, when the prosthetic valve 102 is releasably coupled to the delivery apparatus 200 and exposed from within the sheath of the delivery apparatus 200, reducing tension on sutures 210, 212 allows the inflow and the outflow ends 110, 114 of the prosthetic valve 102 to radially diverge or expand from the radially converged or compressed state (e.g., FIG. 14) to the radially expanded, functional state (e.g., FIG. 12).

In addition, configuring the delivery apparatus 200 so that the guide-wire catheter 202 is axially moveable relative to other components of the delivery apparatus 200, such as the first and the second catheters, provides additional control and manipulation of the prosthetic valve 102. For example, in addition to being able to radially converge and/or expand the inflow and the outflow ends 110, 114 of the prosthetic valve 102, the intermediate portion 112 of the prosthetic valve 102 can be radially compressed and/or expanded by moving the nose cone shaft 204 axially (i.e., distally and/or proximally) relative to the first and the second catheters and/or by moving the first and second catheters relative to the nose cone shaft 204. Relative axial movement of the nose cone shaft 216 causes the first and the second manifolds 204, 206 to axially diverge or converge, thereby causing the intermediate portion 112 of the prosthetic valve 102 to axially elongate and radially compress or to axially foreshorten and radially expand.

For example, FIG. 13 shows the prosthetic valve 102 in the axially elongate, radially compressed state. This configuration can be achieved by increasing the tension on the sutures 210, 212, such that the inflow and the outflow ends 110, 114 of the prosthetic valve 102 radially converge, and then by advancing the nose cone shaft 216 distally such the first manifold 204 moves farther away from the second manifold 206 which applies axial tension on the inflow and the outflow ends 110, 114 of the prosthetic valve 102 and causes the intermediate portion 112 of the prosthetic valve 102 to axially elongate and radially compress. For example, in the axially elongate, radially compressed state (FIG. 13) the prosthetic valve 102 can have a length $L_1$ which is greater than a length $L_2$ of the prosthetic valve 102 in the relaxed, functional state (FIG. 12), and the prosthetic valve 102 can have a diameter $D_1$ which is less than a diameter $D_2$ of the prosthetic valve 102 in the relaxed, functional state. Thus, moving the manifolds 204, 206 away from each other causes the prosthetic valve 102 to axially elongate and radially compress while moving the manifolds 204, 206 toward each other allows the prosthetic valve 102 to axially foreshorten and radially expand.

The prosthetic valve 102 can be repositioned within a native annulus of a heart and/or retrieved into the sheath of the delivery apparatus 200 relatively more easily in the axially elongate, radially compressed state (FIG. 11) than in the radially expanded, functional state (FIG. 12).

When the prosthetic valve 102 is in the axially elongate, radially compressed state the prosthetic valve 102 can be expanded to the functional state by reducing tension on the prosthetic valve 102. This can be accomplished by reducing tension of the sutures 210, 212, which, due to the self-expanding biasing force of the prosthetic valve 102 attempting to reach its resting state, causes the first and the second manifolds 204, 206 to move closer together, thereby allowing the apices 118, 120 and the intermediate portion 112 of the prosthetic valve 102 to radially expand. Alternatively, the manifolds 204, 206 can be moved toward each other (e.g., by moving the nose cone shaft 216 proximally relative to the first catheter) while maintaining tension on the sutures 210, 212, allowing the intermediate portion 112 of the prosthetic valve 102 to radially expand while retaining the ends of the prosthetic valve 102 in the radially compressed state such that the prosthetic valve 102 attains the partially expanded state of FIG. 2.

In the partially expanded state of FIG. 2 (the ends of the prosthetic valve 102 are radially compressed, but the prosthetic valve 102 is not axially elongated), the prosthetic valve 102 has an outer diameter $D_4$ and a length $L_4$. With the prosthetic valve 102 in the partially expanded state, the delivery apparatus 200 can also be used to mechanically radially expand the prosthetic valve 102 beyond the partially expanded state, as shown in FIG. 14. This can be accomplished by moving the manifolds 204, 206 toward each other (e.g., moving the first manifold 204 proximally toward the second manifold 206 and/or moving the second manifold 206 distally toward the first manifold 204). This causes the first and the second manifolds 204, 206 to axially compress the prosthetic valve 102 such that an axial length $L_3$ of the prosthetic valve 102 is less than the axial length $L_1$ and $L_4$, thereby causing the intermediate portion 112 of the prosthetic valve 102 to radially expand such that a diameter $D_3$ of the prosthetic valve 102 is greater than the diameter $D_4$. The prosthetic valve 102 can be further axially compressed to further radially expand to a diameter $D_3$ which is greater than the diameter $D_2$.

In some embodiments, the delivery apparatus 200 can be used to mechanically radially expand the prosthetic valve 102 without first converging the ends of the prosthetic valve 102. For example, with the prosthetic valve 102 in the functional state (e.g., FIG. 12), the manifolds 204, 206 can be moved toward each other (e.g., moving the first manifold 204 proximally toward the second manifold 206 and/or moving the second manifold 206 distally toward the first manifold 204). This causes the first and the second manifolds 204, 206 to axially compress the prosthetic valve 102 such that an axial length of the prosthetic valve 102 is less than the axial length $L_2$, thereby causing the intermediate portion 112 of the prosthetic valve 102 to radially expand such that a diameter of the prosthetic valve 102 is greater than the diameter $D_2$.

Allowing a physician to force the prosthetic valve to radially expand beyond itself self-expanded state by using the delivery apparatus 200 provides several significant advantages. For example, oftentimes a native annulus applies a sufficient radial force to the prosthetic valve such the prosthetic valve will not fully radially expand to a desired diameter under its own self-expanding force when deployed within the native valve annulus. This can result in decreased efficiency for the prosthetic valve and/or undesired paravalvular leakage. These problems can be particularly prevalent in native annuluses with stenosis and/or calcification. Such cases typically require a balloon post-dilation procedure to further expand the prosthetic valve to the desired diameter after the initial implantation. Alternatively, the delivery apparatus 200 can be used apply a sufficient axially compressive force to the prosthetic valve 102, which causes the prosthetic valve to radially expand (similar to a balloon) and dilate the annulus such that when the compressive force is removed from the prosthetic valve 102, the prosthetic valve has a resting diameter which is closer to the desired final functional diameter. Thus, the delivery apparatus 200 can advantageously improve the efficiency and paravalvular leakage. The delivery apparatus 200 can also advantageously reduce procedural times by reducing or eliminating the need for a balloon post-dilation procedure.

For example, in one particular embodiment, a prosthetic valve having a nominal expanded diameter of about 29 mm might expand under its own resiliency to a diameter of about 26.2 mm when deployed in a calcified native annulus. The delivery apparatus 200 can be used to further radially expand the prosthetic valve and further dilate the annulus by applying an axially compressive force to the prosthetic valve (see, e.g., FIG. 14) such that the prosthetic valve has a diameter of about 30 mm while under axial compression from the delivery apparatus 200. When the axially compressive force of the delivery apparatus 200 is removed, the prosthetic valve can relax to a diameter of 28 mm. Thus, the delivery apparatus 200 can advantageously increase the resting diameter of the prosthetic valve by 1.8 mm without requiring a balloon post-dilation procedure.

Figure 15:
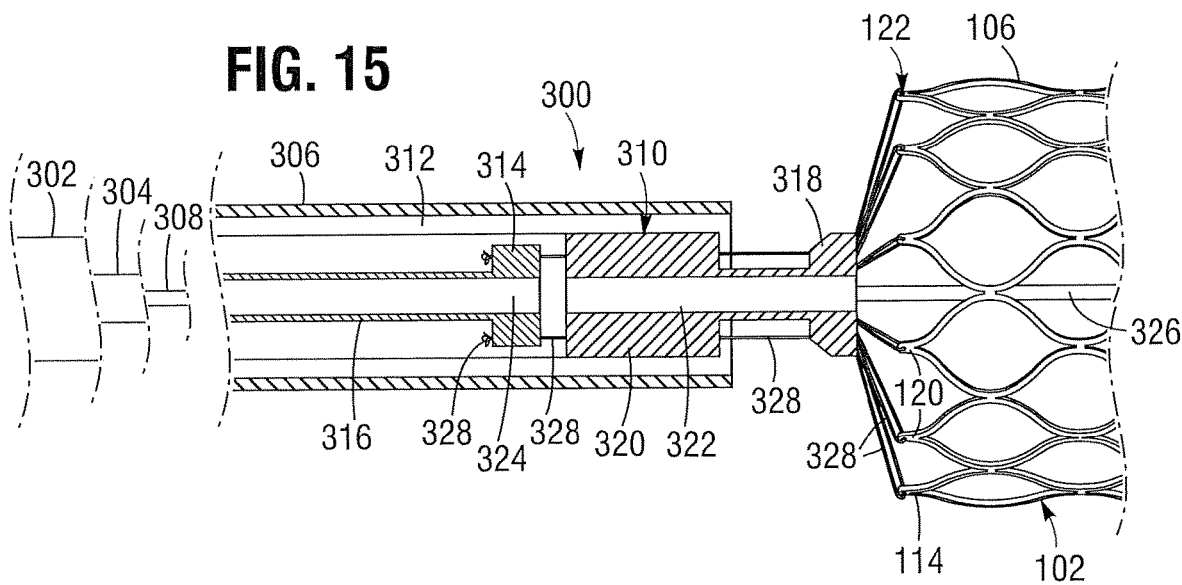
FIGS. 15-17 are various cross-sectional views of a delivery apparatus and plan views of a stent of a delivery assembly, according to another embodiment.
Figure 16:
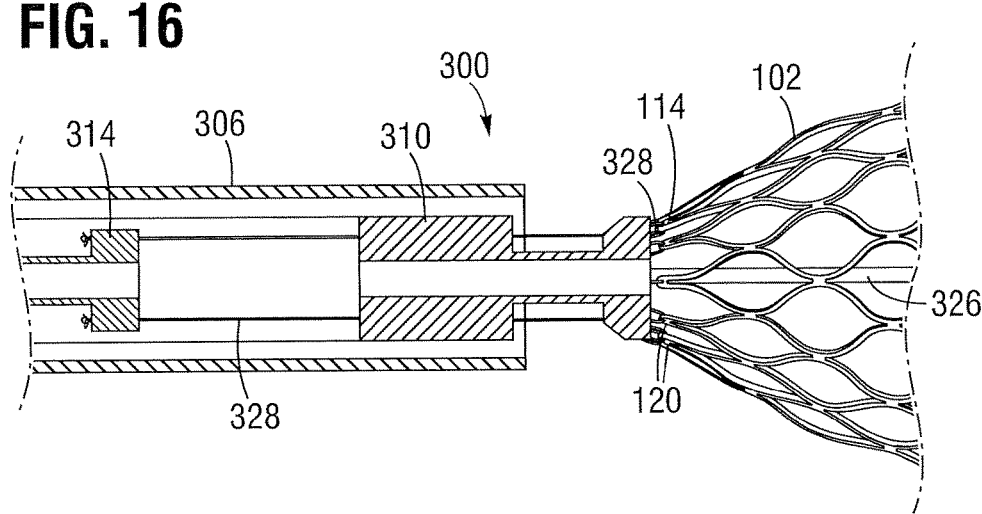
Figure 17:
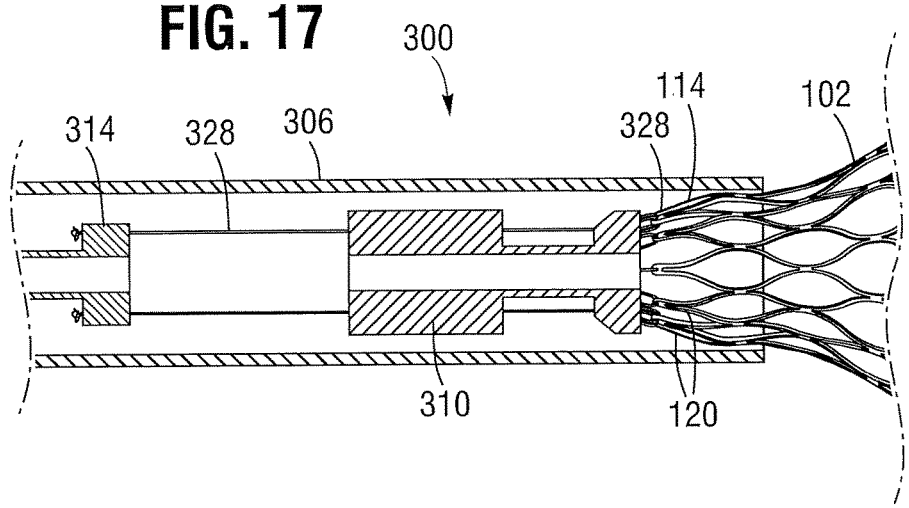

FIGS. 15-17 show an example of another embodiment of a delivery apparatus 300. The delivery apparatus 300 can, for example, be a component of a delivery assembly comprising a prosthetic heart valve (e.g., the prosthetic valve 102) and the delivery apparatus 300. For purposes of illustration, FIGS. 15-17 show only the frame 106 of the prosthetic valve 102 but omit other components of the prosthetic valve 102, such as the valve structure 106.

Referring now to FIG. 15, the delivery apparatus 300 can comprise a first catheter 302, a second catheter 304 extending coaxially through the first catheter 302, a delivery cylinder 306 coupled to distal ends of the catheters 302, 304, and a guide-wire catheter 308 extending coaxially through the catheters 302, 304 and the delivery cylinder 306. The proximal ends of the catheters 302, 304, 308 can extend to and/or be coupled to a handle (not shown, but see, e.g., the handle 132). The catheters 302, 304, 308 can be independently moveable relative to each other. The delivery cylinder 306 can be an extension of a separate shaft that extends coaxially over the first catheter from the handle.

The delivery apparatus 300 can also comprise a suture retention member 310 secured or coupled to a distal end of an elongate shaft portion 312 of the first catheter 302, and a suture tensioning member 314 which is coupled to a shaft 316. The suture tensioning member 314 can be disposed proximally relative to the suture retention member 310. The shaft 316 can extend axially proximally from the suture tensioning member 314 to the handle. In some embodiments, the shaft 316 can be a shaft portion of the second catheter 304, or alternatively, the shaft 316 can be a pull wire extending from the handle to the suture tensioning member 314.

The suture retention member 310 can comprise a manifold portion 318 at the distal end and a proximal end portion 320 disposed proximally relative to the manifold 318. The suture member 310 can have a plurality of openings (not shown) which axially extend through the manifold 318 and the proximal end portion 320. The openings can be circumferentially spaced and can be disposed radially outward from a centrally disposed lumen 322 which extends axially through the suture retention member 310 and allows a nose cone shaft 326 of the guide-wire catheter 308 to axially extend through the suture retention member 310.

In some embodiments, the manifold 318 of the suture retention member 310 can be a second manifold (similar to the second manifold 158) releasably coupled to the proximal end of a prosthetic valve, and the delivery apparatus 300 can comprise a first manifold (similar to the first manifold 156) mounted on the distal end of the nose cone shaft 326 and releasably coupled to the distal end of the prosthetic valve in the manner shown in FIG. 1.

The suture tensioning member 314 can comprise a plurality of axially extending openings (not shown). The openings can be circumferentially spaced and can be disposed radially outward from a centrally disposed lumen 324 which extends axially through the suture retention member 310 and allows the nose cone shaft 326 of the guide-wire catheter 308 to axially extend through the suture tensioning member 314.

The respective openings of the suture retention member 310 and the suture tensioning member 314 can be used to releasably couple the prosthetic valve 102 to the delivery apparatus 300 via a plurality of sutures 328. For example, each suture 328 can form a loop which extends axially distally from a proximal end of the suture tensioning member 314, through a respective opening of the suture tensioning member 314, through a respective opening of the suture retention member 310, and to the outflow end 114 of the prosthetic valve 102. The loop can then extend radially through a respective aperture 122 of the prosthetic valve 102. The loop can then extend proximally from the outflow end 114 of the prosthetic valve 102, through the respective opening of the suture retention member 310, through a respective opening of the suture tensioning member 314, and to the proximal end of the suture tensioning member 314.

As such, the suture retention member 310 and the suture tensioning member 314 can be used to control the tension of the sutures 328, and thus, to control the radial expansion of prosthetic valve 102 when the prosthetic valve 102 is exposed from within the delivery cylinder 306. For example, as shown in FIG. 15, moving the suture tensioning member 314 distally relative to the suture retention member 310 lengthens the portions of the sutures 328 that are disposed between the suture retention member 310 and the prosthetic valve 102, which decreases tension on the sutures 328 and allows the apices 120 of the outflow end 114 of the prosthetic valve 102 to radially expand. This can be accomplished, for example, by moving the shaft 316 distally or slowly releasing a restraining force on the shaft 316 which allows the self-expanding force of the prosthetic valve to pull the suture tensioning member 314 distally toward the suture retention member 310.

As shown, for example, in FIG. 16, moving the suture tensioning member 314 proximally relative to the suture retention member 310 foreshortens the portions of the sutures 328 that are disposed between the suture retention member 310 and the prosthetic valve 102, which increases tension on the sutures 328 and causes the apices 120 of the outflow end 114 of the prosthetic valve 102 to radially converge. This can be accomplished, for example, by pulling on the shaft 316 which moves the suture tensioning member 314 proximally, away from the suture retention member 310.

Converging the apices 120 of the prosthetic valve 102 can, for example, allow the prosthetic valve to be relatively more easily moveable within a native annulus of a patient and/or more easily retrievable into the delivery apparatus 300. For example, as shown in FIG. 17, the delivery cylinder 306 can be advanced distally over the prosthetic valve 102 or the prosthetic valve 102 can be retracted proximally into the delivery cylinder 306.

The sutures 328 can be configured such that the loops can be retracted from the apertures 122 of the prosthetic valve 102 to release the prosthetic valve 102 from the delivery apparatus 300. This can be accomplished, for example, by releasably coupling the sutures 328 to the suture tensioning member 314 by a release wire (not shown). Additional details regarding releasably coupling a prosthetic valve to a delivery apparatus, including by a release wire can be found, for example, in U.S. Patent Application Publication No. 2014/0343670.

FIGS. 18-21C show an example of another embodiment of a delivery apparatus 400, which is similar to the delivery apparatus 300. The delivery apparatus 300 can, for example, be a component of a delivery assembly comprising a prosthetic heart valve and the delivery apparatus 400.

Referring to FIGS. 18-19, the delivery apparatus 400 can comprise a first catheter 402, a second catheter 404 extending coaxially through the first catheter 402, a delivery cylinder 406 coupled to distal ends of the catheters 402, 404, and a guide-wire catheter 436 (which can be called a nose cone catheter) extending coaxially through the catheters 402, 404 and the delivery cylinder 406. The proximal ends of the catheters 402, 404, 436 can extend to and/or be coupled to a handle (not shown, but see, e.g., the handle 132). The catheters 402, 404, 436 can be independently moveable relative to each other.

The delivery apparatus 400 can further comprise a suture retention member 430 coupled to the distal end of the first catheter 402 and a suture tensioning member 432 disposed proximal to the suture retention member 430 and coupled to the second catheter 204. In some embodiments, a distal suture manifold or suture guide 438 can be mounted on the distal end of the nose-cone catheter 436 for coupling the distal end of a prosthetic valve to the delivery apparatus as shown in FIG. 18.

Figure 20:
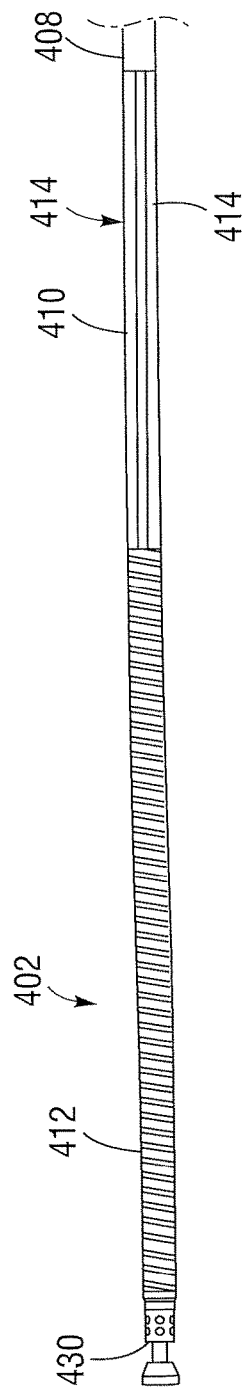

Referring to FIG. 20, the first catheter 402 (similar to the first catheter 124) can comprise an elongate proximal shaft portion 408 extending distally from the handle, an intermediate portion 410 extending distally from the distal end of the proximal shaft 408, and a distal end portion 412 extending distally from the distal end of the intermediate portion 410. The intermediate portion 410 can comprise a plurality of a circumferentially spaced rails 414 extending axially from the proximal shaft 408 to the distal end portion 412. The rails 414 can be configured to engage a proximal nut 416 and a distal nut 418 (FIG. 21A) so as to prevent rotation of the nuts 416, 418 but allow axial movement or translation of the nuts upon rotation of the second catheter 404, as further described below.

Figure 21A:
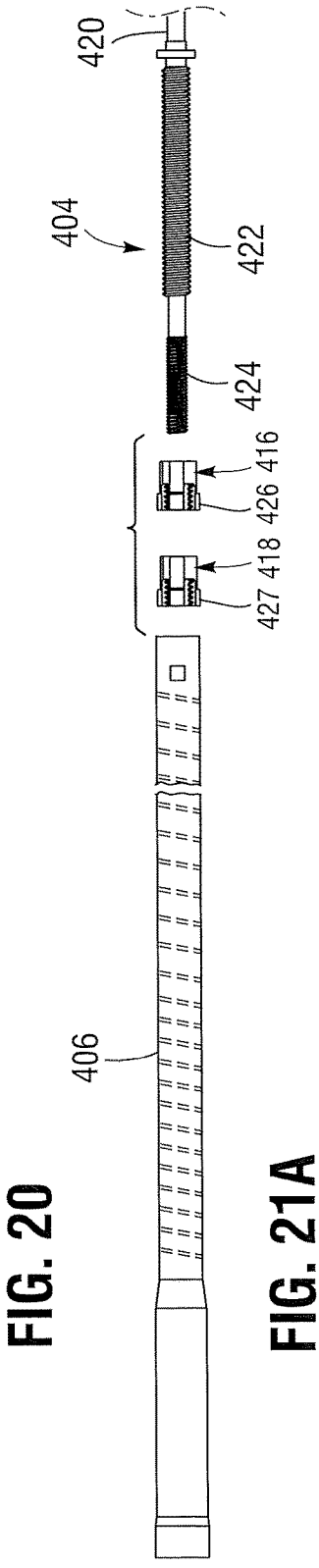
Figure 21B:
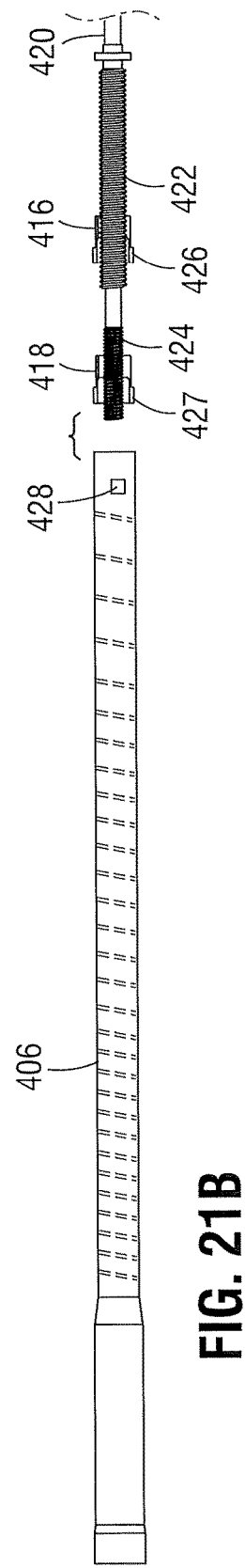
Figure 21C:
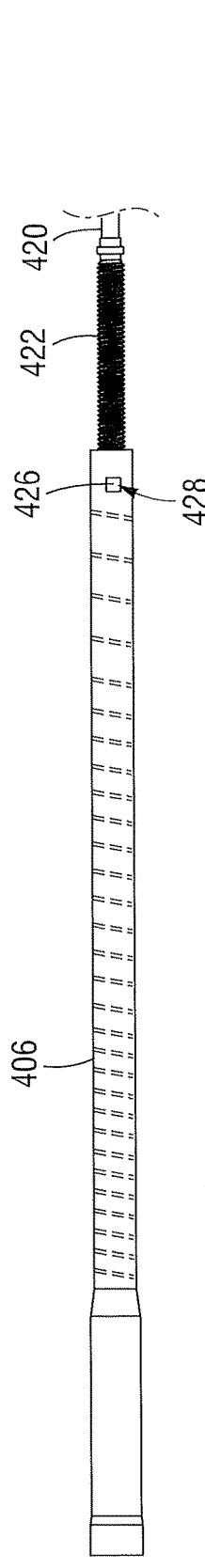

As best shown in FIGS. 21A-21C, the second catheter 404 can comprise an elongate proximal shaft 420 (which can be referred to as a torque shaft), a proximal threaded member or screw 422 connected to a distal end of the torque shaft 420, and a distal threaded member or screw 424 connected to a distal end of the proximal threaded member 422. In some embodiments, the threaded members 422, 424 can be connected to each other, for example, by forming the threaded members 422, 424 from a single, unitary piece of material. In other embodiments, the threaded members 422, 424 can be connected to each other, for example, by forming the threaded members 422, 424 from separate pieces of material which are connected by welding, an adhesive, etc. The proximal end of the torque shaft 420 can be coupled to the handle, for example, by a coupling member (not shown).

The proximal threaded member 422 can have external threads configured to engage corresponding internal threads of the proximal nut 416. As such, the proximal nut 416 can be mounted to the proximal threaded member 422, as best shown in FIG. 21B. As also best shown in FIG. 21B, the nut 416 can further comprise one or more tabs 426 protruding radially outward, and the delivery cylinder 406 can comprise one or more windows or openings 428 adjacent a proximal end of the delivery cylinder 406 for engaging the tabs 426. In particular, upper portions of the tab(s) 426 can extend through the openings(s) 428 to produce a secure fit (e.g., a snap fit) with the delivery cylinder 406.

The distal threaded member 424 can have external threads configured to engage corresponding internal threads of the distal nut 418. As such, the distal nut 418 can be mounted to the distal threaded member 424, as best shown in FIG. 21B. As best shown in FIG. 21B, the nut 418 can comprise one or more tabs 427 protruding radially outward, which are configured to engage the rails 414 of the first catheter 402.

Referring again to FIG. 19, when the delivery apparatus 400 is assembled, the torque shaft 420 of the second catheter 404 extends coaxially through the proximal shaft 408 of the first catheter 404, and the threaded members 422, 422 of the second catheter 404 extend coaxially through the rails 414 of the first catheter 402. The proximal nut 416 is mounted on the proximal threaded member 422 and is connected to the proximal end portion of the delivery cylinder 406. The distal nut 418 is mounted on the distal threaded member 424 and is coupled to the suture tensioning member 432 (e.g., via a shaft 434). The distal end portion 412 of the first catheter 404 extends coaxially through the delivery cylinder 406. In some embodiments, the shaft 434 can be an extension of the nut 418 or the second catheter 404.

As noted above, the first catheter 402 includes the intermediate section 410 that includes a plurality of circumferentially spaced rails 414, which cooperate with the tab(s) 426, 427 of the nuts 416, 418. As best shown in FIG. 19, the threaded members 422, 424 extend coaxially through the rails 414, and the nuts 416, 418 are disposed on respective threaded members 422, 424 with each tab 426 positioned in the space between two adjacent rails 414.

As such, relative movement between the delivery cylinder 406 and the first catheter 406 can be effectuated by rotating the torque shaft 420. Placement of the tab(s) 426 between the rails 414 prevents the proximal nut 416 from rotating along with the proximal threaded member 422. With rotation of the proximal nut 416 restricted, rotation of the proximal threaded member 422 produces translational or axial movement of the proximal nut 416 along the proximal threaded member 422. Axial movement of the proximal nut 416 along the proximal threaded member 422 (in the distal or proximal direction) causes the delivery cylinder 406 to also move axially in the same direction as the proximal nut 416 (relative to the proximal threaded member 422). Thus, as the proximal nut 416 moves axially along the proximal threaded member 422, the delivery cylinder 406 (which is connected to the proximal nut 416 at the openings 428 via the tabs 426) is carried axially along-with the proximal nut 416.

Similarly, relative movement between the suture retention member 430 and the suture tensioning member 432 can be effectuated by rotating the torque shaft 420. Placement of the tab(s) 427 between the rails 414 prevents the distal nut 418 from rotating along with the distal threaded member 424. With rotation of the distal nut 418 restricted, rotation of the distal threaded member 424 produces translational or axial movement of the distal nut 418 along the distal threaded member 424. Axial movement of the distal nut 418 along the distal threaded member 424 (in the distal or proximal direction) causes the shaft 434 and, thus, the suture tensioning member 432 to also move axially in the same direction as the distal nut 418 (distal threaded member 424). Thus, as the distal nut 418 moves axially along the distal threaded member 424, the suture tensioning member 432 is carried axially along-with the distal nut 418, thereby moving the suture tensioning member 432 relative to the suture retention member 430.

In some embodiments, the internal threads of the proximal nut 416 and the corresponding external threads of the proximal threaded member 422 can be configured with a first thread-type (e.g., left-handed), and the internal threads of the distal nut 418 and the corresponding external threads of the distal threaded member 424 can be configured with second, opposite thread-type (e.g., right-handed) (similar to a turnbuckle). In this manner, rotating the torque shaft in a first direction (e.g., clockwise) causes the delivery cylinder 406 to move axially distally relative to the suture retention member 430 and the suture tensioning member 432 to move axially proximally relative to the suture retention member 430. Conversely, rotating the torque shaft in a second, opposite direction (e.g., counterclockwise) causes the delivery cylinder 406 to move axially proximally relative to the suture retention member 430 and the suture tensioning member 432 to move axially distally relative to the suture retention member 430.

In some embodiments, the internal threads of the proximal nut 416 and the corresponding external threads of the proximal threaded member 422 can be configured with a first thread-pitch (e.g., 0.635 mm), and the internal threads of the distal nut 418 and the corresponding external threads of the distal threaded member 424 can be configured with second, different thread-pitch (e.g., 0.45 mm). As such, when the torque shaft 420 rotates at rotational rate or speed (e.g., rpm), the proximal nut 416 and the distal nut 418 can move axially along the respective threaded members 422, 424 at different axial rates or speeds (e.g., mm/s) relative to the torque shaft 420. Thus, the delivery cylinder 406 (which can be coupled to the proximal nut 416) can move axially more quickly relative to the suture retention member 430 and the prosthetic valve 102 than the suture tensioning member 432 (which can be coupled to the distal nut 418).

Although not shown, a prosthetic valve can be releasably coupled to the delivery apparatus 400 with sutures 440 (FIG. 18), for example, in a manner similar to which the prosthetic valve 102 is releasably coupled to the delivery apparatus 300 with sutures 328 (see, e.g., FIG. 15).

As such, after the prosthetic valve has been deployed from the delivery cylinder 406 of the delivery apparatus 400, the delivery apparatus 400 can be used to simultaneously radially converge the apices of the prosthetic valve and to advance the delivery cylinder 406 over the prosthetic valve by rotating the torque shaft in a first direction. The apices of the prosthetic valve radially converge as the suture tensioning member 432 moves proximally relative to the suture retention member 430 due to the increased tension on the sutures (see, e.g., FIG. 17).

The delivery apparatus 400 also can be used to simultaneously expose the prosthetic valve from the delivery cylinder 406 and to radially expand the apices of the prosthetic valve by rotating the torque shaft in a second direction. The prosthetic valve becomes exposed from the delivery cylinder 406 as the delivery cylinder 406 moves proximally relative to the prosthetic valve, and the apices of the prosthetic valve radially expand as the suture tensioning member 432 moves distally relative to the suture retention member 430 due to the decreased tension on the sutures and the self-expanding force of the prosthetic valve (see, e.g., FIG. 15).

Figure 22:
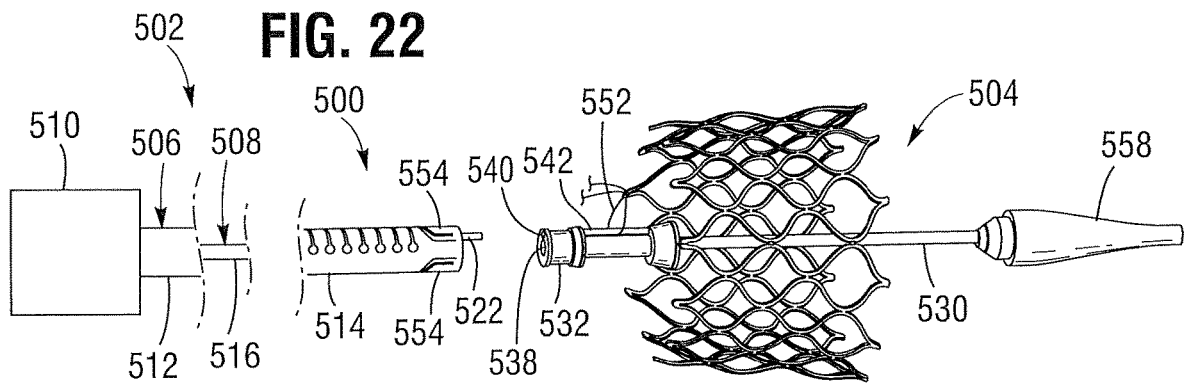
FIGS. 22-25 are various views of an example of another embodiment of a delivery apparatus.

FIGS. 22-25 show an example of a delivery apparatus 500, according to one embodiment. As shown in FIG. 22, the delivery apparatus 500 can, for example, be a component of a delivery assembly comprising a prosthetic valve (e.g., the prosthetic valve 102) and the delivery apparatus 500.

Referring still to FIG. 22, the deliver apparatus 500 can comprise a first, proximal portion 502 and a second, distal portion 504. The first and second portions 502, 504 can be separately formed, and the second portion 504 can be coupled to the distal end of the first portion 502, as further explained below.

The first portion 502 of the delivery apparatus 500 can comprise a first catheter 506 (which can be referred to as an implant delivery catheter) and a second catheter 508 (which can be referred to as a guide-wire catheter) extending coaxially through the first catheter 508. The proximal ends of the catheters 506, 508 can extend to and/or be coupled to a handle 510. The catheters 506, 508 can be independently moveable (e.g., axially and/or rotatably) relative to each other.

The first catheter 506 can comprise an elongate proximal shaft portion 512 extending distally from the handle 510, an intermediate portion (not shown) extending distally from the distal end of the proximal shaft 512, and a distal end portion 514 extending distally from the distal end of the intermediate portion. The distal end portion 514 can, for example, comprise a slotted tube to enhance the flexibility of the distal end portion 514 of the first catheter 506. A separate sheath (not shown) can extend over the shaft 512, and the distal end portion 514 for retaining a prosthetic valve 102 in a compressed state for delivery into a patient.

Figure 24A:
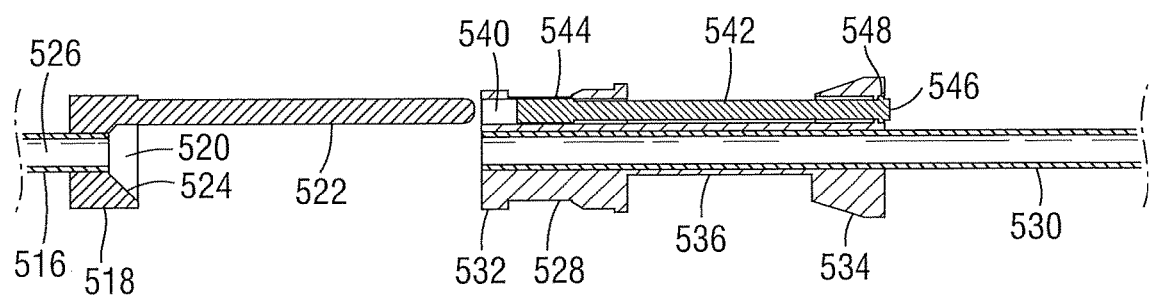

Referring to FIG. 24A, the second catheter 508 can have an elongate guide-wire shaft 516 extending distally from the handle 510 (FIG. 22) and a pusher element 518 which is connected to the distal end of the guide-wire shaft 516. The pusher element 518 can have centrally radially disposed lumen 520 and a push pin 522 disposed radially outward from the lumen 520 and extending distally from the distal surface of the pusher element 518. The lumen 520 can have a radially tapered or funnel portion 524, which can help to direct a guide-wire (not shown) into a lumen 526 of the guide-wire shaft 516 when the guide-wire is initially inserted into the delivery apparatus 500.

The second portion 504 of the delivery apparatus 500 can comprise a suture retention member 528 and a nose-cone shaft 530 connected to and extending distally from the suture retention member 528. The suture retention member 528 can have a proximal portion 532, a distal portion 534, a radially recessed intermediate portion 536 disposed between the proximal and distal portions 532, 534. The second portion 504 can also have a radially centrally disposed, first lumen 538 (FIG. 24C) extending coaxially through the suture retention member 528, the nose-cone shaft 530, and a nose cone 558 (which is connected to the distal end of the nose-cone shaft 530).

Figure 23A:
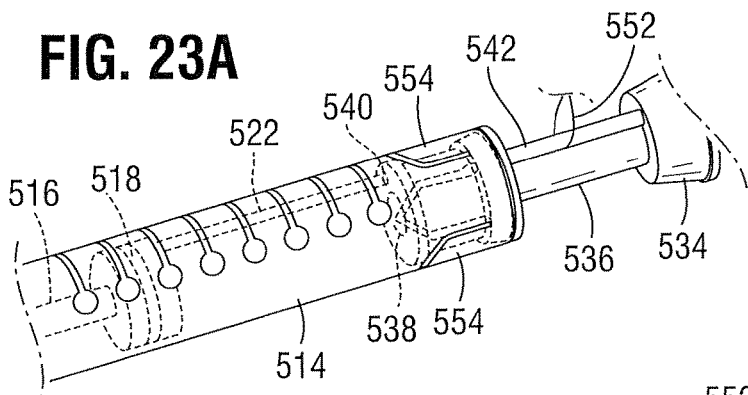
Figure 23B:
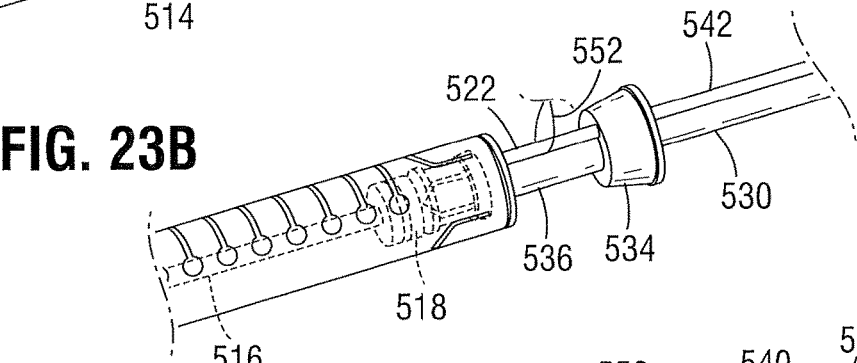
Figure 23C:
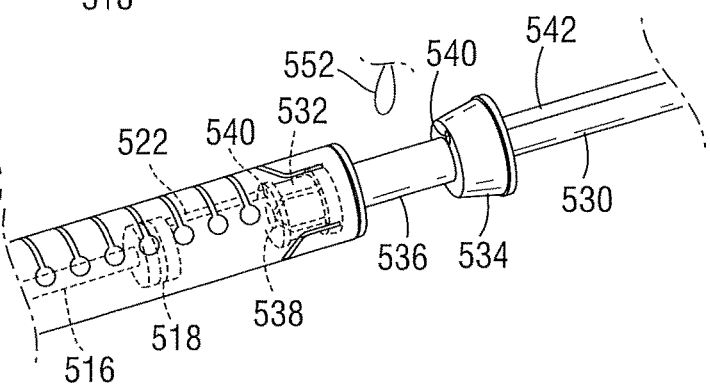

The proximal and distal portions 532, 534 of the suture retention member 528 can each have a respective second lumen 540 which extends axially through a respective proximal or distal portion 532, 534 and is disposed radially outward from the intermediate portion 536 (see also, FIG. 23C). A release pin 542 can be disposed in the second lumens 540 and can be axially moveable within the second lumens 540 between a first, proximal position (e.g., FIG. 24A) and a second, distal position (e.g., FIG. 24C). As best shown in FIG. 24A, in the first position, a proximal end portion 544 of the release pin 542 is disposed within the proximal portion 532 of the suture retention member 528 and a distal end portion 546 of the release pin 542 is disposed within the distal portion 534 of the suture retention member 528. As best shown in FIG. 24C, in the second position, the proximal end 544 of the release pin 542 is disposed within the distal portion 534 of the suture retention member 528 and the distal end 546 of the release pin 542 extends distally from the distal portion 534 of the suture retention member 528.

As best shown in FIG. 24A, the proximal end portion 544 of the release pin 542 can have a larger diameter than an adjacent portion of the release pin 542. The distal end portion 546 of the release pin 542 can have a larger diameter than an adjacent portion of the release pin 542 and/or can have an annular ridge 548 which extends radially outward from the distal end portion 546 of the release pin 542.

Figure 24B:
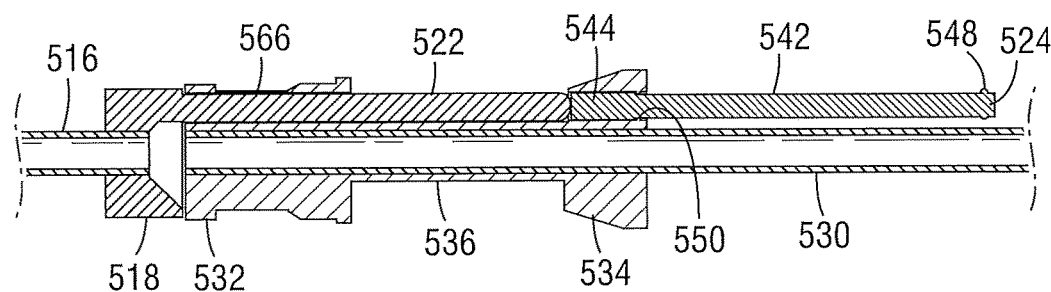
Figure 24C:
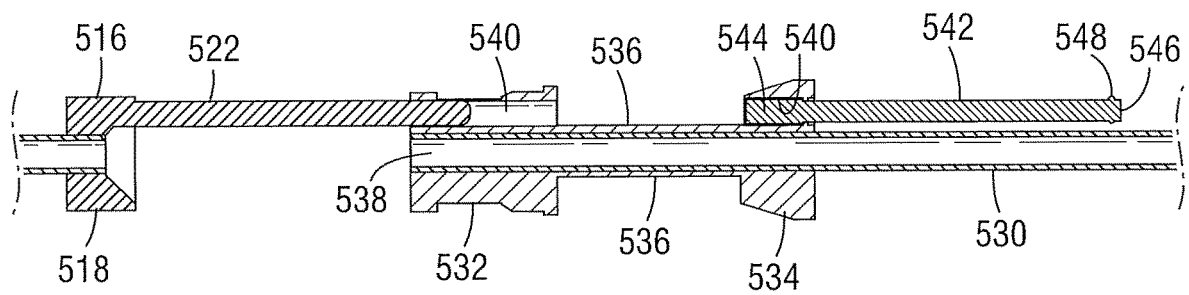

As best shown in FIG. 24B, the second lumen 540 of the distal portion 534 can have an annular lip or shoulder portion 550, which extends radially inward. The lip 550 can be configured to have a diameter that is less than the diameters of the proximal end portion 544 and the ridge 548 of the release pin 542 but approximately equal or slightly greater than the diameter of the portions of the release pin 542 that are adjacent to the distal end 548 and the ridge 548 of the release pin 542.

In this manner, the lip 550 can prevent the proximal end portion 544 of the release pin 542 from moving axially distally past the lip 550 as the release pin 542 moves from the first position (e.g., FIG. 24A) to the second position (e.g., FIG. 24C). Similarly, the lip 550 can also prevent the ridge 548 of the release pin 542 from moving axially proximally past the lip 550 as the release pin 542 moves from the second position to the first position.

Figure 25:
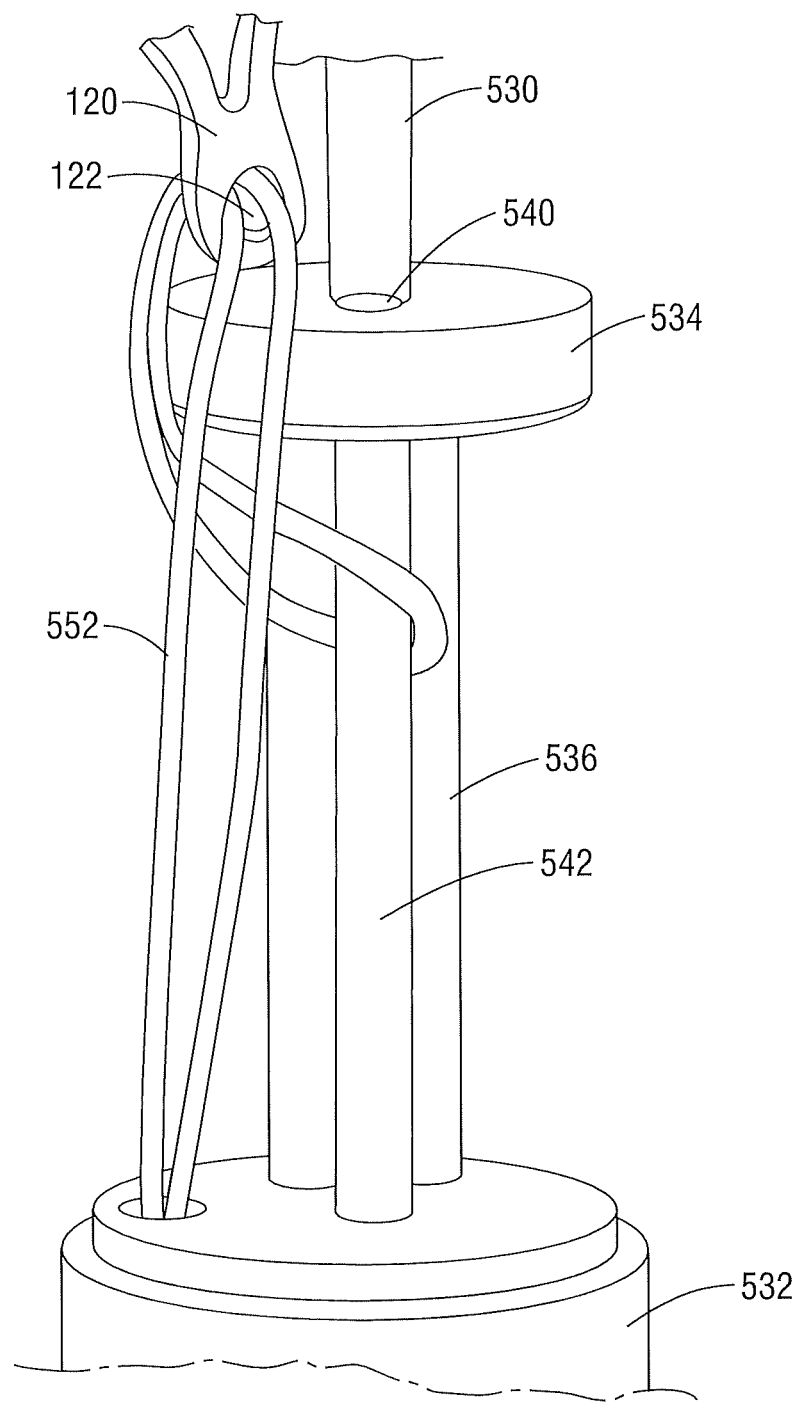

A prosthetic valve can be releasably coupled to the second portion 504 of the delivery apparatus 500 by sutures. For example, FIG. 22 shows the prosthetic valve 102 coupled to the second portion 504 of the delivery apparatus 500 by a suture loop 552. As best shown in FIG. 25, the suture loop 552 can extend radially through an aperture 122 of an apex 120 (or around the apex) of the prosthetic valve 102 and circumferentially around the release pin 522 of the suture retention member 528. The suture loop 552 can be wrapped around the release pin 542 by positioning the release pin 542 in the second position (FIG. 24C). The suture loop 552 can then be placed adjacent to the intermediate portion 536 of the suture retention member 528, and the release pin 542 can be moved axially proximally through the suture loop 552 (FIG. 25) and to the first position (FIG. 24A).

The ends (not shown) of the suture loop 552 can extend into and/or through the proximal portion 532 the suture retention member 528 and can be secured to the proximal portion 532 (e.g., by an adhesive, knots, etc.).

Although not shown, it should be noted that, the delivery apparatus 500 can comprise more than one suture loop 552 connecting the apices of the valve frame to the release pin 542. For example, the delivery apparatus 500 can have a suture loop 552 corresponding to some or all of the apices 120 of the prosthetic valve 102. In particular embodiments, the delivery apparatus 500 has 12-15 suture loops 552. In some embodiments, a single suture loop can extend through or around more than one apex of the prosthetic valve. Desirably, all of the apices at the proximal end of the frame are connected to the release pin 542 by one or more suture loops.

An assembly comprising the second portion 504 and a prosthetic valve 102 connected to the second portion 504 by sutures 552 can be assembled by the manufacturer and packaged in a sterile package for shipment to and storage by the end user. The first portion 502 of the delivery apparatus can be assembled by the manufacturer and packaged in a separate sterile package for shipment to and storage by the end user.

Referring now to FIGS. 22-23A, the delivery apparatus 500 can be assembled by the end user by coupling the second portion 504 to the distal end of the first portion 502. This can be accomplished by inserting the proximal portion 532 of the suture retention member 528 into the distal shaft 514 of the first catheter 506, as best shown in FIG. 23A. The distal shaft 514 can have one or more tabs 554 which project radially inward. The tabs 554 can engage an annular recessed portion 556 (FIG. 24B) of the proximal portion 532 of the suture retention member 528. The tabs 554 can be configured to form a snap-fit type connection with proximal member 532 sufficient to secure the suture retention member 528 to the distal shaft 514. The prosthetic valve 102 can then be compressed and loaded into a sheath (e.g., by advancing the sheath distally over the prosthetic valve), which retains the prosthetic valve in a radially compressed state around the shaft 530.

The prosthetic valve 102 can be inserted into and advanced through a patient's body as described above. At or adjacent to the implantation site, the sheath can be retracted to allow the prosthetic valve to self-expand. The prosthetic valve 102 can be released from the delivery apparatus, for example, by distally advancing the guide-wire catheter 508 relative to the implant delivery catheter 506 such that the push pin 522 advances distally into and through the lumens 540 of the proximal and the distal portions 532, 534 of the suture retention member 528. In this manner, the push pin 522 pushes the release pin 542 axially distally from the first position to the second position, as best shown in FIG. 23B. As a result, the push pin 522 now extends through the suture loop 552.

Alternatively, the push pin 522 and thus the release pin 542 can be advanced distally such that the push pin 522 extends through the suture loop 552 prior to loading the prosthetic valve 102 into the sheath. The prosthetic valve 102 can then be loaded into the sheath and inserted into a patient's body using the delivery apparatus 500.

Once inside the patient's body and the push pin 522 extending through the suture loop 552, the prosthetic valve 102 can be selectively released from the delivery apparatus 500 by proximally retracting the shaft 516 of the guide-wire catheter 508 relative to the implant delivery catheter 506 such that a distal end of the push pin 522 is proximal to the intermediate portion 536 of the suture retention member 528, as best shown in FIG. 23C. This can be accomplished, for example, by pulling on the guide-wire catheter 508 near the handle 510 while maintaining the positioning of the implant delivery catheter 506. This releases the suture loop 552 from the push pin 522 and thus the prosthetic valve 102 from the delivery apparatus 500.

Configuring the delivery apparatus 500 such that a prosthetic valve can be pre-mounted to the second portion 504, which can then be coupled to the first portion 502 in a relatively easy manner can provide several significant advantages. For example, the first portion 502 can be manufactured and/or shipped separately from the assembly comprising the second portion 504 and the prosthetic valve and later assembled (e.g., in an operating room). This can advantageously simplify and/or improve manufacturing and/or logistical efficiency. It can also advantageously enable and/or improve modularity. For example, a physician can interchange various prosthetic valves and/or delivery apparatuses relatively easily to obtain the desired configuration.

Figure 26A:
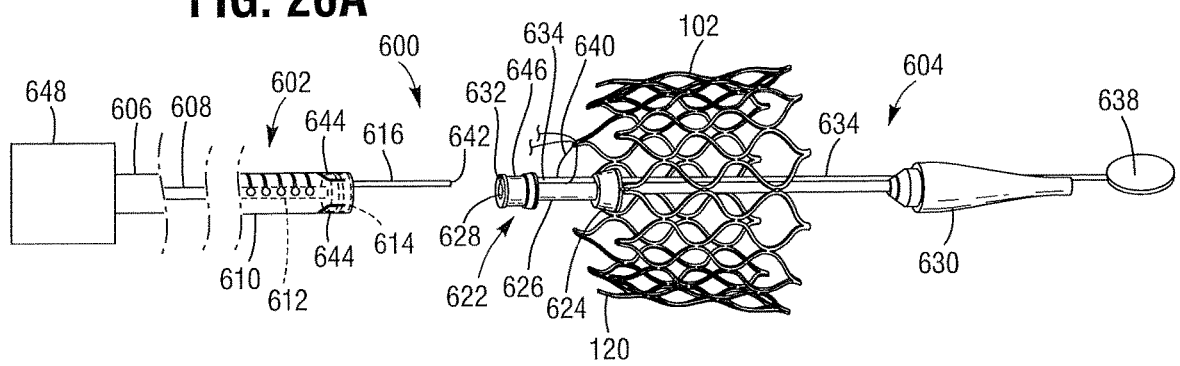
FIGS. 26A-26C are various views of an example of another embodiment of a delivery apparatus.
Figure 26B:
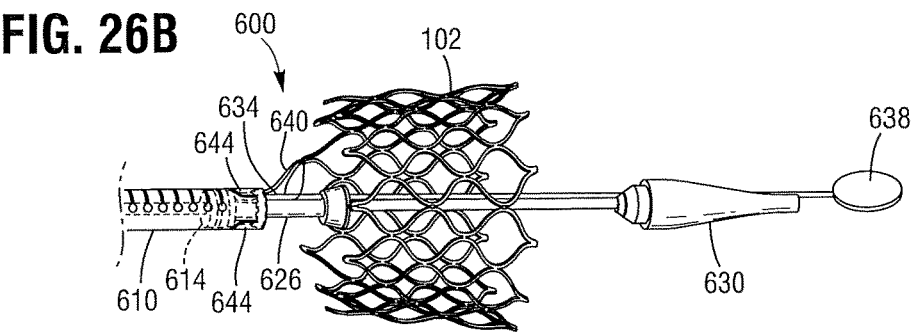
Figure 26C:
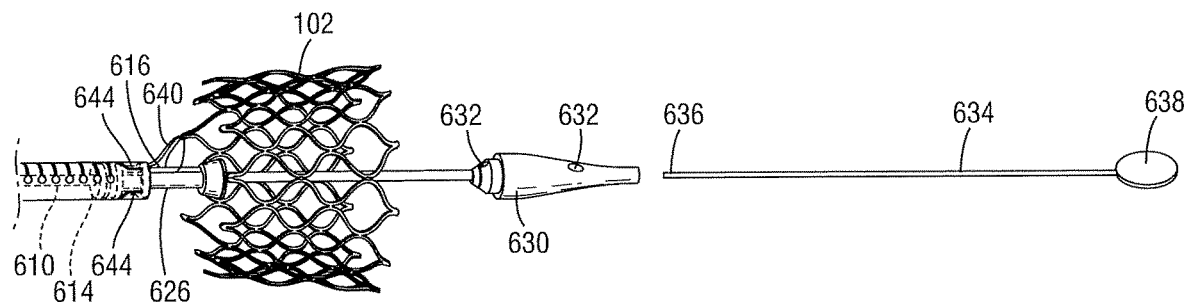

FIGS. 26A-26C show an example of one embodiment a delivery apparatus 600, which is similar to the delivery apparatus 500. As shown, the delivery apparatus 600 can, for example, be a component of a delivery assembly comprising a prosthetic valve (e.g., the prosthetic valve 102) and the delivery apparatus 600.

Referring to FIG. 26A, the deliver apparatus 600 can comprise a first, proximal portion 602 and a second, distal portion 604. The first and second portions 602, 604 can be separately formed, and the second portion 604 can be coupled to the distal end of the first portion 602, as further explained below.

The first portion 602 of the delivery apparatus 600 can be configured in a manner similar to the first portion 502 of the delivery apparatus 500. As such, the first portion 602 can comprise a first catheter 606 (which can be referred to as an implant delivery catheter) and a second catheter 608 (which can be referred to as a guide-wire catheter) extending coaxially through the first catheter 608. The proximal ends of the catheters 606, 608 can extend to and/or be coupled to a handle 648. The catheters 606, 608 can be independently moveable (e.g., axially and/or rotatably) relative to each other. A separate sheath (not shown for purposes of illustration) can extend over the first catheter 606 for retaining a prosthetic valve 102 in a compressed state for delivery.

The first catheter 606 can, for example, have a distal end portion 610 formed from a slotted tube. The second catheter 608 can have an elongate guide-wire shaft 612 extending distally from the handle 648 and a pusher element 614 which is connected to the distal end of the guide-wire shaft 612. The pusher element 614 can have centrally radially disposed lumen (not show, but see lumen 520) and a push pin 616 disposed radially outward from the lumen and extending distally from the distal surface of the pusher element 614. The lumen can have a radially tapered or funnel portion (not shown, but see funnel portion 524), which can help to direct a guide-wire (not shown) into a lumen (not shown, but see lumen 526) of the guide-wire shaft 612 when the guide-wire is initially inserted into the delivery apparatus 600.

The second portion 604 of the delivery apparatus 600 can comprise a suture retention member 618 and a nose-cone shaft 620 connected to and extending distally from the suture retention member 618. The suture retention member 618 can have a proximal portion 622, a distal portion 624, a radially recessed intermediate portion 626 disposed between the proximal and distal portions 622, 624.

The second portion 604 can have a radially centrally disposed, first lumen 628 which extends coaxially through the suture retention member 618, the nose-cone shaft 620, and a nose cone 630 (which is connected to the distal end of the nose-cone shaft 620). The second portion 604 can also have a second lumen 632 which is disposed radially outward from the first lumen 628 and extends coaxially through the proximal and distal portions 622, 624 of the suture retention member 618 and through the nose cone 630.

The second portion 604 can have a release sleeve 634 which can be removably disposed in the second lumen 632. The release sleeve 634 can be axially moveable within the second lumen 632 between a fully inserted, first position (e.g., FIG. 26A) and a fully removed, second position (e.g., FIG. 26C). As best shown in FIG. 26A, in the first position, a proximal end portion 636 of the release sleeve 634 is disposed in the second lumen 632 and axially adjacent to the proximal portion 622 of the suture retention member 618. As shown in FIG. 26C, in the second position, the release sleeve 634 has been moved axially distally such that the proximal end portion 636 is fully removed from the second lumen 632 (i.e., distal to the nose cone 630).

The release sleeve 634 can be configured to form a relatively snug tolerance fit within the second lumen 632 so that the release sleeve 634 does not inadvertently slide out of the second lumen yet a user can remove the release sleeve 634 by pulling on a pull tab 638 at the distal end of the release sleeve with one hand while holding the nose cone 630 with the other hand. The release sleeve 634 can also be configured such that the push pin 616 of the second catheter 604 can extend coaxially through the release sleeve 634, as further described below.

A prosthetic valve can be releasably coupled to the second portion 604 of the delivery apparatus 600 by sutures. For example, as shown, the prosthetic valve 102 can be releasably coupled to the second portion 604 of the delivery apparatus 600 by a suture loop 640. The suture loop 640 can extend radially through an aperture 122 of an apex 120 or around the apex 120 of the prosthetic valve 102, circumferentially around the release sleeve 634 of the suture retention member 618, and back to the apex 120 of the prosthetic valve 102. The suture loop 640 can be wrapped around the release sleeve 634 by positioning the release sleeve 634 such that the proximal end 636 of the release sleeve 634 is distal to the intermediate portion 626 of the suture retention member 618. The suture loop 640 can then be placed adjacent to the intermediate portion 626, and the release sleeve 634 can be moved axially proximally through the suture loop 640 and to the first position, as shown in FIG. 26A.

Although not shown, it should be noted that, the delivery apparatus 600 can comprise more than one suture loop 640 connecting the apices 120 of the prosthetic valve 102 to the release sleeve 634. For example, the delivery apparatus 600 can have a suture loop 640 corresponding to some or all of the apices 120 of the prosthetic valve 102. In particular embodiments, the delivery apparatus 600 has 12-15 suture loops 640.

In particular embodiments, the prosthetic valve 102 can be pre-attached to the second portion 604 and packaged together in a sterile package separate from the first portion 602, which can be shipped and stored in a respective sterile package.

Referring now to FIGS. 26A-26B, the delivery apparatus 600 can be assembled (e.g., by the end user) by coupling the second portion 604 to the distal end of the first portion 602. This can be accomplished, for example, by inserting a distal end 642 of the push pin 616 into the second lumen 632 and the release sleeve 634 and by inserting the proximal portion 622 of the suture retention member 618 into the distal shaft 610 of the first catheter 606, as shown in FIG. 26B. The distal shaft 610 can have one or more tabs 644 which project radially inward. The tabs 644 can engage an annular recessed portion 646 (FIG. 26A) of the proximal portion 622 of the suture retention member 618. The tabs 644 can be configured to form a snap-fit type connection with proximal member 622 sufficient to secure the suture retention member 618 to the distal shaft 610. The push pin 616 is advanced distally through the release sleeve 634 until a distal end 646 of the push pin 616 is axially adjacent to the distal portion 624 of the suture retention member 618.

Prior to loading the prosthetic valve 102 into a sheath, the release sleeve 634 can be removed from the second lumen 632 by distally advancing the release sleeve 634 to the second position by pulling on the pull tab 638, thus leaving the push pin 616 extending axially through the suture loops 640, as shown in FIG. 26C. The prosthetic valve 102 can then be loaded into the sheath and inserted into a patient's body using the delivery apparatus 600.

Once inside the patient's body, the prosthetic valve 102 can be selectively released from the delivery apparatus 600 by proximally retracting the guide-wire catheter 608 relative to the implant delivery catheter 606 such that the distal end 642 of the push pin 616 is proximal to the intermediate portion 626 of the suture retention member 618. This can be accomplished, for example, by pulling on the guide-wire catheter 608 near the handle 648 while maintaining the positioning of the implant delivery catheter 606. This releases the suture loops 640 from the push pin 616 and thus the prosthetic valve 102 from the delivery apparatus 600.

FIGS. 27A-29 show an example of a delivery apparatus 700, according to one embodiment. As shown, the delivery apparatus 700 can, for example, be a component of a delivery assembly comprising a prosthetic valve (e.g., the prosthetic valve 102) and the delivery apparatus 700.

Figure 27A:
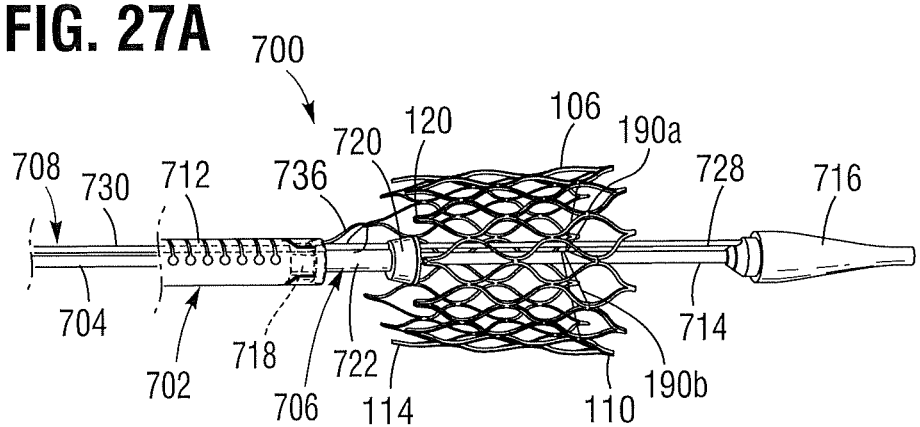
FIGS. 27A-29 are various views of an example of another embodiment of a delivery apparatus.
Figure 28A:
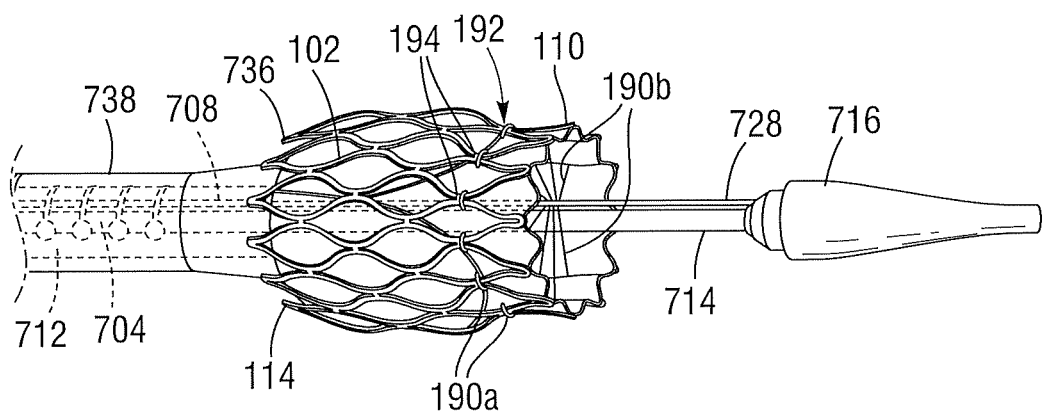
Figure 29:
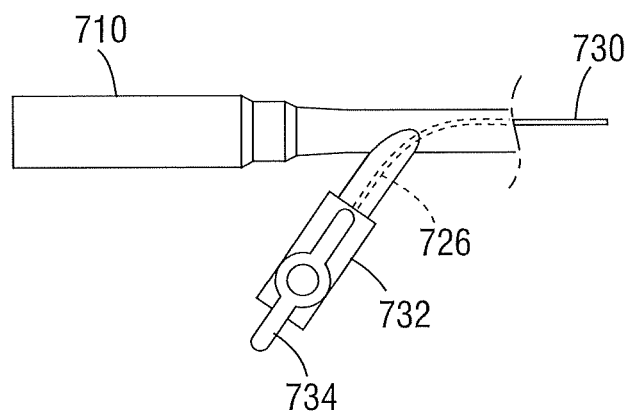

Referring to FIG. 27A, the deliver apparatus 700 can comprise a first catheter 702 (which can be called an implant delivery catheter), a second catheter 704 (which can be called a guide wire catheter), a suture retention member 706, and a release shaft 708. The delivery apparatus can also have a delivery cylinder 738 (FIG. 28A) which extends over the catheters 702, 704. The proximal ends of the catheters 702, 704 and the release shaft 708 can extend to and/or be coupled to a handle 710 (FIG. 29). The suture retention member 706 can be secured or coupled to the distal end of the first catheter 702. The second catheter 704 can extend coaxially through the first catheter 702 and the suture retention member 706. The release shaft 708 can extend axially through the first catheter 702 and the suture retention member 706 and can be disposed radially outward (i.e., eccentric) from the second catheter 704. The catheters 702, 704 and the release shaft 708 can be independently moveable (e.g., axially and/or rotatably) relative to each other.

The first catheter 702 can comprise an elongate distal end portion 712 formed, for example, from a slotted tube to enhance the flexibility of the distal end portion 712 of the first catheter 702 in a manner similar to the first catheter 506.

Referring to FIG. 27A, the second catheter 702 can have an elongate nose cone shaft 714 at a distal end portion of the second catheter. A nose cone 716 can be connected to the distal end of the nose cone shaft 714. The second catheter 702 can have a guide wire lumen (not shown) extending coaxially through the nose cone shaft 714 and the nose cone 716.

Figure 27B:
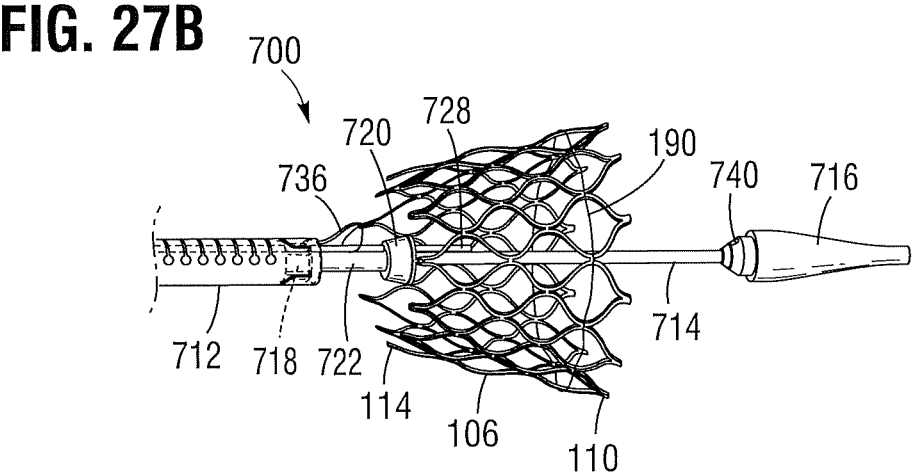
Figure 27C:
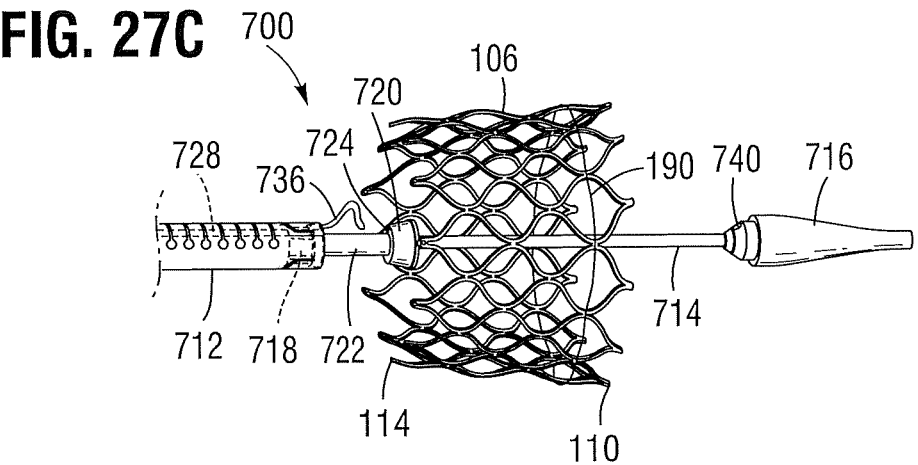

The suture retention member 706 can have a proximal portion 718, a distal portion 720, and a radially recessed intermediate portion 722 disposed between the proximal and distal portions 718, 720. The suture retention member 706 can have a radially centrally disposed, first lumen (not shown) through which the nose cone shaft 714 can extend. The first lumen can extend coaxially through the proximal, intermediate, and distal portions 718, 722, 720 of the suture retention member 706. As best shown in FIG. 27C, the suture retention member 706 can also have a second lumen 724 which can be disposed radially outward from the first lumen and the intermediate portion 722 and extend axially through the proximal and distal portions 718, 720.

As noted above, the suture retention member 706 can be secured or mounted to the distal end portion 714 of the first catheter 702 (e.g., via a snap-fit connection). Additionally and/or alternatively, the suture retention member 706 can be secured or coupled to the nose cone shaft 714. As such, the delivery apparatus 700 can be assembled as a single unit and/or in a first, proximal portion and a second, distal portion which can be separately manufactured and later assembled (e.g., in a manner similar to delivery apparatuses 500, 600).

The release shaft 708 can have a proximal end portion 726 extending distally from and/or disposed adjacent to the handle 710 (as shown in FIG. 29), a distal end portion 728 that is opposite from the proximal end portion 726, and an intermediate portion disposed between the end portions 726, 728. As noted above and best shown in FIGS. 27A-27C, the release shaft 708 can be axially movable (i.e., proximally and distally) relative to the catheters 702, 704. For example, the release shaft 708 can be positioned in a first, distal position in which the distal end portion 728 of the release shaft 708 extends into an opening 740 of the nose cone 716 (or extends adjacent to the nose cone 716), as best shown in FIG. 27A. From the first position, the release shaft 708 can be retracted proximally to a second, intermediate position in which the distal end portion 728 of the release shaft 708 is disposed distal but relatively close to the distal portion 720 of the suture retention member 706, as best shown in FIG. 27B. From the second position, the release shaft 708 can be further retracted proximally to a third, proximal position in which the distal end portion 728 of the release shaft 708 is disposed proximal to the proximal portion 718 of the suture retention member 706, as best shown in FIG. 27C. From the second position (FIG. 27B) and/or the third position (FIG. 27C), the release shaft 708 can be advanced distally to the first position (FIG. 27A). The release shaft 708 can also be axially movable to various other positions.

The distal end 728 of the release shaft 708 can be moved distally and/or proximally by moving the proximal end 726 of the release shaft 708 distally and/or proximally relative to the catheters 702, 702 at or adjacent to the handle 710, which in turn causes the distal end 728 to accordingly. In some embodiments, a release shaft positioning member 732 can be adjustably coupled to the proximal end 726 of the release shaft 706, as shown in FIG. 29. The release shaft positioning member 732 can be configured to engage the release shaft 708 so as to facilitate distal and/or proximal movement of the release shaft 708. For example, in one particular embodiment, the release shaft positioning member 732 can comprise a rotatable knob 734 which cooperates with the release shaft positioning member 732 to adjustably move the release shaft 708 distally when the knob 734 is rotated in a first direction (e.g., counterclockwise) and to adjustably move the release shaft 708 proximally when the knob 734 is rotated in a second, opposite direction (e.g., clockwise).

The release shaft 708 can be formed from various relatively flexible, yet resilient materials. For example, the release shaft 708 can be formed from nitinol, stainless steel, etc.

A prosthetic valve can be releasably coupled to the delivery apparatus 700 by sutures. For example, as best shown in FIG. 27A, the outflow end 114 of the prosthetic valve 102 (the proximal end of the prosthetic valve 102 in the illustrated embodiment) can be releasably coupled to suture retention member 706 by one or more first suture loops 736 (e.g., one shown in the illustrated embodiment). For purposes of illustration, FIGS. 27A-27C show only the frame 106 of the prosthetic valve 102. The frame 106 is shown in FIGS. 27A-28B as being substantially cylindrical, however, it should be noted that the frame 106 can have a curved profile as shown in FIG. 3.

Each of the first suture loop 736 can extend distally from the proximal portion 718 of the suture retention member 706, radially through and/or around an apex 120 of the prosthetic valve 102, circumferentially around the release shaft 708, and back to the apex 120 of the prosthetic valve 102. Each of the first suture loop 736 can be wrapped around the release shaft 708 by positioning the distal end portion 728 of the release shaft 708 proximal to the intermediate portion 722 of the suture retention member 706. The first suture loops 736 can each then be placed adjacent to the intermediate portion 722, and the distal end portion 728 of the release shaft 708 can be advanced distally through the suture loop 736 such that the distal end 728 portion of the release shaft 708 is dispose adjacent or distal to the distal portion 720 of the suture retention member 706. In this position, the outflow end 114 of the prosthetic valve 102 is releasably coupled to the delivery apparatus 700 via the first suture loops 736 (see, e.g., in the manner shown in FIG. 25). A suture loop 736 can be used for each apex of the prosthetic valve, or alternatively, one suture loop 736 can be used for connecting multiple apices to the suture retention member 706.

The outflow end 114 of the prosthetic valve 102 can be released from the delivery apparatus 700 by proximally retracting the distal end portion 728 of the release shaft 708 relative to the catheters 702, 704 such that the distal end portion 728 is proximal to the intermediate portion 722 of the suture retention member 706, as shown in FIG. 27C. This releases the suture loop 736 from the release shaft 708 and thus the apex 120 of the prosthetic valve 102 from delivery apparatus 700.

The inflow end 110 of the prosthetic valve 102 (the distal end of the prosthetic valve 102 in the illustrated embodiment) can also be releasably coupled to the delivery apparatus via one or more sutures. For example, in the illustrated embodiment, the prosthetic valve 102 comprises a suture 190 (best shown in FIG. 27B) which extends circumferentially around a waist portion 192 of the prosthetic valve 102 to form a loop. The suture 190 can be secured or coupled to junctions or intersections 194 of the frame 106 of the prosthetic valve 102. In alternative embodiments, the suture 190 can extend circumferentially around and can be secured or coupled to the apices 118 of the prosthetic valve.

Figure 28B:
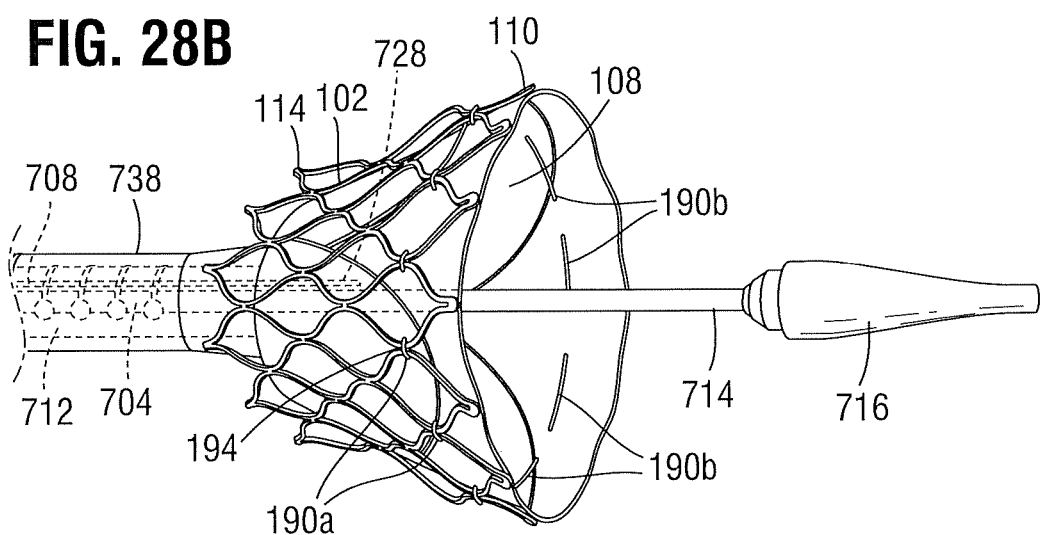

As best shown in FIG. 28B, the suture 190 can, for example, extend radially in and out of the frame 106 at the junctions 194 such that first portions 190a of the suture 190 are disposed radially outward and extend circumferentially over the junctions 194 of the frame 106 and second portions 190b of the suture 190 are disposed radially inward and extend circumferentially between the junctions 194 of the frame 106. As best shown in FIG. 28A, one or more of the second portions 190b of the suture 190 can be pulled radially inward and wrapped around the release shaft 708, thus coupling inflow end 110 of the prosthetic valve 102 to the delivery apparatus 700. This can be accomplished by positioning the distal end 728 of the release shaft 708 proximal to the second portions 190b that are pulled radially inward and then distally advancing the distal end portion 728 of the release shaft 708 through each of the second portions 190b.

Although the illustrated embodiment shows four second portions 190b wrapped around the release shaft 708, fewer or more second portions 190b can be wrapped around the release shaft 708. For example, there can be 1-15 second portions 190b that are wrapped around the release shaft 708. Also, although the illustrated embodiment shows the second portions 190b pulled radially inwardly (e.g., forming internal loops which can be wrapped around the release shaft 708), the second portions 190b can be pulled radially outwardly (e.g., forming external loops which can be wrapped around the release shaft 708).

The inflow end 110 of the prosthetic valve 102 can be released from the delivery apparatus 700 by proximally retracting the distal end portion 728 of the release shaft 708 relative to the catheters 702, 704 such that the distal end portion 728 is proximal to the second portions 190b of the suture 190, as shown in FIG. 27B. This releases the second portions 190b from the release shaft 708 and thus the inflow end 110 of the prosthetic valve 102 from delivery apparatus 700.

The suture 190 can be configured such that the length of the suture 190 is approximately the same as the circumference of the portion of the prosthetic valve to which the suture is coupled (e.g., the waist portion 192 or the apices 118) when that portion of the prosthetic valve 102 is fully radially expanded. As such, in the fully radially expanded state (FIG. 28B), the suture 190 can be relatively taut yet allow the prosthetic valve to fully radially expand.

In this manner, the suture 190 and the delivery apparatus 700 can be used to control the radially expansion of inflow end 110 of the prosthetic valve 102. For example, the inflow end 110 can be at least partially radially compressed by pulling one or more of the second portions 190b of the suture 190 radially inwardly. This effectively foreshortens the circumferential length of the suture 190 and thus reduces the diameter of the loop formed by the suture 190. As a result, the first portions 190a of the suture 190 can exert a radially compressive force on the waist portion 192 of the prosthetic valve 102 which can cause the waist portion 192 to at least partially radially compress. Pulling the second portions 190b farther radially inward and/or pulling additional second portions 190b of the suture 190 radially inward can cause the waist portion 192 of the prosthetic valve 102 to further radially compress; whereas releasing the second portions 190b can allow the prosthetic valve 102 to radially expand (due to the self-expanding nature of the prosthetic valve 102).

As best shown in FIG. 28A, the inflow end 110 of the prosthetic valve 102 can be releasably secured in a radially compressed state by wrapping the second portions 190b of the suture 190 that are pulled radially inwardly around the distal end portion 728 of the release shaft 708. FIG. 28A, for example, shows four second portions 190b that are releasably secured radially inward by the distal end portion 728 of the release shaft 708. As such, when the prosthetic valve 102 is deployed from a delivery cylinder 738, the inflow end 110 of the prosthetic 102 can partially radially expand until the second portions 190b of the suture become taut against the distal end portion 728 of the release shaft 708. Thus, the release shaft 708 prevents the second portions 190b and thus the inflow end 110 of the prosthetic valve 102 from fully expanding radially outwardly.

In the partially radially expanded state, the inflow end 110 of the prosthetic valve 102 can expand far enough that the valve structure 108 can begin functioning (e.g., the leaflets can open and close) and allowing at least some blood to flow through the valve structure 108 yet not so far that it completely blocks blood flow around the prosthetic valve 102. Allowing blood to flow through and/or around the prosthetic valve 102 can advantageously allow a physician to assess the valve positioning and/or make any desired adjustments without pressure against the prosthetic valve from the blocked blood flow causing the prosthetic valve to migrate to an undesired location. As a result, this can also advantageously reduce and/or eliminate the need for rapid pacing of the heart to stop or slow blood flow, which is typically used to stop or slow blood flow to minimize undesired migration of a prosthetic valve during an implantation procedure.

When the prosthetic valve 102 is desirably positioned, the inflow end 110 of the prosthetic valve 102 can be fully radially expanded by proximally retracting the distal end portion 728 of the release shaft 708 relative to the catheters 702, 704 such that the distal end portion 728 is proximal to the second portions 190b of the suture 190, as shown in FIG. 27B. This releases the second portions 190b from the release shaft 708 and thus allows the inflow end 110 of the prosthetic valve 102 to fully radially expand, as shown in FIG. 27B.

It should be noted that in this configuration (FIG. 27B), the prosthetic valve 102 can be retrieved and radially compressed into the delivery cylinder 738 because the sutures 736 remain coupled to the outflow end 114 of the prosthetic valve 102. This can be accomplished by proximally retracting the prosthetic valve into the delivery cylinder 738 and/or distally advancing the delivery cylinder 738 over the prosthetic valve 102. Once the desired positioning is achieved, the outflow end 114 of the prosthetic valve 102 can be released from the delivery apparatus 700 by proximally retracting the release shaft 708 (FIG. 27C), as described above.

Figure 30A:
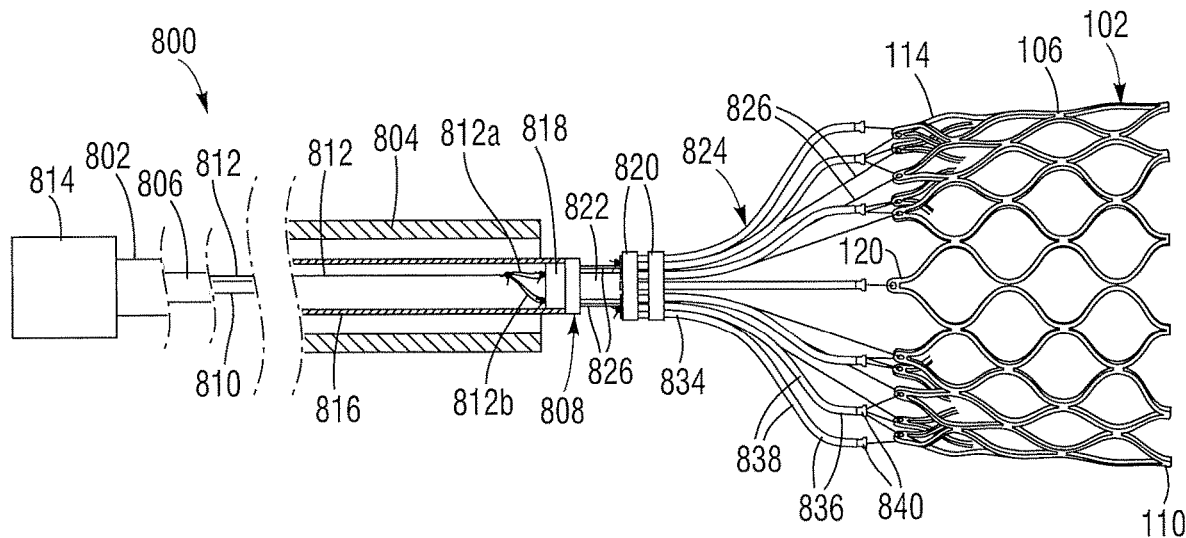
FIGS. 30A-34 are various views of an example of another embodiment of a delivery apparatus.

FIGS. 30A-34 show an example of a delivery apparatus 800, according to one embodiment. As best shown in FIG. 30A, the delivery apparatus 800 can, for example, be a component of a delivery assembly comprising a prosthetic valve (e.g., the prosthetic valve 102) and the delivery apparatus 800.

For purposes of illustration only the frame 106 of the prosthetic valve 102 is shown. Although the frame 106 is shown as being substantially cylindrical, it should be noted that the frame 106 can be curved in the manner shown in FIG. 3.

Referring still to FIG. 30A, the deliver apparatus 800 can comprise a first catheter 802 (which can be referred to as an implant delivery catheter) extending coaxially through a delivery cylinder 804, a second catheter 806 extending coaxially through the first catheter 802, a suture retention member 808 secured or coupled to a distal end of the first catheter 802, a guide-wire catheter 810 extending coaxially through the catheters 802, 806 and the suture retention member 808, and a release suture or wire 812 extending coaxially through the catheters 802, 806 and the delivery cylinder 804 and axially adjacent to the guide-wire catheter 810. The proximal ends of the catheters 802, 806, 810 and the release wire 812 can extend to and/or be coupled to a handle 814. The catheters 802, 806, 810, the delivery cylinder 804, and the release wire 812 can be independently moveable (e.g., axially and/or rotatably) relative to each other.

The first catheter 802 can comprise an elongate distal end portion 816. Although not shown, the distal end portion 816 can be formed, for example, from a slotted tube to enhance the flexibility of the distal end portion 816 of the first catheter 802 in a manner similar to the first catheter 506.

The delivery cylinder 804 can be configured to cooperate with the catheters 802, 806 similar to the manner in which the delivery cylinder 128 cooperates with the catheters 124, 126. Although not shown, the second catheter 806 can comprise a threaded member or screw which is coupled to a distal end of a rotatable torque shaft and is connected to the delivery cylinder 804 via a nut (e.g., in the manner shown in FIGS. 6A-6C).

The suture retention member 808 can comprise a proximal portion 818, a distal portion 820, a radially recessed intermediate portion 822 disposed between the proximal and distal portions 818, 820, a plurality of elongate tubes or sleeves 824 coupled or secured to and extending distally from the distal portion 820, and a plurality of sutures 826. As noted above, the proximal portion 818 of the suture retention member 808 can be coupled or secured the distal end portion 816 of the first catheter 802 (e.g., via a snap-fit connection).

Figure 31A:
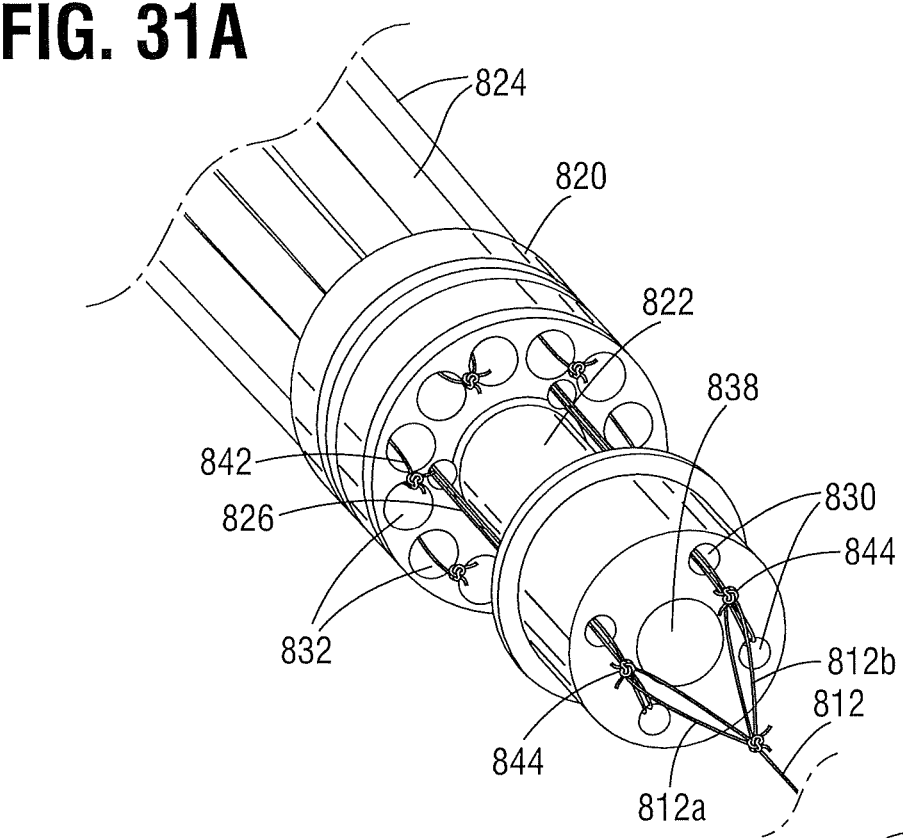
Figure 31B:
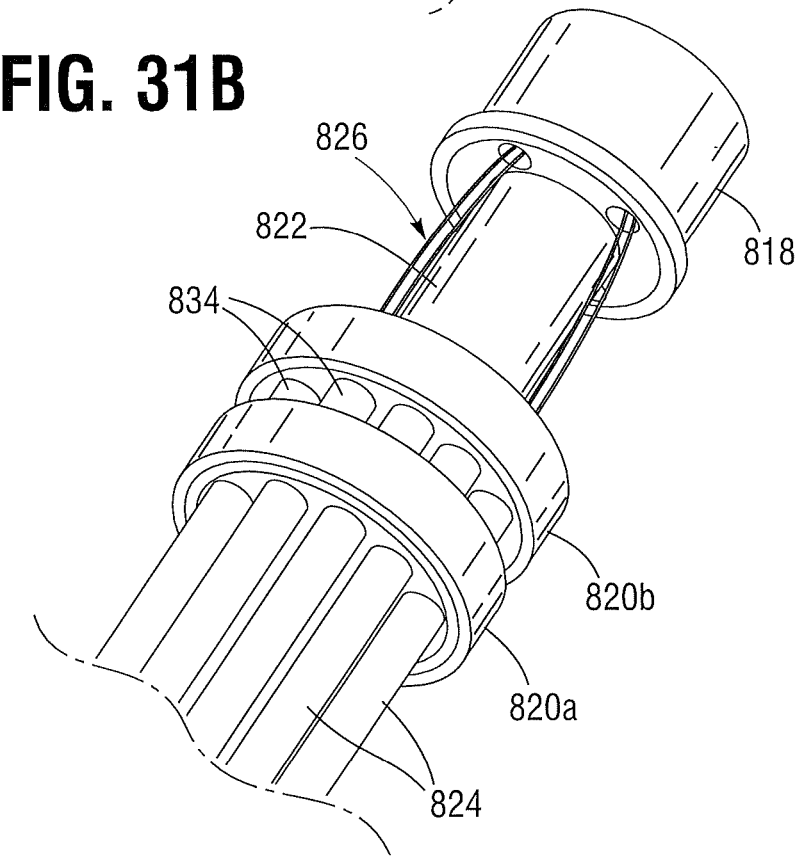
Figure 32:
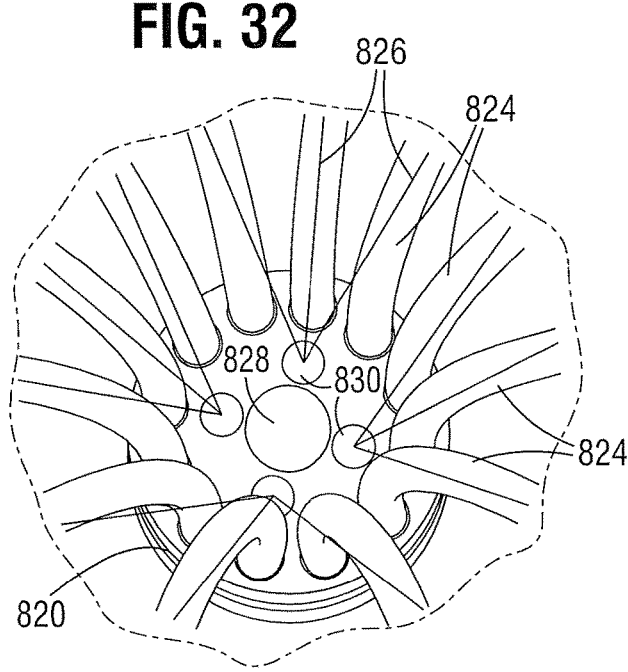

Referring now to FIGS. 31A-32, the suture retention member 808 can have a radially centrally disposed, first lumen 828. The first lumen 828 can extend coaxially through the proximal, intermediate, and distal portions 818, 822, 820 of the suture retention member 808. Although not shown, the first lumen 828 can allow the guide-wire catheter 810 to extend coaxially through the suture retention member 808. The suture retention member 808 can also have a plurality of circumferentially spaced, second lumens 830 (e.g., four in the illustrated embodiment) which can be disposed radially outward from the first lumen 828 and extend axially through the proximal and distal portions 818, 820 of the suture retention member 808. The sutures 826 can extend through respective second lumens 830, as further described below.

The distal portion 820 of the suture retention member can comprise one or more annular portions or disks. In the illustrated embodiment, the distal portion 820 has two annular portions 820a, 820b (collectively referred to herein as the "distal portion 820") which are axially spaced apart from each other, as best shown in FIG. 31B. In some embodiments, the distal portion 820 can have one annular portion. The distal portion 820 can have a plurality of circumferentially spaced, openings 832 (e.g., 12 in the illustrated embodiment) which can be disposed radially outward from the lumens 828, 830 and extend axially through the distal portion 820 of the suture retention member 808, as best shown in FIG. 31A. The openings 832 of the distal portion 820 can each be configured to receive a proximal end portion 834 of a respective sleeve 824, as best shown in FIG. 31B. The proximal end portions 834 of the sleeves 824 can be secured within the respective openings 832 of the distal portion 820, for example, by an adhesive and/or welding.

Referring again to FIG. 30A, each of the sleeves 824 can extend distally from the proximal end portion 834 to a distal end portion 836. Each of the sleeves 824 can comprise an intermediate portion 838 which curves or flares radially outwardly such that the distal end portion 836 of the sleeve 824 is disposed radially outward from the proximal end portion 834 of the sleeve 824. The intermediate portions 838 can be configured to curve or flare radially outwardly such that the distal end portions 836 are substantially radially aligned with the apices 120 of the prosthetic valve 102 when the prosthetic valve is fully radially expanded. This can advantageously allow the prosthetic valve to fully radially expand when the prosthetic valve 102 is deployed from the delivery cylinder 804 and also allow the prosthetic valve to be retrieved into the delivery cylinder 804, as further described below.

The sleeves 824 can be formed from various suitable flexible, elastic materials. In some embodiments, for example, the sleeves can be formed from a super elastic and/or shape memory material or materials such as Poly ether ketone ("PEEK") and/or nitinol. In one particular embodiment, the sleeves 824 are formed from nitinol tubes having an outer covering formed from PEEK. In some embodiments, the sleeves 824 can have a friction-reducing coating and/or surface treatment applied to them.

Figure 30B:
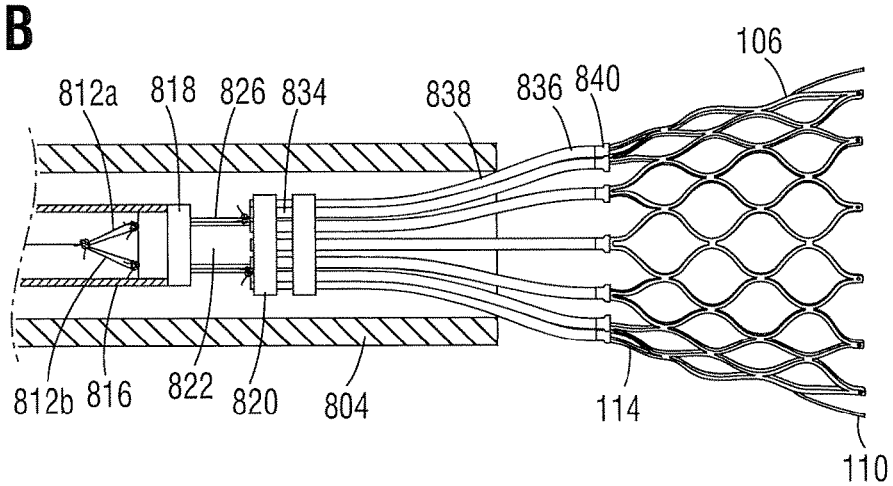
Figure 30C:
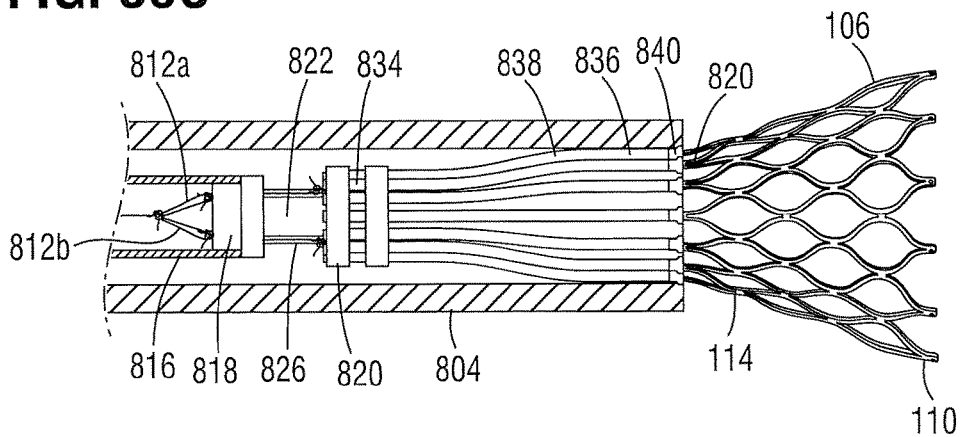

As such, the sleeves 824 can be configured to be radially compressible from a radially expanded configuration or state (e.g., FIG. 30A) to a radially compressed configuration or state (e.g., FIG. 30C). The sleeves 824 can be radially compressed from the radially expanded state, for example, by proximally retracting the first catheter 802 relative to the delivery cylinder 804 and/or by distally advancing the delivery cylinder 804 relative to the first catheter 802 such that the sleeves are disposed within and retained in the radially compressed state by the delivery cylinder 804, as best shown in FIG. 30C. The sleeves 824 can be radially expanded from the radially compressed state to the radially expanded state, for example, by distally advancing the first catheter 802 relative to the delivery cylinder 804 and/or by proximally retracting the delivery cylinder 804 relative to the first catheter 802 such that the sleeves are deployed from within the delivery cylinder 804. As the sleeves 824 are deployed from the delivery cylinder 804, the sleeves 824 can expand radially outwardly as best shown in FIGS. 30B and 30A.

Figure 33:
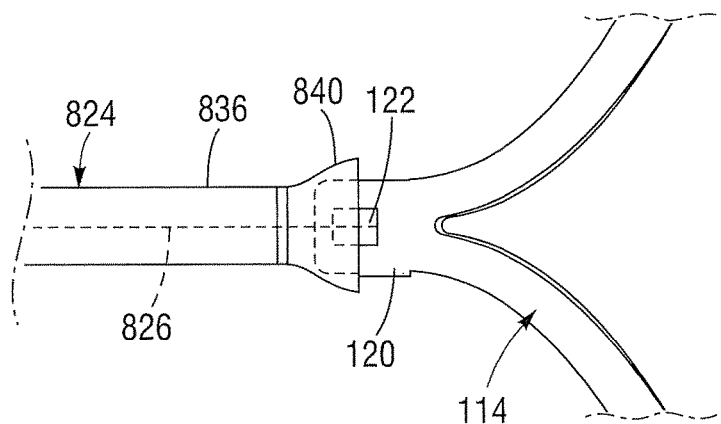

As best shown in FIG. 33, the distal end portion 836 of each sleeve 824 can have a receiving element or cup 840 coupled and/or secured to the distal tip of the sleeve 824. In some embodiments, a sleeve 824 and a respective cup 840 can be integrally formed from a single, unitary piece of material. In other embodiments, a sleeve and a respective cup 840 can be formed from separate pieces of material that are coupled to each other (e.g., by an adhesive and/or welding). As also best shown in FIG. 33, the cups 840 can be configured to receive a respective apex 120 of the prosthetic valve 102.

The prosthetic valve 102 can be releasably coupled to the delivery apparatus 800 via releasable suture loops formed by the sutures 826. The suture loops can be formed, for example, by securing first ends 842 of the sutures 826 to a proximal end of the distal portion 820 of the suture retention member 808 at or adjacent to the openings 832. This can be accomplished, for example, by tying the first end 842 of one suture 826 to the first end 842 of one or more other sutures 826. For example, FIG. 31A shows each of the first ends 842 of the sutures tied to the first end 842 of one other suture 826 (i.e., forming six pairs). The first ends 842 can be secured to the suture retention member and/or to each other in various other ways such as by an adhesive.

From the proximal end of the distal portion 820, each suture 826 can extend distally into and through a respective opening 832 and/or into and through a respective sleeve 824, as best shown in FIGS. 31A and 33. The sutures 826 can extend out of a respective sleeve 824 and extend through (e.g., via an opening 122) and/or around a respective apex 120 at the outflow end 114 of the prosthetic valve 102, as best shown in FIGS. 30A and 33.

The sutures 826 can then extend proximally (and slightly radially inward) back to the distal portion 820 of the suture retention member 808, as best shown in FIGS. 30A and 32. The sutures 826 can extend distally into and through a respective second lumen 830 of the suture retention member 808 (e.g., three sutures 826 in each second lumen 830) and second ends 844 of the sutures 826 can exit the respective second lumens 830 at the proximal end of the proximal portion 818, as best shown in FIGS. 31A-31B.

Figure 34:
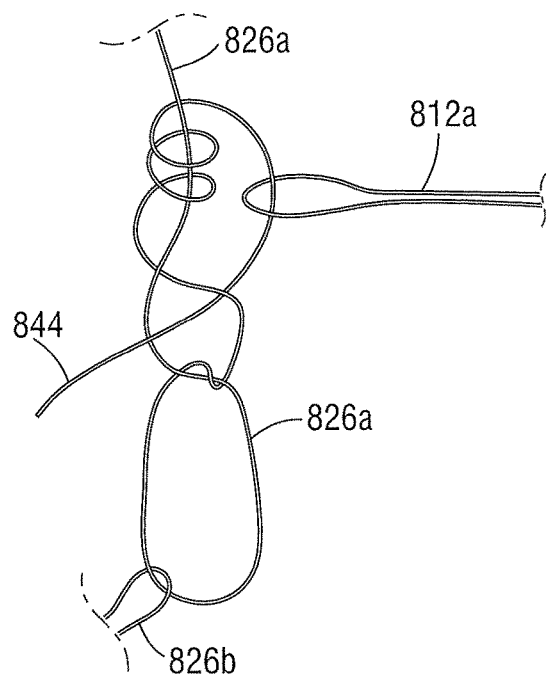

The apices 120 of the prosthetic valve 102 can then be positioned in the cups 840 of the sleeves 824 by tensioning the second ends 844 the sutures 826, which causes the apices 120 to move proximally toward and into the cups 840, as best shown in FIG. 33. The second ends 844 of the sutures 826 can then be releasably secured to each other and/or to the release wire 812. For example, FIG. 34 shows a first suture 826a tied to a second suture 826b and to a first loop 812a of the release wire 812 by a releasable knot. The knot can be unraveled by tensioning the release wire 812 which causes the first loop 812a to pull the second end 844 of the first suture 826a out of the knot, which allows the knot to unravel. Although not shown, the second suture 826b can also be releasably secured to the release wire 812 (e.g., by a second loop 812b (FIG. 31B).

In this manner, the delivery apparatus 800 can be used to deploy and/or retrieve the prosthetic valve 102 in an implantation site in a patient's body. For example, with the prosthetic valve 102 radially compressed and retained within the delivery cylinder 804, the prosthetic valve 102 can be advanced to or adjacent to an implantation site. The prosthetic valve 102 can then be deployed by distally advancing the first catheter 802 relative to the delivery cylinder 804 and/or by proximally retracting the delivery cylinder 804 relative to the first catheter 802, which can allow the prosthetic valve to radially expand. In the radially expanded state, the prosthetic valve 102 can be positioned, retrieved, and/or released from the delivery apparatus 800.

The prosthetic valve 102 can be positioned by moving the first catheter 802 axially, rotationally, etc. which in turn causes corresponding movement of the prosthetic valve 102.

The prosthetic valve 102 can be retrieved by proximally retracting the first catheter 802 relative to the delivery cylinder 804 and/or by distally advancing the delivery cylinder 804 relative to the first catheter 802. This causes the sleeves 824 of the suture retention member 808 to radially compress as the sleeves 824 retract proximally into the delivery cylinder 804, which in turn causes the apices 120 of the prosthetic valve 102 to radially compress retract proximally into the delivery cylinder 804 together with the sleeves 824. As such, the sleeves 824 can guide the apices 120 of the prosthetic valve 102 into the delivery cylinder 804. This can advantageously prevent the apices from snagging on the end of the delivery cylinder and/or significantly reduce the amount of force that is needed to retrieve the prosthetic valve 102 into the delivery cylinder 804. For example, in some embodiments, the delivery apparatus 800 requires about forty percent less force to retrieve a prosthetic valve into a delivery cylinder than a delivery apparatus without sleeves (e.g., the sleeves 824) and/or tension-able sutures.

The prosthetic valve 102 can be released from the delivery apparatus 800 by unraveling the knots in the second ends 844 of the sutures 826 by pulling the release wire 812 proximally relative to the suture retention member 808, as described above. With the second ends 844 free, the first catheter 802 and thus the suture retention member 808 can be proximally retracted relative to the prosthetic valve 102. This allows the cups 840 of the sleeves 824 to move proximally and separate from the apices 120 of the prosthetic valve 102, as shown in FIG. 30A. As the first catheter 802 is farther proximally retracted, the second ends 844 of the sutures retract from the second lumens 830 of the sutures retention member 808 and from the apices 120 of the prosthetic valve 102, thus releasing the prosthetic valve 102 from the delivery apparatus 800.

Figure 35:
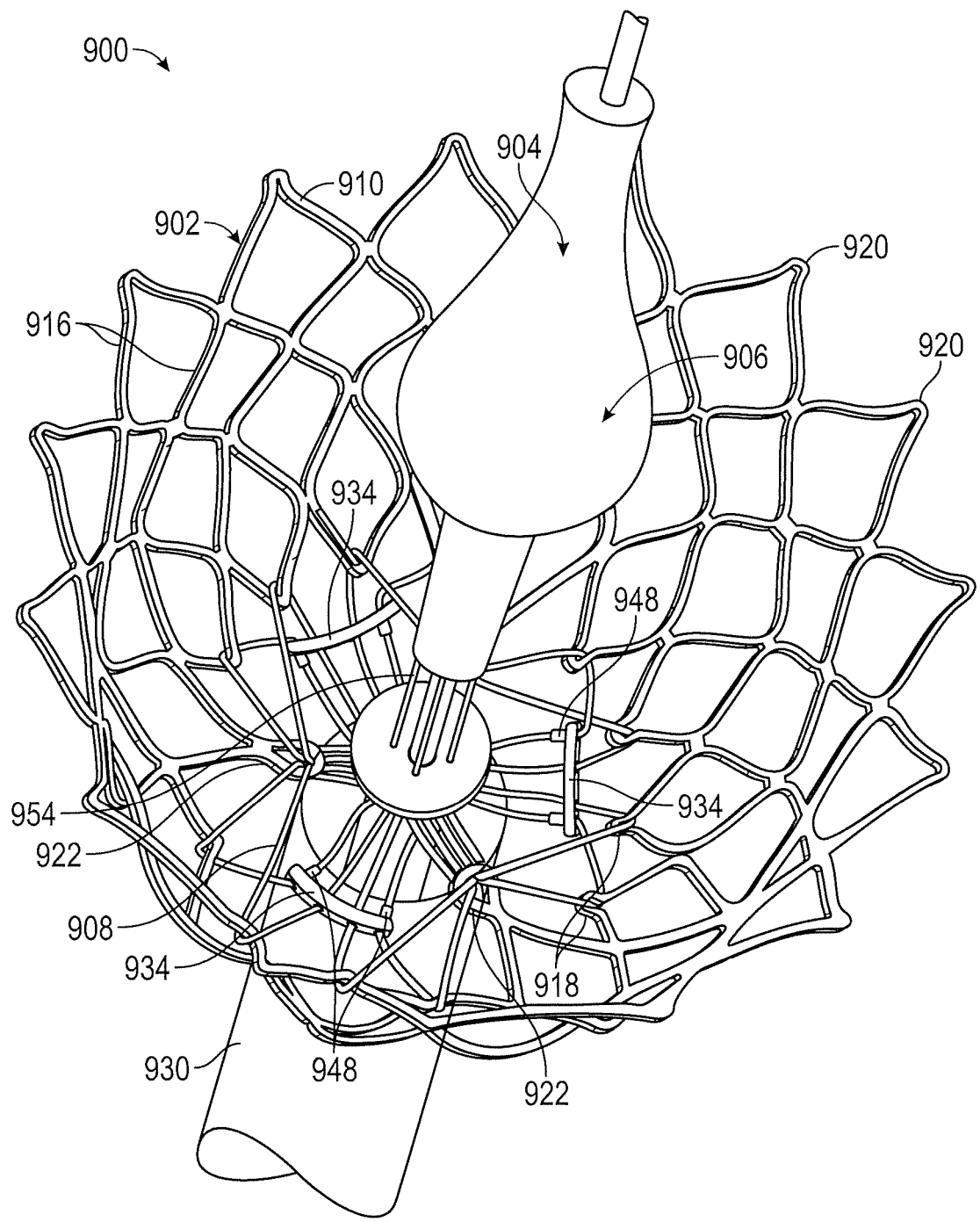
FIG. 35 is a perspective view of another exemplary embodiment of a delivery assembly.

FIGS. 35-43 show an exemplary embodiment of a delivery assembly 900 and its components. Referring to FIG. 35, the delivery assembly 900 can comprise two main components: a prosthetic heart valve 902 and a delivery apparatus 904. To better illustrate a releasable coupling between the prosthetic heart valve 902 and the delivery apparatus 904, only an annular frame 910 of the prosthetic heart valve 902 is shown. The prosthetic heart valve 902 can, however, comprise various other components (e.g., a valve structure) and can be configured similar to the prosthetic heart valve 102. The prosthetic heart valve 902 can be releasably coupled to a distal end portion 906 of the delivery apparatus 904 with a plurality of suture loops 908, as further explained below.

Figure 36:
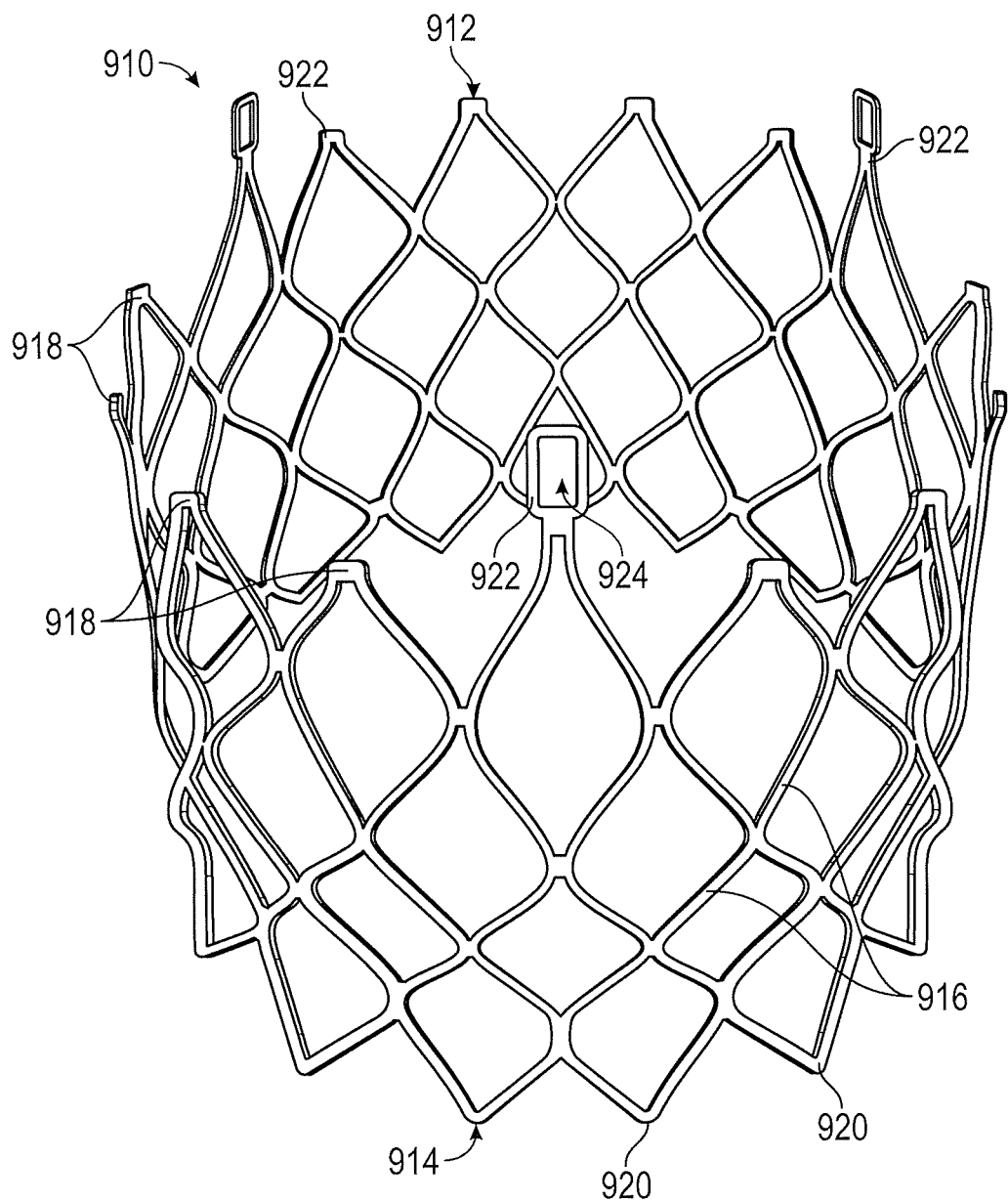
FIG. 36 is a perspective view of a prosthetic heart valve frame of the delivery assembly of FIG. 35.

Referring to FIG. 36, the frame 910 of the prosthetic heart valve 902 can comprise an outflow end portion 912 and an inflow end portion 914. The frame 910 can include a plurality of struts 916 forming first and second pluralities of apices 918, 920 at the outflow and inflow end portions 912, 914 of the frame 910, respectively. The frame 910 can also include a plurality of attachment structures 922 (e.g., three in the illustrated embodiment) that are coupled to at least some of the apices 918 of the outflow end portion 912. The attachment structures 922 (e.g., eyelets) can comprise openings 924 formed therein. As shown in FIG. 35, the apices 918 and the attachment structures 922, in combination with the suture loops 908, can be used to releasably couple the prosthetic heart valve 902 to the delivery apparatus 904, as further explained below.

In some embodiments, the attachment structures 922 can be evenly distributed circumferentially on the outflow end portion 912 of the frame 910. As shown in FIG. 36, for example, the outflow end portion 912 comprises 15 apices 918 and three attachment structures 922. The attachment structures 922 are evenly distributed around the outflow end portion 912 such that there are four apices 918 between each adjacent attachment structure 922. In other embodiments, the frame 910 can comprise more or fewer apices 918 and/or attachment structures 922, and/or the attachment structures 922 can be non-evenly distributed around the outflow end portion 912. In some embodiments, the frame 910 can have an attachment structure 922 at each apex 918.

Figures 37, 38:
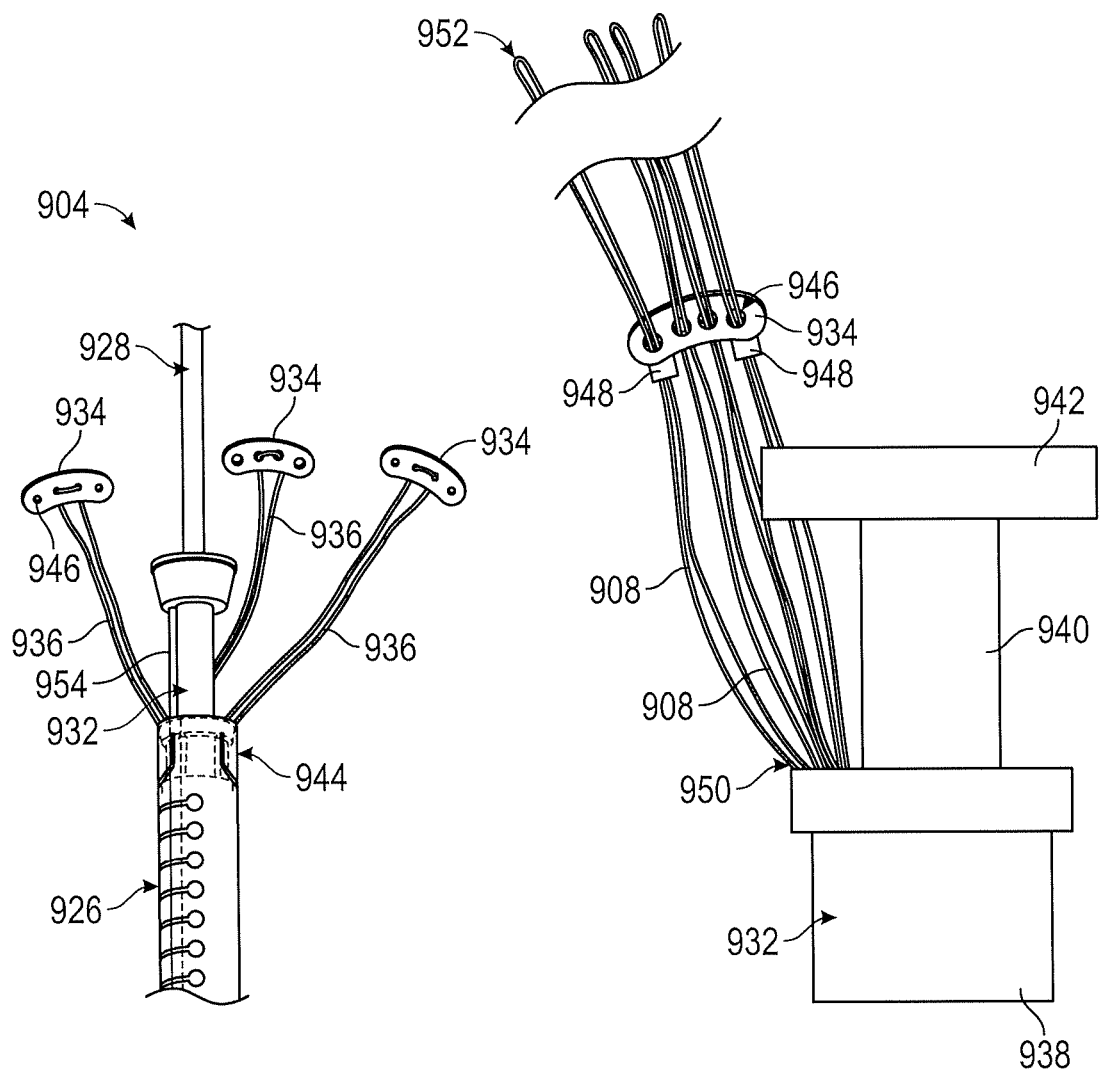
FIGS. 37-38 are various views of a delivery apparatus of the delivery assembly of FIG. 35.

Referring to FIG. 37, the delivery apparatus 904 can comprise a first catheter 926, a second catheter (not shown), a nose-cone catheter 928, and a delivery cylinder or sheath 930 (FIG. 40), a suture guide 932, the suture loops 908 (e.g., 12 in the illustrated embodiment, see FIG. 35), a plurality of apex guides 934 (e.g., three in the illustrated embodiment), and one or more attachment members or tethers 936 (e.g., three in the illustrated embodiment). The first catheter 926, second catheter, nose-cone catheter 928, and delivery cylinder 930 of the delivery apparatus 904 can be configured similar to the catheters 124, 126, 128 and the delivery cylinder 150 of the delivery apparatus 104, respectively.

Referring to FIG. 38, the suture guide 932 can comprise a proximal portion 938, an intermediate portion 940, and a distal portion 942. The suture loops 908 can be coupled to the proximal portion 938 of the suture guide 932 (e.g., with knots, adhesive, etc.). The proximal portion 938 of the suture guide 932 can be coupled (e.g., snap fit) to a distal end portion 944 of the first catheter 926, as shown in FIG. 37.

Figure 43:
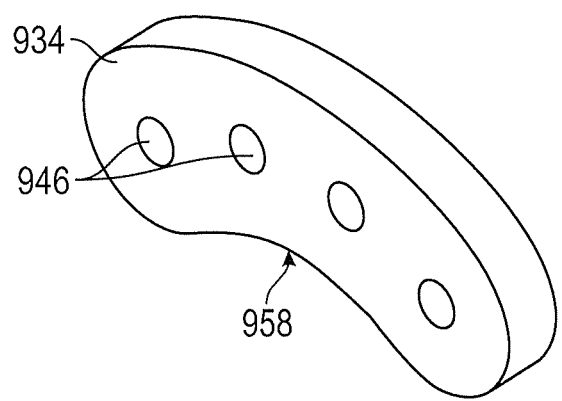
FIG. 43 is a perspective view of an apex guide of the delivery assembly of FIG. 35.

Referring to FIG. 43, the apex guides 934 can comprise one or more openings 946 (four in the illustrated embodiment. The openings 946 can each be configured to receive one or more of the suture loops 908 and/or the tethers 936. For example, as shown in FIG. 38, each of the suture loops 908 can be threaded through a respective opening 946 of the apex guides 934. As such, the apex guides 934 can move (e.g., slide) relative to the suture loops 908. It should be noted that FIG. 38 shows only one apex guide 934 and four suture loops 908 for purposes of illustration.

In some embodiments, the suture loops 908 can comprise one or more stopper members 948 configured to prevent the apex guides 934 from moving toward fixed end portions 950 of the suture loops 908. For example, in the illustrated embodiment, the two outer-most suture loops 908 that extend through each of the sutures guides 934 each have a stopper member 948. The stopper members 948 comprise knots formed in the suture loops 908, ferrules, beads, and/or other objects that are crimped and/or otherwise coupled to the suture loops 908. The stopper members 948 do not, however, prevent the apex guides 934 from moving toward free end portions 952 of the suture loops 908.

Referring again to FIG. 37, the apex guides 934 can, for example, be coupled to the suture guide 932 with the tethers 936. The tethers 936 can keep the apex guides 934 attached to the delivery apparatus 904 when the prosthetic heart valve 902 is released from the delivery apparatus 904 by retracting the suture loops 908 from the apices 918 and attachment structures 922 of the prosthetic heart valve 902. The tethers 936 can, for example, extend through the inner-most openings 946 of a respective apex guide 934. In other embodiments, the tethers 936 can be coupled to an additional or different component of the delivery apparatus (e.g., the distal end portion 944 of the first catheter 926).

Figure 41:
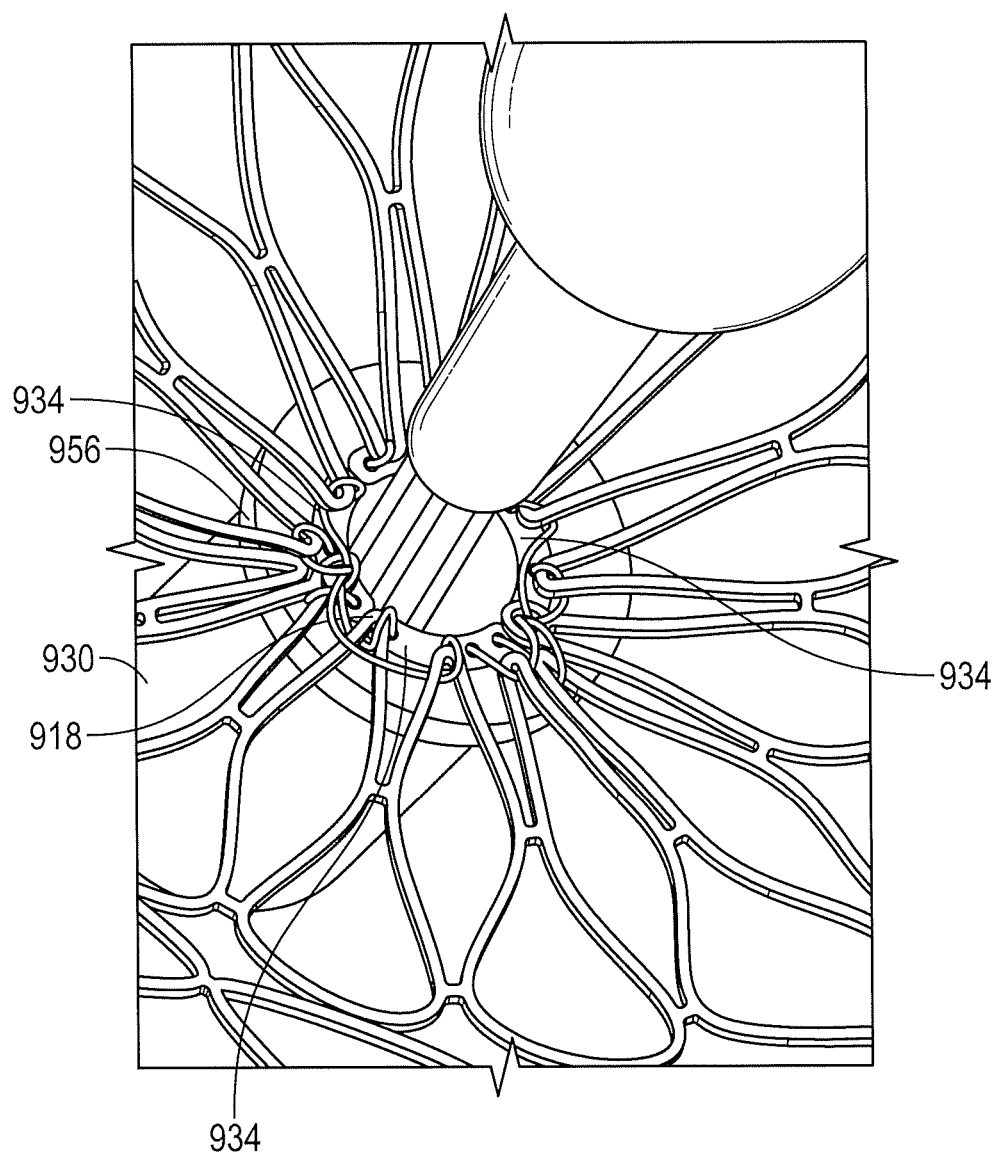
Figure 42:
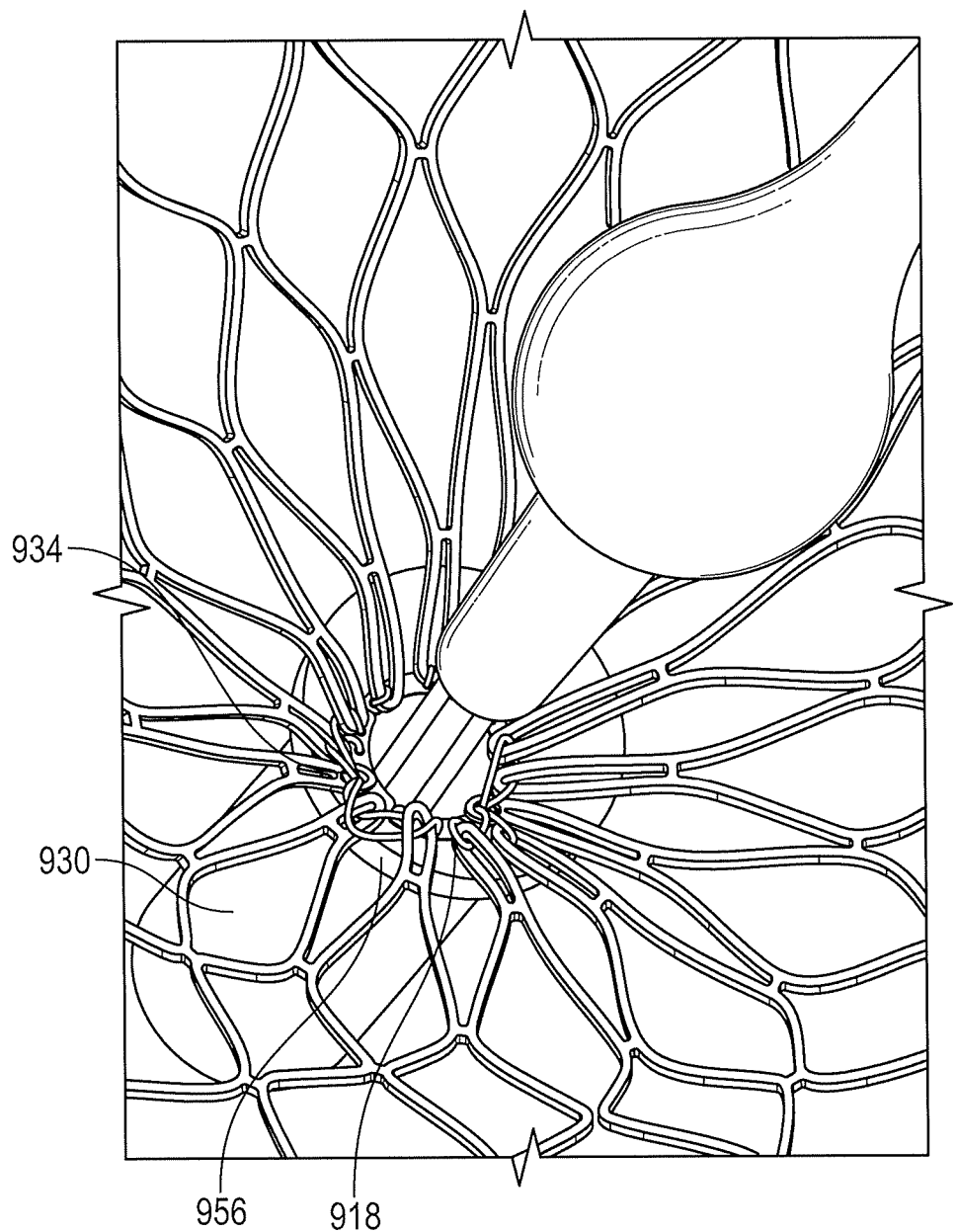

The apex guides 934 can have a generally curved or bean-shape, as shown in the illustrated embodiment. As such, the apex guides 934 collectively can form an annular ring having an outer diameter similar to the inner diameter of the delivery cylinder 930 when the apex guides 934 are disposed adjacent and contacting each other in an array, as best shown in FIG. 41. The array of apex guides 934 can also have an inner diameter that is configured to allow components (e.g., the nose-cone catheter 928 to extend therethrough. In other embodiments, the apex guides 934 can comprise various other shapes, including cylindrical, ovular, rectangular, etc.

Referring again to FIG. 35, the prosthetic heart valve 902 can be attached to the delivery apparatus 904, for example, by wrapping the free end portions 952 of each of the suture loops 908 around a respective apex 918 of the prosthetic heart valve 902 that does not have an attachment structure 922. The free end portions 952 can then be threaded through respective, adjacent attachment structures 922 of the prosthetic heart valve 902. As such, each of the attachment structures 922 has four suture loops 908 extending therethrough (i.e., two suture loops 908 from each of the two adjacent apex guides 934). The free end portions 952 of the suture loops 908 can then extend radially inward toward the intermediate portion 940 of the suture guide 932. The free end portions 952 can be releasably secured to relative to the prosthetic heart valve 902 and the suture guide 932 via one or more release pins 954 that extend from the proximal portion 938 of the suture guide 932, adjacent the intermediate portion 940 of the suture guide 932 and through the suture loops 908, and to the distal portion 942 of the suture guide 932 (e.g., similar to the manner shown in FIG. 25).

Figure 39:
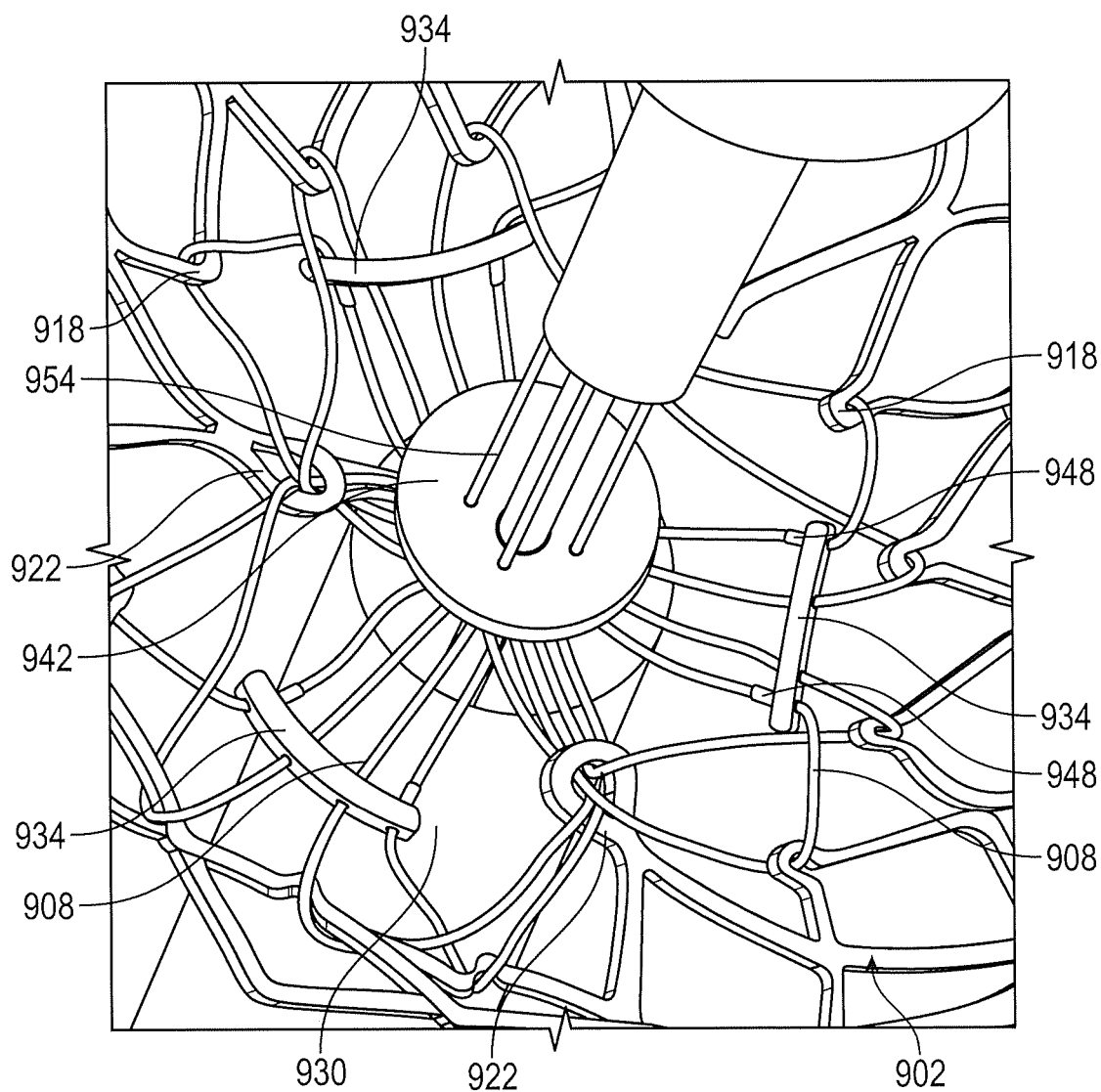
FIGS. 39-42 are various views of the delivery assembly of FIG. 35.
Figure 40:
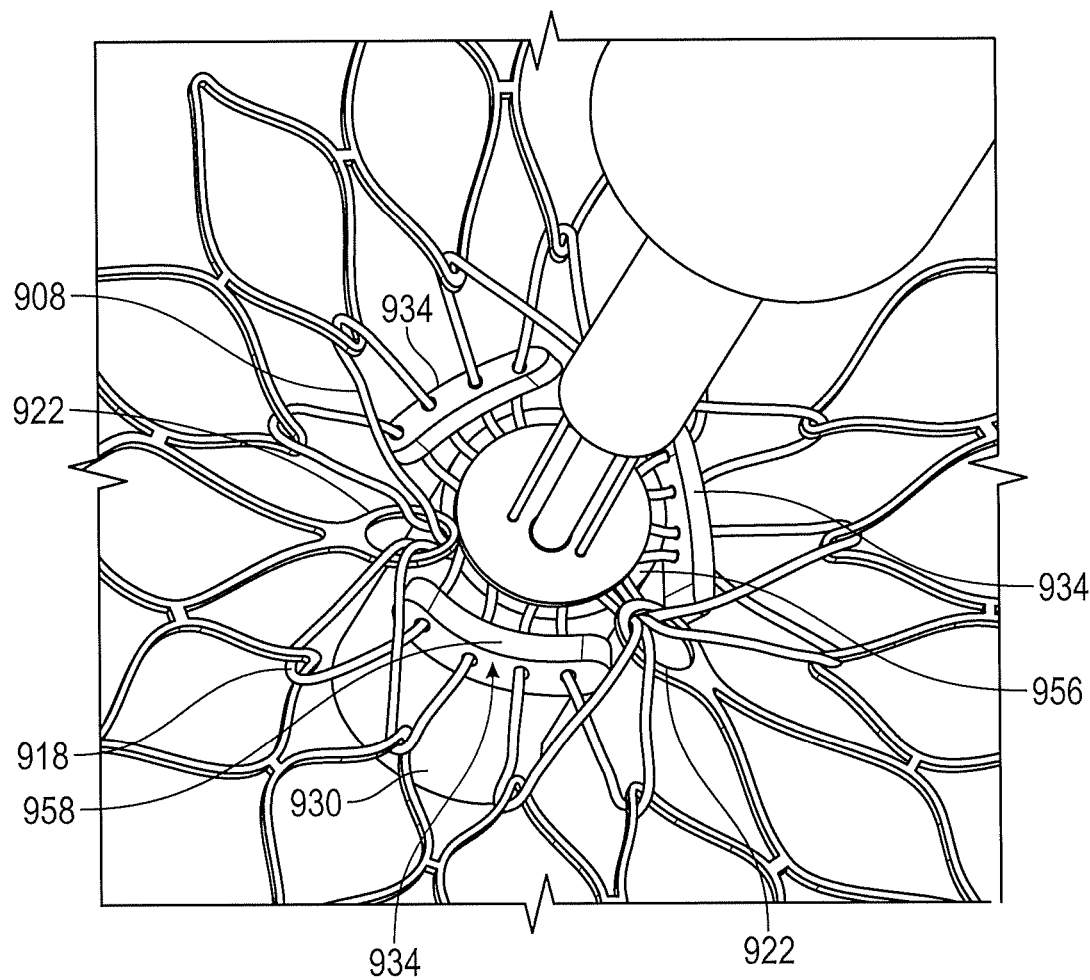

FIGS. 39-42 illustrate the delivery apparatus 904 retrieving the prosthetic heart valve 902 into the delivery cylinder 930. FIG. 39 shows the prosthetic heart valve 902 fully deployed from the delivery cylinder 930. In this configuration, the apex guides 934 are disposed on the respective suture loops 908 between the stopper members 948 and the apices 918 of the prosthetic heart valve 902. Referring to FIG. 40, as the delivery cylinder 930 and the prosthetic heart valve 902 are moved toward each other (e.g., by advancing the delivery cylinder 930 distally relative to the prosthetic heart valve 902 and/or retracting the prosthetic heart valve 902 proximally relative to the delivery cylinder 930), the suture loops 908 are drawn into the delivery cylinder 930, and the apex guides 934 abut the distal end 956 of the delivery cylinder 930. Referring to FIG. 41, the suture loops 908 then slide relative to the apex guides 934 drawing the apices 918 toward the apex guides 934 and the distal end 956 of the delivery cylinder 930 until the apices 918 contact the apex guides 934. The apex guides 934 then pivot about the distal end 956 of the delivery cylinder 930 from the orientation shown in FIG. 40 (i.e., with smaller radial curves 958 of the apex guides 934 directed generally distally) to the orientation shown in FIG. 41 (i.e., with the smaller radial curves 958 of the apex guides 934 directed generally inwardly) and then to the orientation shown in FIG. 42 (i.e., the orientation in which the smaller radial curves 958 of the apex guides 934 directed generally proximally). As the apex guides 934 pivot, the apices 918 slide along the inner surfaces of the apex guides 934 and are drawn into the delivery cylinder 930 without snagging on the distal end 956 of the delivery cylinder 930.

Figure 44:
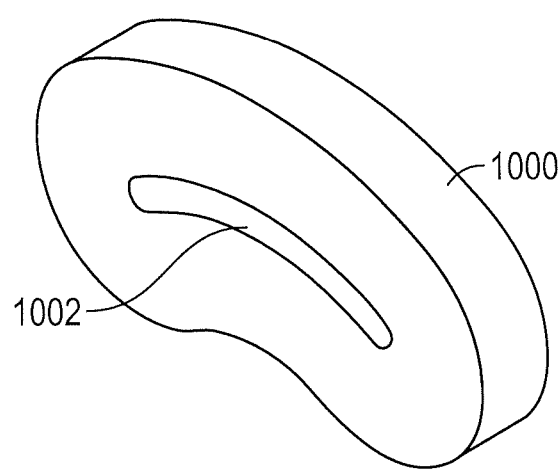
FIG. 44 is a perspective view of another exemplary embodiment of an apex guide.
Figure 45:
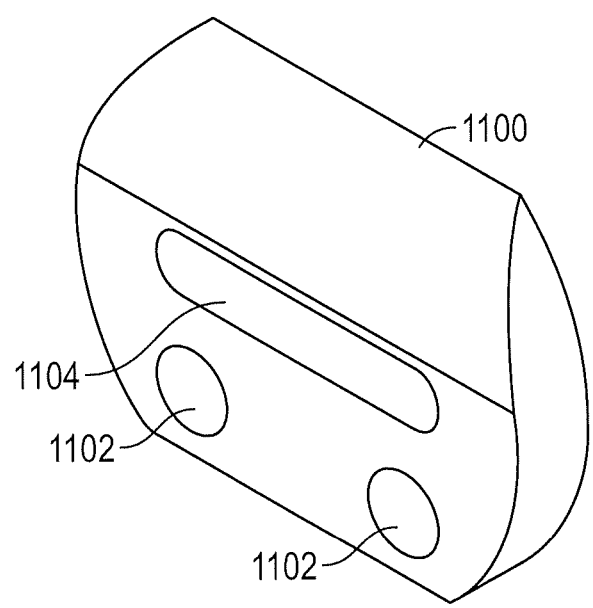
FIG. 45 is a perspective view of another exemplary embodiment of an apex guide.

FIGS. 44-45 show exemplary embodiments of apex guides 1000, 1100, which can be used in lieu of or in addition to the apex guides 934. The apex guide 1000 is similar to the apex guides 934 but comprises a single arcuate slit 1002 rather than the openings 924. The apex guide 1100 comprises a plurality of openings 1102 and an elongate slit 1104. In some embodiments, a tether 936 can be looped through the openings 1102, and the suture loops 908 can extend through the slit 1104.

Figure 46:
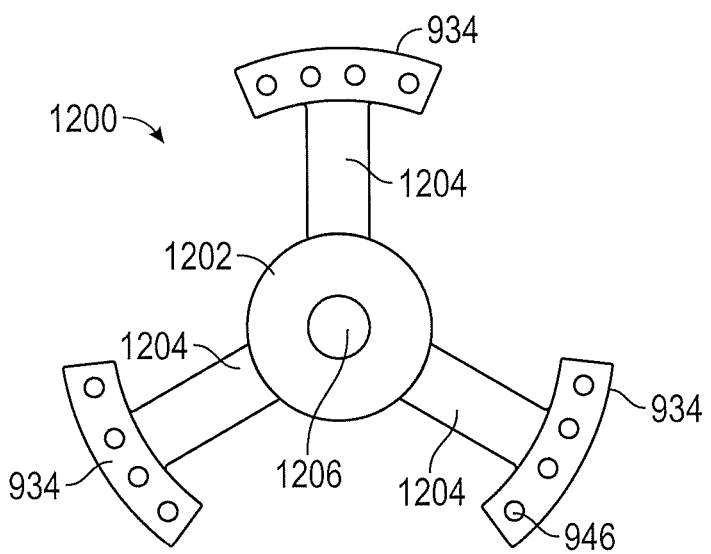
FIG. 46 is a plan view of an exemplary embodiment of an attachment member and the apex guides of FIG. 43.
Figure 47:
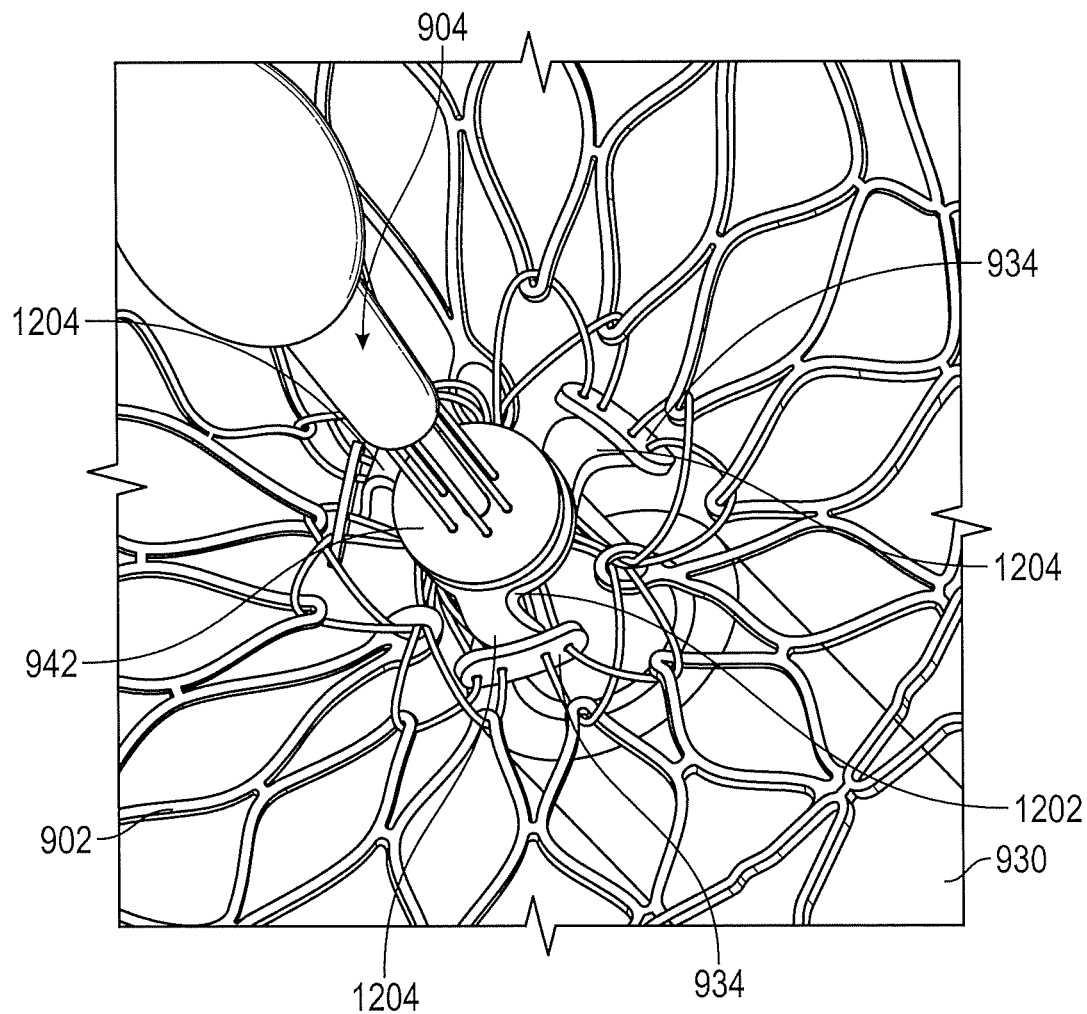
FIG. 47 is a perspective view of the attachment member of FIG. 46 and the delivery assembly of FIG. 35.

FIG. 46-47 show an attachment member 1200 that can be used in lieu of or in addition to the tethers 936. As best shown in FIG. 46, the attachment member 1200 comprises a hub 1202, a plurality of legs 1204 (e.g., three in the illustrated embodiment), and a central opening 1204. The legs 1204 can extend outwardly from the hub 1202. The apex guides 932 can be coupled to the legs 1204 (e.g., molded or with an adhesive). The central opening 1206 can extend through the hub 1202 and can be configured to receive the intermediate portion 940 of the suture guide 932, as shown in FIG. 47. The attachment member 1200 can be formed of various elastomeric materials, such as polyurethane, polyether block amide, and/or silicone, to name a few.

Figure 48:
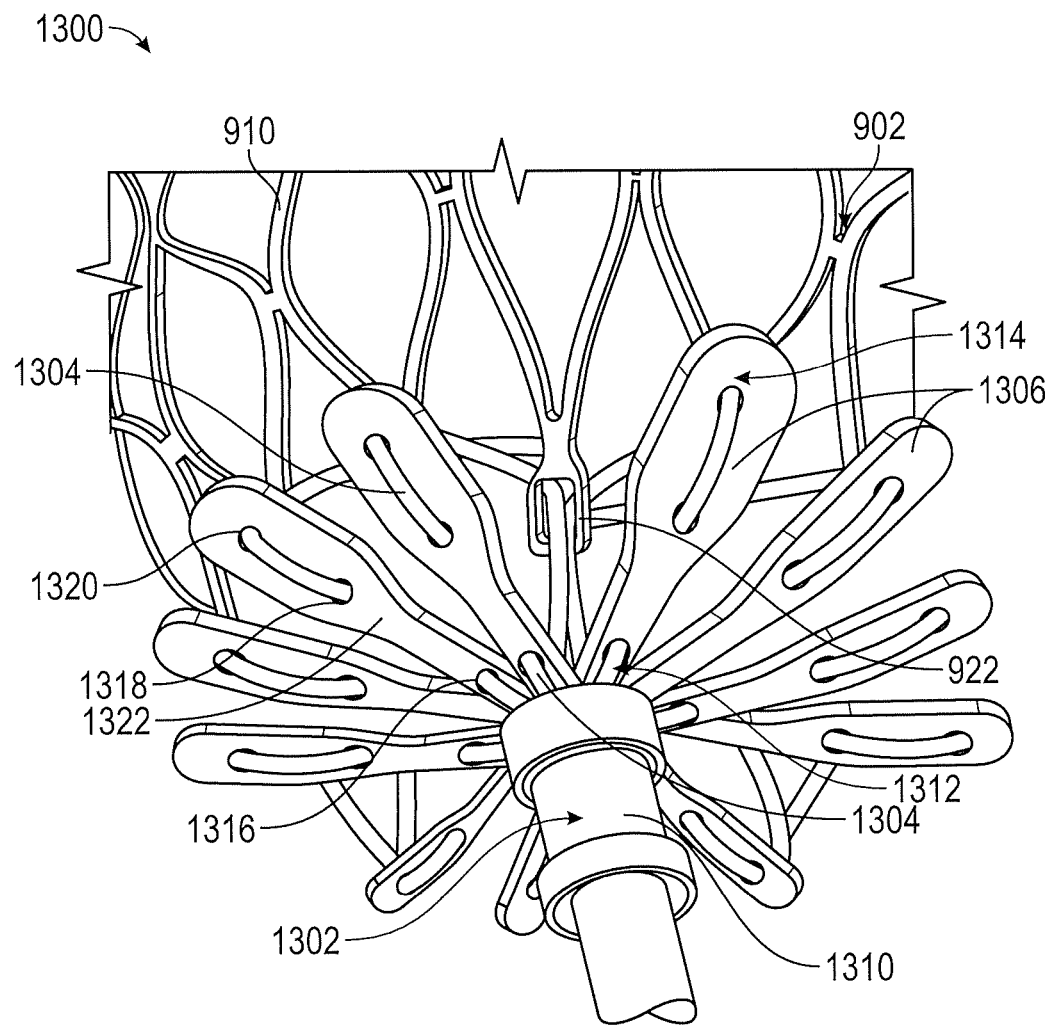
FIG. 48 is a perspective view of a delivery assembly comprising another exemplary embodiment of a delivery apparatus and the prosthetic heart valve frame of FIG. 36.
Figure 49:
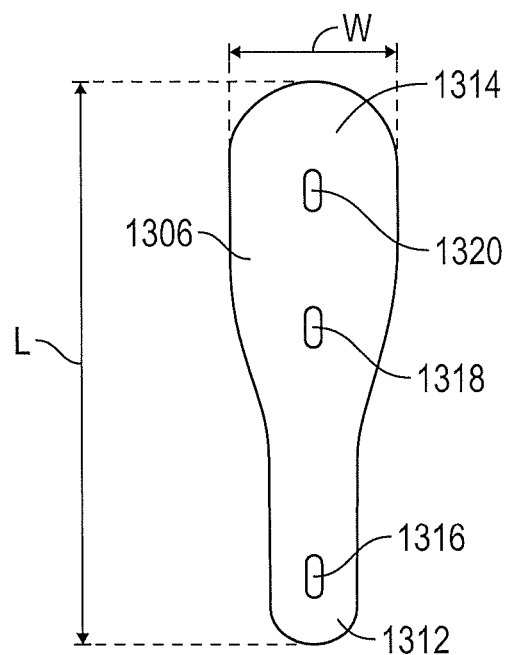
FIG. 49 is a plan view of an apex guide of the delivery apparatus of FIG. 48.
Figure 50:
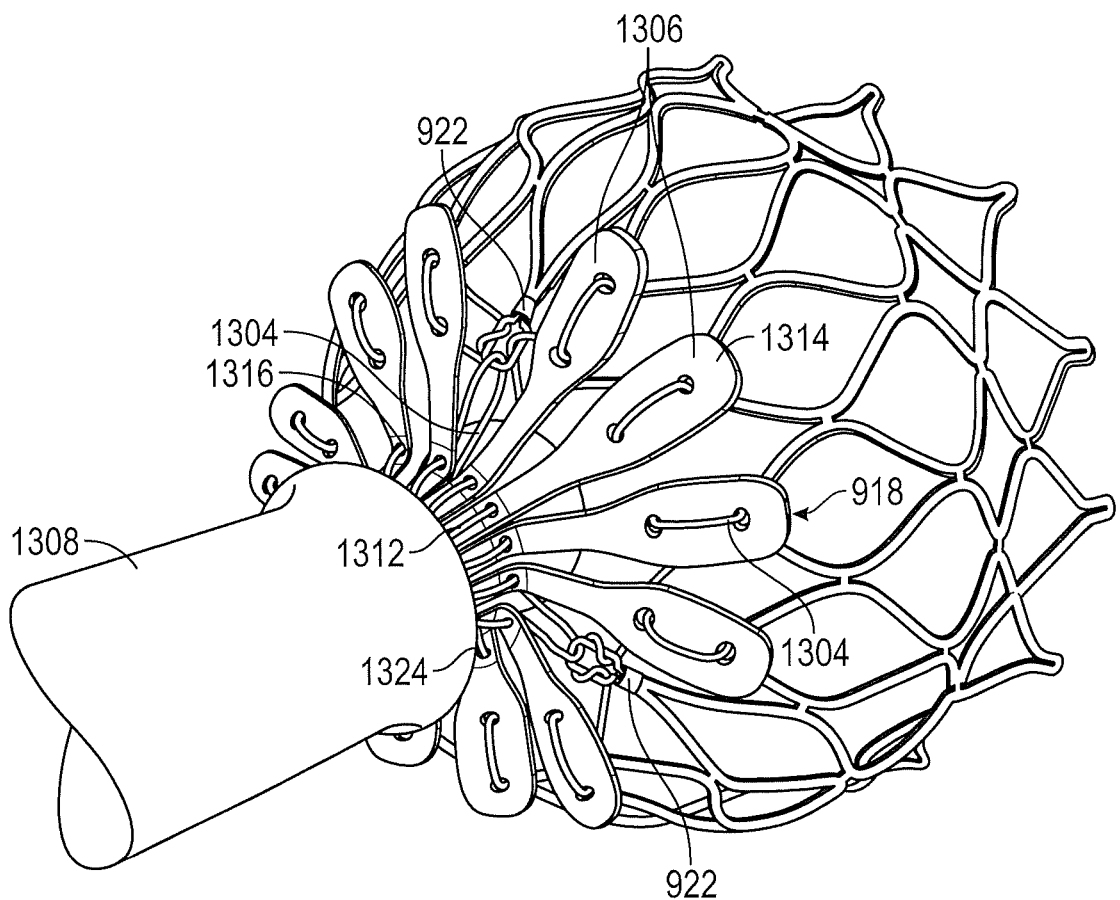
FIGS. 50-52 are various views of the delivery assembly of FIG. 48.

FIGS. 48-52 show an exemplary embodiment of a delivery apparatus 1300. The delivery apparatus 1300 can be used, for example, with the prosthetic heart valve 902. Referring to FIG. 48, the delivery apparatus 1300 can comprise a suture guide 1302, a plurality of suture loops 1304 (e.g., 12 in the illustrated embodiment), a plurality of apex guides or petals 1306 (e.g., 12 in the illustrated embodiment), and a delivery cylinder 1308 (FIG. 50). The suture loops 1304 can extend through and couple the apex guides 1306 to the suture guide 1302, and the apex guides 1306 can prevent or reduce the likelihood of the apices 918 of the prosthetic heart valve 902 of snagging or on a delivery cylinder 1308 of the delivery apparatus 1300.

The suture guide 1302 can be configured similar to the suture guide 932 of the delivery apparatus 904 and can be coupled to a distal end of a catheter shaft. The suture guide 1302 can comprise a proximal portion 1310, an intermediate portion (not shown), and a distal portion (not shown). The suture loops 1304 can be coupled to and extend from the proximal portion 1310 of the suture guide 1302.

Referring to FIG. 49, the apex guides 1306 can each include a proximal end portion 1312, a distal end portion 1314, a first opening 1316, a second opening 1318, and a third opening 1320. The first opening 1316 can be formed in the proximal end portion 1312, the third opening 1320 can be formed in the distal end portion 1314, and the second opening 1318 can be formed in apex guide 1306 between the first and third openings 1316, 1320. In some embodiments, the proximal end portion 1312 can be relatively narrower than the distal end portion 1314.

The apex guides 1306 can comprise a length L and a width W. The length L can be sized and configured such that the apex guides 1306 do not prevent the outflow end portion 912 of the prosthetic heart valve 902 from fully radially expanding when the prosthetic heart valve 902 and the apex guides 1306 are fully deployed from the delivery cylinder 1308 (e.g., FIG. 50). The width W can be sized such that each apex guide 1306 is circumferentially spaced apart relative to an adjacent apex guide 1306 when the prosthetic heart valve 902 and the apex guides 1306 are fully deployed from the delivery cylinder 1308 (e.g., FIG. 50).

In some embodiments, for example, the length L can be 0.2-0.5 in. (5-13 mm) and the width W can be 0.07-0.14 in. (1.5-4 mm). In particular embodiments, the length L can be 0.315-0.380 in. (8-9.65 mm), and the width W can be 0.094-0.110 in. (2.39-2.79 mm). In one specific embodiment, a apex guide 1306 having a length L of 0.315 in. (8.00 mm) and a width W of 0.094 in. (2.39 mm) can be used with a prosthetic heart valve 902 having a nominal outer diameter of 0.91 in (23 mm). In another specific embodiment, a apex guide 1306 having a length L of 0.35 in. (8.89 mm) and a width W of 0.105 in. (2.67 mm) can be used with a prosthetic heart valve 902 having a nominal outer diameter of 1.02 in. (26 mm). In yet another specific embodiment, a apex guide 1306 having a length L of 0.38 in. (9.65 mm) and a width W of 0.110 in. (2.79 mm) can be used with a prosthetic heart valve 902 having a nominal outer diameter of 1.14 in. (29 mm).

The apex guides 1306 can comprise a relatively thin, flat shape and can be formed from various thin, flexible materials including any of various suitable biocompatible polymers and metals. For example, the apex guides 1306 can be formed from polyester, PEEK, polycarbonate, stainless steel, nitinol, cobalt chromium, and/or other thin flexible material.

Referring again to FIG. 48, each of the apex guides 1306 can be coupled to the suture guide 1302 by threading a respective suture loop 1304 through the first opening 1316 of the apex guide 1306 from a radially outwardly facing surface 1322 of the apex guide 1306 (i.e., the surface facing away from the prosthetic heart valve 902 as illustrated in FIG. 48) to a radially inwardly facing surface of the apex guide 1306. The suture loop 1304 can then extend along the radially inwardly facing surface from the first opening 1316 to the second opening 1318 and can pass through the second opening 1318 to the radially outwardly facing surface 1322. The suture loop 1304 can then extend along the radially outwardly facing surface 1322 from the second opening 1318 to the third opening 1320 and can pass through the third opening 1320 to the radially inwardly facing surface.

The prosthetic heart valve 902 can then be coupled to the delivery apparatus 1300 by wrapping free end portions 952 (e.g., similar to the free end portions 952 FIG. 38) of each suture loop 1304 around a respective apex 918 of the prosthetic heart valve 902 that does not have an attachment structure 922. The free end portions of the suture loops 1304 can then be threaded through respective, adjacent attachment structures 922 of the prosthetic heart valve 902. As such, each of the attachment structures 922 has four suture loops 1304 extending therethrough (i.e., two suture loops 1304 from each of the two adjacent apices 918). The free end portions then extend radially inwardly toward the intermediate portion of the suture guide 1302. The free ends of the suture loops 1304 can be releasably secured to relative to the prosthetic heart valve 902 and the suture guide 1302 via one or more release pins (e.g., similar to release pin 542 of the delivery apparatus 500 shown in FIG. 25).

Figure 51:
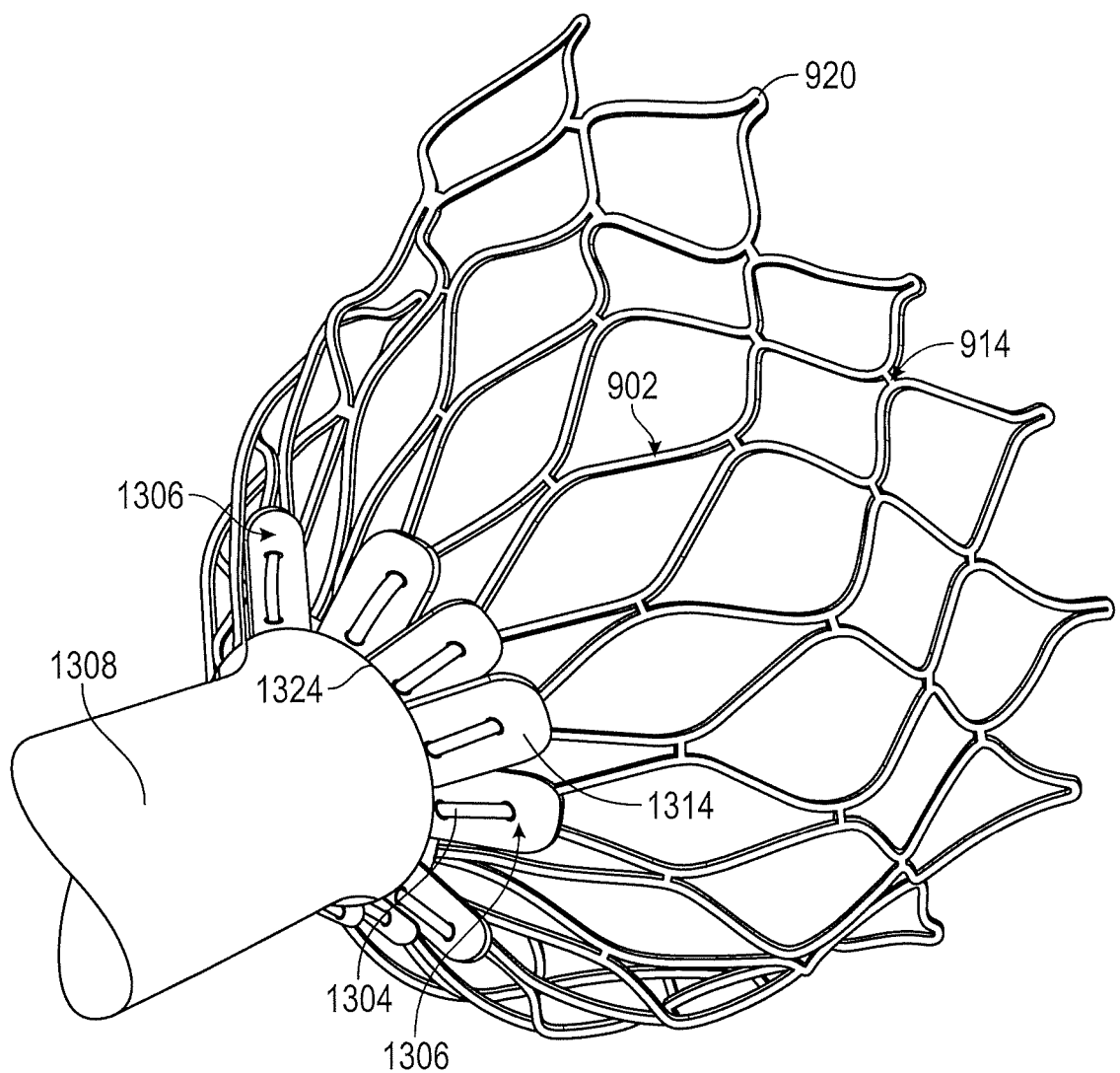
Figure 52:
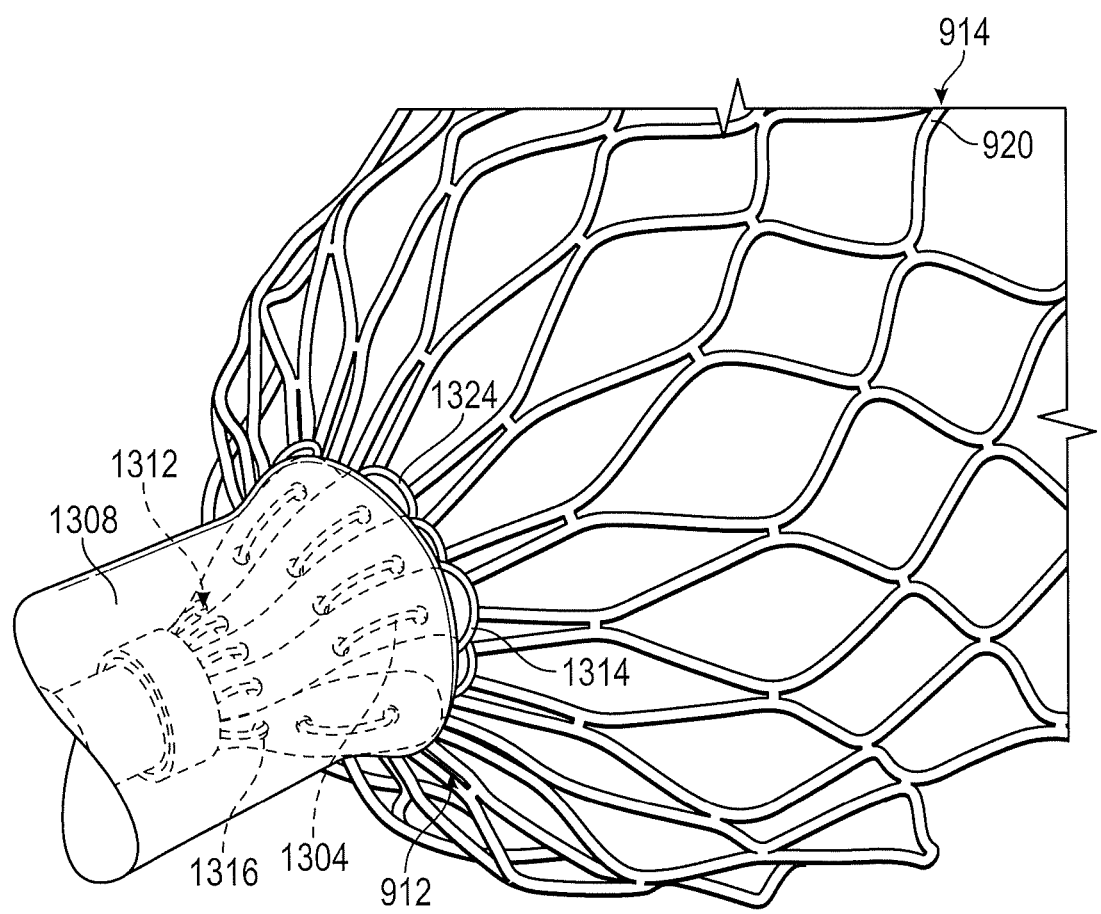

FIGS. 50-52 show the prosthetic heart valve 902 being retrieved into the delivery cylinder 1308. As mentioned above, FIG. 50 shows the prosthetic heart valve 902 and the apex guides 1306 fully deployed from the delivery cylinder 1308. Referring to FIG. 51, as the delivery cylinder 1308 and the prosthetic heart valve 902 are moved toward each other (e.g., by advancing the delivery cylinder 1308 distally relative to the prosthetic heart valve 902 and/or retracting the prosthetic heart valve 902 proximally relative to the delivery cylinder 1308), the suture loops 908 and the proximal end portions 1312 of the apex guides 1306 are drawn into the delivery cylinder 1308. The distal end 1324 of the delivery cylinder 1308 contacts the radially outwardly facing surfaces 1322 of the apex guides 1306 and urges the apex guides 1306 radially inwardly from a radially-extending orientation (e.g., FIG. 50) to an axially-extending orientation (e.g., FIG. 51). This causes the outflow end portion 912 to radially compress, and the distal end portions 1314 of the apex guides 1306 to circumferentially overlap, as shown in FIG. 51. Referring to FIG. 52, the apices 918 of the prosthetic heart valve 902 are then drawn into the delivery cylinder 1308 without snagging on the distal end 1324 of the delivery cylinder 1308 because the apices 918 are disposed on the radially inwardly facing surface of the apex guides 1306, which can prevent direct contact between the apices 918 and the distal end 1324 of the delivery cylinder 1308.

As described above, attaching a prosthetic heart valve to a delivery apparatus with apex guides (e.g., the apex guides 934, 1000, 1100, 1306) can prevent (or reduce the likelihood of) apices and/or attachment structures from catching or snagging on a distal end of a delivery cylinder when the prosthetic heart valve is at least partially retrieved into the delivery cylinder after being fully deployed from the delivery cylinder. This can, for example, make repositioning and/or retrieving the prosthetic heart valve 902 significantly easier, quicker, and or require less force. It can also prevent or reduce damage to the delivery apparatus (e.g., tearing the delivery cylinder).

These features can be particularly advantageous when there is a steep angle between a longitudinal axis of a delivery cylinder and a longitudinal axis of the prosthetic heart valve during retrieval/repositioning of the prosthetic heart valve. A steep angle between the delivery cylinder and the prosthetic heart valve can be caused, for example, by the native anatomy of a patient. One particular example of this is when a retrograde delivery path (i.e., through the patient's aorta) is used for a transcatheter aortic valve implantation ("TAVI"), and the patient has a relatively short ascending aorta (e.g., the distance from the native aortic annulus to the aortic arch is relatively shorter than normal). This can result in a steep angle between the delivery cylinder and the deployed prosthetic heart valve because the sharp curve that the delivery apparatus has to make around the aortic arch tends position the delivery cylinder non-coaxial to the native aortic annulus in which the prosthetic heart valve is deployed.

It should be noted a delivery apparatus (e.g., the delivery apparatus 904, 1300) and a prosthetic heart valve (e.g., the prosthetic valves 102, 902) can be configured for various implantation locations and/or methods. For example, although the delivery apparatus 904 is shown coupled to an outflow end portion 912 of the prosthetic heart valve 902 (e.g., for retrograde TAVI), the delivery apparatus 904 can be coupled to the inflow end portion 914 of the prosthetic heart valve 902 (e.g., for transventricular TAVI).

The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

The invention claimed is:

1. A method for delivering a prosthetic valve to a native annulus of a heart, comprising:
   inserting a delivery apparatus into a patient's body;
   advancing the delivery apparatus to an implantation location within the native annulus;
   retracting a delivery sheath of the delivery apparatus relative to the prosthetic valve to expose the prosthetic valve from a distal end of the delivery sheath; and
   after the prosthetic valve is exposed from the delivery sheath, expanding the prosthetic valve from a radially compressed state to a radially expanded state by reducing axial tension on a first end and a second end of the prosthetic valve;
   wherein reducing the axial tension on the first end of the prosthetic valve precedes reducing the axial tension on the second end of the prosthetic valve.

2. The method of claim 1, wherein reducing the axial tension on the first end and the second end of the prosthetic valve comprises reducing the axial tension on a plurality of sutures of the delivery apparatus.

3. The method of claim 1, wherein reducing the axial tension on the first end and the second end of the prosthetic valve comprises moving a first manifold of the delivery apparatus axially proximally toward a second manifold of the delivery apparatus.

4. A method for delivering a prosthetic valve to a native annulus of a heart, comprising:
   inserting a delivery apparatus into a patient's body;
   advancing the delivery apparatus to an implantation location within the native annulus;
   retracting a delivery sheath of the delivery apparatus relative to the prosthetic valve to expose the prosthetic valve from a distal end of the delivery sheath; and
   after the prosthetic valve is exposed from the delivery sheath, expanding the prosthetic valve from a radially compressed state to a radially expanded state by reducing axial tension on a first end and a second end of the prosthetic valve;
   wherein reducing the axial tension on the first end and the second end of the prosthetic valve comprises moving a first manifold of the delivery apparatus axially proximally toward a second manifold of the delivery apparatus, and
   wherein the radially expanded state of the prosthetic valve is a first radially expanded state, and the method further comprises expanding the prosthetic valve from the first radially expanded state to a second radially expanded state by radially converging the first end and the second end of the prosthetic valve and axially compressing the first end and the second end of the prosthetic valve by moving the first manifold of the delivery apparatus axially proximally toward the second manifold of the delivery apparatus, wherein the prosthetic valve is radially larger in the second radially expanded state than in the first radially expanded state.

5. The method of claim 4, wherein reducing the axial tension on the first end of the prosthetic valve and reducing the axial tension on the second end of the prosthetic valve occur simultaneously.

6. The method of claim 4, further comprising radially compressing the prosthetic valve by moving the first manifold of the delivery apparatus axially distally away from the second manifold of the delivery apparatus.

7. A method for delivering a prosthetic valve to a native annulus of a heart, comprising:
   inserting a sheath of a delivery apparatus into a patient's body, wherein a distal end portion of the prosthetic valve is releasably coupled to a first suture guide of the delivery apparatus via one or more first sutures, wherein a proximal end portion of the prosthetic valve is releasably coupled to a second suture guide of the delivery apparatus via one or more second sutures, and wherein the prosthetic valve, the first suture guide, and the second suture guide are disposed within the sheath;
   advancing the sheath together with the prosthetic valve to an implantation location within the native annulus;

retracting the sheath to expose the prosthetic valve, the first suture guide, and the second suture guide from the sheath; and after the prosthetic valve, the first suture guide, and the second suture guide are exposed from the sheath, expanding the prosthetic valve from a radially compressed state to a radially expanded state by moving the first suture guide and the second suture guide toward each other;

wherein after moving the first suture guide and the second suture guide toward each other, the method further comprises reducing tension in the first sutures or the second sutures.

8. The method of claim 7, wherein prior to moving the first suture guide and the second suture guide toward each other, the method further comprises reducing tension in the first sutures or the second sutures.

9. The method of claim 7, wherein prior to moving the first suture guide and the second suture guide toward each other, the method further comprises reducing tension in the first sutures and the second sutures.

10. The method of claim 7, wherein the first suture guide is coupled to a first shaft of the delivery apparatus, wherein the second suture guide is coupled to a second shaft of the delivery apparatus, and wherein the first shaft extends coaxially through the second shaft and the second suture guide.

11. A method for delivering a prosthetic valve to a native annulus of a heart, comprising:

inserting a sheath of a delivery apparatus into a patient's body, wherein a distal end portion of the prosthetic valve is releasably coupled to a first suture guide of the delivery apparatus via one or more first sutures, wherein a proximal end portion of the prosthetic valve is releasably coupled to a second suture guide of the delivery apparatus via one or more second sutures, and wherein the prosthetic valve, the first suture guide, and the second suture guide are disposed within the sheath;

advancing the sheath together with the prosthetic valve to an implantation location within the native annulus;

retracting the sheath to expose the prosthetic valve, the first suture guide, and the second suture guide from the sheath; and after the prosthetic valve, the first suture guide, and the second suture guide are exposed from the sheath, expanding the prosthetic valve from a radially compressed state to a radially expanded state by moving the first suture guide and the second suture guide toward each other;

wherein after moving the first suture guide and the second suture guide toward each other, the method further comprises reducing tension in the first sutures and the second sutures.

12. A method for delivering a prosthetic valve to a native annulus of a heart, comprising:

inserting a sheath of a delivery apparatus into a patient's body, wherein a distal end portion of the prosthetic valve is releasably coupled to a first suture guide of the delivery apparatus via one or more first sutures, wherein a proximal end portion of the prosthetic valve is releasably coupled to a second suture guide of the delivery apparatus via one or more second sutures, and wherein the prosthetic valve, the first suture guide, and the second suture guide are disposed within the sheath;

advancing the sheath together with the prosthetic valve to an implantation location within the native annulus;

retracting the sheath to expose the prosthetic valve, the first suture guide, and the second suture guide from the sheath; and after the prosthetic valve, the first suture guide, and the second suture guide are exposed from the sheath, expanding the prosthetic valve from a radially compressed state to a radially expanded state by moving the first suture guide and the second suture guide toward each other;

wherein the first suture guide is coupled to a first shaft of the delivery apparatus, wherein the second suture guide is coupled to a second shaft of the delivery apparatus, and wherein the first shaft extends coaxially through the second shaft and the second suture guide, and wherein the second suture guide comprises a first lumen, a plurality of first openings, and a plurality of second openings, wherein the first openings and the second openings are disposed radially outwardly relative to the first lumen, wherein the second openings are disposed radially outwardly relative to the first openings, wherein the first shaft extends through the first lumen of the second suture guide, wherein the first sutures extend through the first openings of the second suture guide, and wherein the second sutures extend through the second openings of the second suture guide.

13. A method for delivering a prosthetic valve to a native annulus of a heart, comprising:

inserting a sheath of a delivery apparatus into a patient's body, wherein a distal end portion of the prosthetic valve is releasably coupled to a first suture guide of the delivery apparatus via one or more first sutures, wherein a proximal end portion of the prosthetic valve is releasably coupled to a second suture guide of the delivery apparatus via one or more second sutures, wherein the first sutures and the second sutures are coupled to a tensioning member, and wherein the prosthetic valve, the first suture guide, and the second suture guide are disposed within the sheath;

advancing the sheath together with the prosthetic valve to an implantation location within the native annulus;

retracting the sheath to expose the prosthetic valve, the first suture guide, and the second suture guide from the sheath; and after the prosthetic valve, the first suture guide, and the second suture guide are exposed from the sheath, expanding the prosthetic valve from a radially compressed state to a first radially expanded state by moving the tensioning member distally relative to the first suture guide and the second suture guide, wherein in the first radially expanded state, the prosthetic valve comprises a first length and a first diameter.

14. The method of claim 13, further comprising expanding the prosthetic valve from the first radially expanded state to a second radially expanded state by moving the tensioning member proximally relative to the first suture guide and the second suture guide and by moving the first suture guide and the second suture guide toward each other, wherein in the second radially expanded state, the prosthetic valve comprises a second length and a second diameter, wherein the second length is less than the first length, and wherein the second diameter is greater than the first diameter.

15. The method of claim 14, wherein the prosthetic valve comprises a cylindrical shape in the first radially expanded state.

16. The method of claim 15, wherein the prosthetic valve comprises a more spherical shape in the second radially expanded state than the cylindrical shape in the first radially expanded state.

17. The method of claim 16, wherein the first suture guide is coupled to a first shaft, wherein the second suture guide is coupled to a second shaft, wherein the tensioning member is coupled to a third shaft, wherein the first shaft extends through the second shaft and the third shaft, and wherein the third shaft is disposed within the second shaft.

18. The method of claim 17, wherein expanding the prosthetic valve from the radially compressed state to the first radially expanded state includes moving the third shaft relative to the first shaft and the second shaft, and wherein expanding the prosthetic valve from the first radially expanded state to the second radially expanded state includes moving the first shaft and the second shaft relative to the third shaft.

* * * * *